US010266843B2

(12) United States Patent
DeRosa et al.

(10) Patent No.: US 10,266,843 B2
(45) Date of Patent: Apr. 23, 2019

(54) MULTIMERIC CODING NUCLEIC ACID AND USES THEREOF

(71) Applicant: Translate Bio, Inc., Cambridge, MA (US)

(72) Inventors: Frank DeRosa, Cambridge, MA (US); Michael Heartlein, Cambridge, MA (US); Daniel Crawford, Cambridge, MA (US); Shrirang Karve, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/482,431

(22) Filed: Apr. 7, 2017

(65) Prior Publication Data
US 2017/0314041 A1 Nov. 2, 2017

Related U.S. Application Data

(60) Provisional application No. 62/320,073, filed on Apr. 8, 2016.

(51) Int. Cl.
| *C07H 21/02* | (2006.01) |
| *C07H 21/04* | (2006.01) |
| *C12N 15/85* | (2006.01) |
| *C07K 14/505* | (2006.01) |
| *C12N 9/10* | (2006.01) |
| *C12N 9/02* | (2006.01) |
| *C07K 14/705* | (2006.01) |
| *A61K 48/00* | (2006.01) |
| *A61K 38/17* | (2006.01) |
| *A61K 38/44* | (2006.01) |
| *A61K 38/45* | (2006.01) |
| *A61K 38/18* | (2006.01) |
| *A61K 31/7115* | (2006.01) |
| *A61K 31/7125* | (2006.01) |
| *C12P 21/00* | (2006.01) |
| *C12N 15/67* | (2006.01) |
| *A01K 67/00* | (2006.01) |

(52) U.S. Cl.
CPC .......... *C12N 15/85* (2013.01); *A61K 31/7115* (2013.01); *A61K 31/7125* (2013.01); *A61K 38/177* (2013.01); *A61K 38/1816* (2013.01); *A61K 38/44* (2013.01); *A61K 38/45* (2013.01); *A61K 48/005* (2013.01); *C07H 21/02* (2013.01); *C07K 14/505* (2013.01); *C07K 14/705* (2013.01); *C12N 9/0071* (2013.01); *C12N 9/1018* (2013.01); *C12N 15/67* (2013.01); *C12P 21/00* (2013.01); *C12Y 114/16001* (2013.01); *C12Y 201/03003* (2013.01); *C12N 2830/50* (2013.01)

(58) Field of Classification Search
CPC ...... C12N 15/85; C12N 15/67; C12N 9/0071; C12N 2830/50; C07K 14/505; C07K 14/705; A61K 48/005; A61K 31/7115; A61K 31/7125
See application file for complete search history.

(56) References Cited

U.S. PATENT DOCUMENTS

| 5,705,385 | A | 1/1998 | Bally et al. |
| 5,976,567 | A | 11/1999 | Wheeler |
| 5,981,501 | A | 11/1999 | Wheeler et al. |
| 6,489,464 | B1 * | 12/2002 | Agrawal ................ C07H 21/00 536/23.1 |
| 6,534,484 | B1 | 3/2003 | Wheeler et al. |
| 6,815,432 | B2 | 11/2004 | Wheeler et al. |
| 7,422,902 | B1 | 9/2008 | Wheeler et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,901,708 | B2 | 3/2011 | MacLachlan et al. |
| 8,101,741 | B2 | 1/2012 | MacLachlan et al. |
| 8,188,263 | B2 | 5/2012 | MacLachlan et al. |
| 8,236,943 | B2 | 8/2012 | Lee et al. |
| 8,329,070 | B2 | 12/2012 | MacLachlan et al. |
| 8,513,403 | B2 | 8/2013 | MacLachlan et al. |
| 8,569,256 | B2 | 10/2013 | Heyes et al. |
| 8,710,200 | B2 | 4/2014 | Schrum et al. |
| 8,822,663 | B2 | 9/2014 | Schrum et al. |
| 8,883,202 | B2 | 11/2014 | Manoharan et al. |
| 8,980,864 | B2 | 3/2015 | Hoge et al. |
| 9,051,567 | B2 | 6/2015 | Fitzgerald et al. |
| 9,061,059 | B2 | 6/2015 | Chakraborty et al. |
| 9,089,604 | B2 | 7/2015 | Chakraborty et al. |
| 9,095,552 | B2 | 8/2015 | Chakraborty et al. |
| 9,107,886 | B2 | 8/2015 | Chakraborty et al. |
| 9,114,113 | B2 | 8/2015 | Chakraborty et al. |

(Continued)

FOREIGN PATENT DOCUMENTS

| CA | 2807 552 | 9/2012 |
| EP | 1519 714 | 10/2010 |

(Continued)

OTHER PUBLICATIONS

Chasséet al., "Human recombinant adenovirus used to correct a mouse enzyme deficiency", Clinical Nutrition, Feb. 1990, vol. 9, No. 1, p. VIII.

(Continued)

*Primary Examiner* — Quang Nguyen
(74) *Attorney, Agent, or Firm* — Proskauer Rose LLP; Fangli Chen; Julio J. Mendez

(57) ABSTRACT

The present invention provides, among other things, multimeric coding nucleic acids that exhibit superior stability for in vivo and in vitro use. In some embodiments, a multimeric coding nucleic acid (MCNA) comprises two or more encoding polynucleotides linked via 3' ends such that the multimeric coding nucleic acid compound comprises two or more 5' ends.

16 Claims, 20 Drawing Sheets

Specification includes a Sequence Listing.

(56) References Cited

U.S. PATENT DOCUMENTS

| | | |
|---|---|---|
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,535 B2 | 8/2016 | de Fougerolles et al. |
| 9,428,751 B2 | 8/2016 | MacDonald et al. |
| 9,447,164 B2 | 9/2016 | Schrum et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 9,616,084 B2 | 4/2017 | Mutzke |
| 9,623,095 B2 | 4/2017 | Kallen et al. |
| D787,703 S | 5/2017 | Mayer |
| 9,636,301 B2 | 5/2017 | Weber |
| 9,655,955 B2 | 5/2017 | Hoerr et al. |
| 9,657,295 B2 | 5/2017 | Schrum et al. |
| 9,669,089 B2 | 6/2017 | Thess et al. |
| 9,670,152 B2 | 6/2017 | Payne et al. |
| 9,675,668 B2 | 6/2017 | Bancel et al. |
| 9,682,139 B2 | 6/2017 | Monoharan et al. |
| 9,683,233 B2 | 6/2017 | Thess |
| 9,687,550 B2 | 6/2017 | Manoharan et al. |
| 9,688,729 B2 | 6/2017 | Kramps et al. |
| 2002/0192651 A1 | 12/2002 | Wheeler et al. |
| 2003/0181410 A1 | 9/2003 | Wheeler et al. |
| 2004/0043923 A1 | 3/2004 | Parma et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2011/0244026 A1 | 10/2011 | Guild et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0082092 A1 | 3/2016 | Hoerr et al. |
| 2016/0089424 A1 | 3/2016 | Hoerr et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |

(56) References Cited

U.S. PATENT DOCUMENTS

| | | |
|---|---|---|
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baum Hoff et al. |
| 2017/0029847 A1 | 2/2017 | Thess |
| 2017/0042814 A1 | 2/2017 | Yaworski et al. |
| 2017/0056528 A1 | 3/2017 | De Fougerolles et al. |
| 2017/0056529 A1 | 3/2017 | Thess et al. |
| 2017/0065675 A1 | 3/2017 | Bancel et al. |
| 2017/0065727 A1 | 3/2017 | Fotin-Mleczek et al. |
| 2017/0114378 A1 | 4/2017 | Wochner et al. |
| 2017/0128549 A1 | 5/2017 | Fotin-Mileczek et al. |
| 2017/0136131 A1 | 5/2017 | Roy et al. |
| 2017/0136132 A1 | 5/2017 | Roy et al. |
| 2017/0143631 A1 | 5/2017 | Chen et al. |
| 2017/0143796 A1 | 5/2017 | Schrum et al. |
| 2017/0151333 A1 | 6/2017 | Heyes et al. |
| 2017/0157268 A1 | 6/2017 | Ansell et al. |
| 2017/0166905 A1 | 6/2017 | Eberle et al. |
| 2017/0182081 A1 | 6/2017 | Mutzke |

FOREIGN PATENT DOCUMENTS

| | | |
|---|---|---|
| EP | 2449 106 | 5/2012 |
| EP | 2338 478 | 6/2013 |
| EP | 2823 809 | 1/2015 |
| WO | WO2005/026372 | 3/2005 |
| WO | WO2005/121348 A1 | 12/2005 |
| WO | WO2009/127060 | 10/2009 |
| WO | WO 2009/127230 * | 10/2009 |
| WO | WO2010042877 A1 | 4/2010 |
| WO | WO2011/141705 | 11/2011 |
| WO | WO2012/019168 | 2/2012 |
| WO | WO2012/135805 | 10/2012 |
| WO | WO2013/039857 | 3/2013 |
| WO | WO2013/039861 | 3/2013 |
| WO | WO2013/040429 | 3/2013 |
| WO | WO2013/090186 A1 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/153052 | 9/2014 |
| WO | WO2014/158795 | 10/2014 |
| WO | WO2014/159813 | 10/2014 |
| WO | WO2015/006747 A2 | 1/2015 |
| WO | WO2015/023975 | 2/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/061491 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |
| WO | WO2017/102010 A1 | 6/2017 |
| WO | WO2017/103088 A1 | 6/2017 |
| WO | WO2017/108087 A1 | 6/2017 |
| WO | WO2017/109134 A1 | 6/2017 |
| WO | WO2017/109161 A1 | 6/2017 |

OTHER PUBLICATIONS

Gong et al., "mRNA-mRNA duplexes that auto-elicit Staufen1-mediated mRNA decay", Nat Struct Mol Biol., Jan. 1, 2013, vol. 20, No. 10, pp. 1214-1220.

Gong et al., "Supplementary Information: mRNA-mRNA duplexes that auto-elicit Staufen1-mediated mRNA decay", Nat Struct Mol Biol., Sep. 22, 2013, vol. 20, No. 10, pp. 1214-1220.

Karikó et al., "Incorporation of Pseudouridine Into mRNA Yields Superior Nonimmunogenic Vector With Increased Translational Capacity and Biological Stability", Mol Ther., Nov., 2008, vol. 16, No. 11, pp. 1833-1840.

Sumida et al., "In Vitro Selection of Fab Fragments by mRNA Display and Gene-Linking Emulsion PCR", Journal of Nucleic Acids, Jan. 1, 2012, vol. 249, No. 4968, pp. 505-509.

Vorobjev et al., "Nuclease resistance and RNase H sensitivity of oligonucleotides bridged by oligomethylenediol and oligoethylene glycol linkers", Antisense Nucleic Acid Drug Dev., Apr. 2001, vol. 11, No. 2, pp. 77-85.

* cited by examiner

MULTIMERIC CODING NUCLEIC ACID AND USES THEREOF

RELATED APPLICATIONS

This application claims priority to U.S. Provisional Application Ser. No. 62/320,073, filed Apr. 8, 2016, the disclosure of which is hereby incorporated by reference.

SEQUENCE LISTING

The present specification makes reference to a Sequence Listing (submitted electronically as a .txt file named "SL_SHR-1237US" on Apr. 7, 2017. The .txt file was generated Apr. 7, 2017 and is 49,249 bytes in size. The entire contents of the Sequence Listing are herein incorporated by reference.

BACKGROUND

Nucleic acid-based technologies are increasingly important for various therapeutic applications including, but not limited to, messenger RNA therapy, gene therapy, and gene editing, to name but a few. Such therapeutic applications typically require administration of exogenous polynucleotides (e.g. DNA or RNA), which is often hampered by the limited stability of such polynucleotides. For example, following their administration to a subject, many polynucleotides may be subject to nuclease (e.g. exonuclease and/or endonuclease) degradation. Nuclease degradation may negatively influence the capability of a polynucleotide to reach a target cell or to be transcribed and/or translated, the result of which is to preclude the exogenous polynucleotide from exerting an intended therapeutic effect.

SUMMARY OF THE INVENTION

The present invention provides, among other things, multimeric coding nucleic acids that exhibit superior stability for in vivo and in vitro use. The present invention also permits increased complexity and efficiency for nucleic acid based therapeutics.

In some aspects, the present invention provides a multimeric coding nucleic acid (MCNA) comprising one or more coding polynucleotides linked to one or more non-coding polynucleotides via a 3' end linkage between two or more of the polynucleotides (coding or non-coding) such that the MCNA compound comprises two or more 5' ends. In some embodiments, one or more of the 5'ends is modified to include a 5' end cap structure. In certain embodiments, one or more of the coding polynucleotides having a 5' end comprises a 5' end cap structure to facilitate translation of the coding polynucleotides. In certain embodiments, one or more of the polynucleotides having a 5'end structure comprises a 5' end cap structure to facilitate stability of the MCNA.

In some aspects, the present invention provides a multimeric coding nucleic acid (MCNA) comprising two or more encoding polynucleotides linked via 3' ends such that the multimeric coding nucleic acid compound comprises two or more 5' ends. In some embodiments, each of the two or more encoding polynucleotides is a synthetic polyribonucleotide. In some embodiments, each of the two or more encoding polynucleotides is a synthetic polydeoxyribonucleotide. In some embodiments, each of the two or more encoding polynucleotides is a synthetic polydeoxyribonucleotide or a polyribonucleotide. In some embodiments, each of the two or more encoding polynucleotides encodes a protein of interest. In some embodiments, each of the two or more encoding polynucleotides encodes a same protein. In some embodiments, each of the two or more encoding polynucleotides encodes a distinct protein.

In some embodiments, the MCNA compound comprises three or more encoding polynucleotides. In some embodiments, the compound comprises four or more encoding polynucleotides. In some embodiments, the compound comprises five or more encoding polynucleotides.

In some embodiments, one or more of the encoding polynucleotides comprise a 5' untranslated region (5' UTR) and/or a 3' untranslated region (3' UTR). In some embodiments, the one or more of the encoding polynucleotides comprise a 3' UTR. In some embodiments, the 3' UTR is 5-2,000 nucleotides in length. In some embodiments, the 3' UTR comprises a plurality of multi-A segments with spacers in between. In some embodiments, each of the multi-A segments comprises 8-50 consecutive adenosines. In some embodiments, the plurality of multi-A segments range from 1-100. In some embodiments, the spacers are of varying lengths ranging from 5-100. In some embodiments, the spacers comprise DNA, RNA and/or modified bases. In some embodiments, the modified bases are selected from 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine. In some embodiments, the 3' UTR comprises a pseudoknot structure. In some embodiments, the 3' UTR is not followed with a polyadenylation (poly-A) tail. In some embodiments, one or more of the encoding polynucleotides comprise a poly-A tail. In some embodiments, the poly-A tail is 25-5,000 nucleotides in length. In some embodiments, the 3' UTR binds to poly-A binding proteins (PABPs). In some embodiments, the 3' UTR comprises a "kissing loop" sequence motif.

In some embodiments, the 3' ends of the two or more encoding polynucleotides are linked via an oligonucleotide bridge comprising a 3'-3' inverted phosphodiester linkage. In some embodiments, the nucleotides comprising the oligonucleotide bridge are selected from the group consisting of 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine. In some embodiments, the oligonucleotide bridge comprises at least one covalent link to an active moiety. In some embodiments, the active moiety is a targeting group, peptide, contrast agent, small molecule, protein, DNA and/or RNA. In some embodiments, nucleotides proximal to the 3'-3' inverted linkage are functionalized with one or more tri-antennary GalNac targeting agents.

In some embodiments, the encoding polynucleotides comprise one or more modified nucleotides. In some embodiments, the modified nucleotides are selected from the group consisting of 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine. In some embodiments, the modified nucleotides substitute 1-100% of corresponding native bases. In some embodiments, the at least 25% of uridines are replaced with 2-thiouridines. In some embodiments, 100% of cytidines are replaced with 5-methylcytidines. In some embodiments, the modified nucleotides are further modified with a 4'-thio substitution on the ribose ring. In some embodiments, the native nucleotides are modified with a 4'-thio substitution on the ribose ring.

In some embodiments, one or more encoding polynucleotides in the MCNA comprise a polynucleotide portion that encodes a therapeutic protein. In some embodiments, one or more encoding polynucleotides in the MCNA comprise a polynucleotide portion that encodes an enzyme, a receptor, a ligand, a light chain or heavy chain of an antibody, a nuclease, or a DNA-binding protein. In certain embodiments, one or more encoding polynucleotides in the MCNA comprise a polynucleotide portion that encodes a nuclease.

In some embodiments, the two or more encoding polynucleotides in the MCNA each comprise a polynucleotide portion that encodes a therapeutic protein. In some embodiments, the two or more encoding polynucleotides in the MCNA each comprise a polynucleotide portion that encodes an enzyme, a receptor, a ligand, a light chain or heavy chain of an antibody, a nuclease, and/or a DNA-binding protein. In some embodiments, the two or more encoding polynucleotides in the MCNA each comprise a polynucleotide portion that encodes a nuclease.

In some embodiments, a first encoding polynucleotide in the MCNA comprises a polynucleotide portion that encodes a first protein and a second encoding polynucleotide in the MCNA comprising a polynucleotide portion that encodes a second protein that is the same protein as the first protein. In some embodiments, a first encoding polynucleotide in the MCNA comprises a polynucleotide portion that encodes a first protein and a second encoding polynucleotide in the MCNA comprises a polynucleotide portion that encodes a second protein that is distinct from the first protein. In certain embodiments, a first encoding polynucleotide in the MCNA comprises a polynucleotide portion that encodes a first protein in a class of an enzyme, a receptor, a ligand, a light chain or heavy chain of an antibody, a nuclease, or a DNA-binding protein, and a second encoding polynucleotide in the MCNA comprises a polynucleotide portion that encodes a second protein that is distinct from the first protein but in the same class as the first protein. In certain embodiments, a first encoding polynucleotide in the MCNA comprises a polynucleotide portion that encodes a first protein in a class of an enzyme, a receptor, a ligand, a light chain or heavy chain of an antibody, a nuclease, or a DNA-binding protein, and a second encoding polynucleotide in the MCNA comprises a polynucleotide portion that encodes a second protein that is distinct from the first protein and in a different class from the first protein. In certain embodiments, a first encoding polynucleotide in the MCNA comprises a polynucleotide portion that encodes a light chain of an antibody and a second encoding polynucleotide in the MCNA comprises a polynucleotide portion that encodes a heavy chain in the antibody.

In some aspects, the present invention provides a multimeric nucleic acid (MNA) comprising two or more polynucleotides linked via at least one 3' end linkage between two or more of the polynucleotides such that the MNA compound comprises two or more 5' ends. In some embodiments, one or more of the 5' ends is modified to facilitate stability of the MNA. In certain embodiments, the two or more polynucleotides linked via the at least one 3' end linkage each are non-coding nucleotides.

In some aspects, the present invention provides a composition comprising the MCNA as described above, encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels.

In some aspects, the present invention provides methods of delivering MCNA for in vivo protein production, comprising administering the MCNA as described above to a subject in need of delivery. In some embodiments, the MCNA is administered via a route of delivery selected from the group consisting of intravenous delivery, subcutaneous delivery, oral delivery, subdermal delivery, ocular delivery, intratracheal injection pulmonary delivery (e.g. nebulization), intramuscular delivery, intrathecal delivery, or intraarticular delivery.

It is to be understood that all embodiments as described above are applicable to all aspects of the present invention.

BRIEF DESCRIPTION OF THE DRAWING

The drawings are for illustration purposes only, not for limitation.

DEFINITIONS

Figure 1:
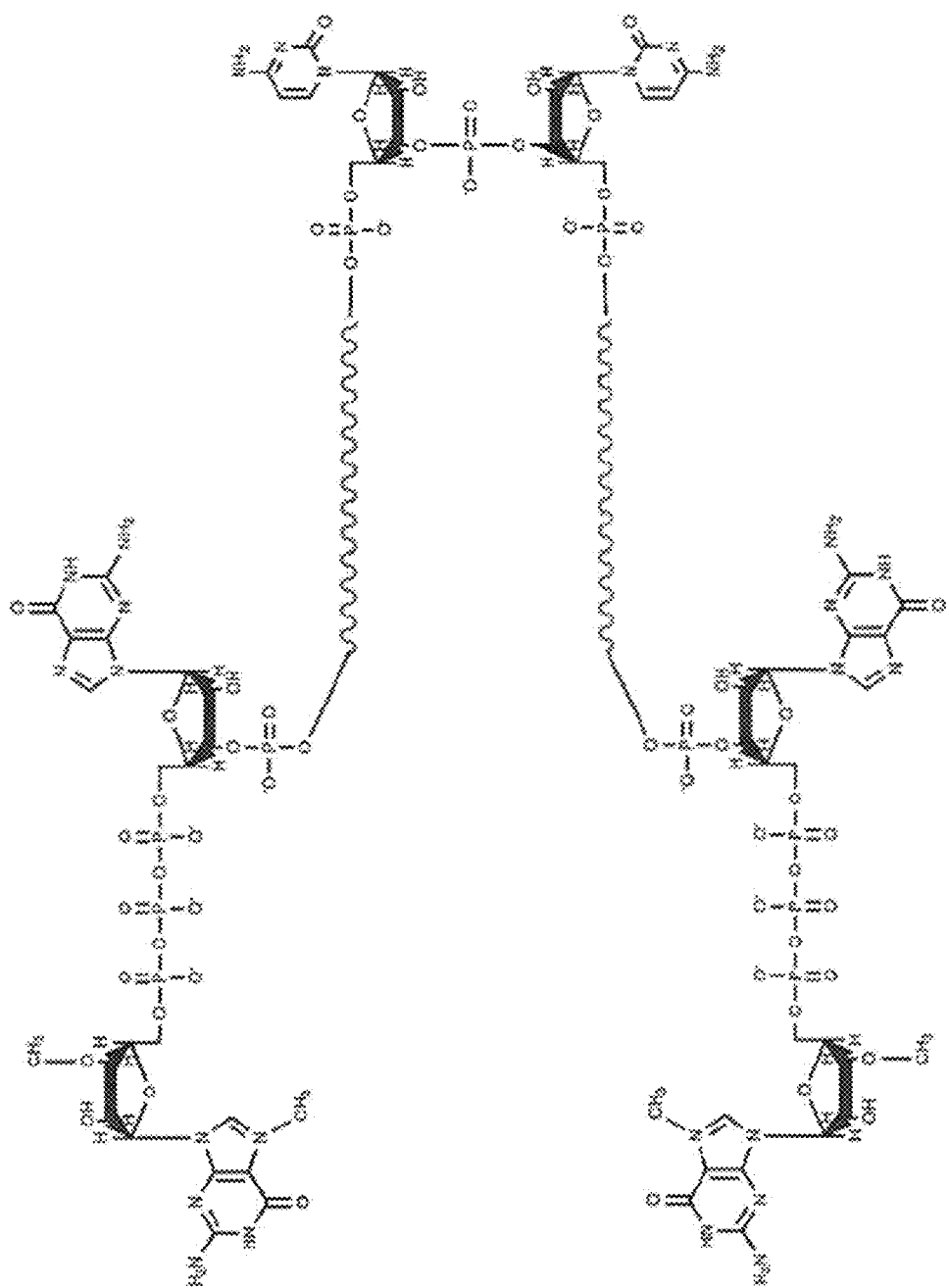
FIG. 1 shows an exemplary MCNA comprising two RNA species linked via a 3'-3' inverted RNA nucleotide dimer.
Figure 2:
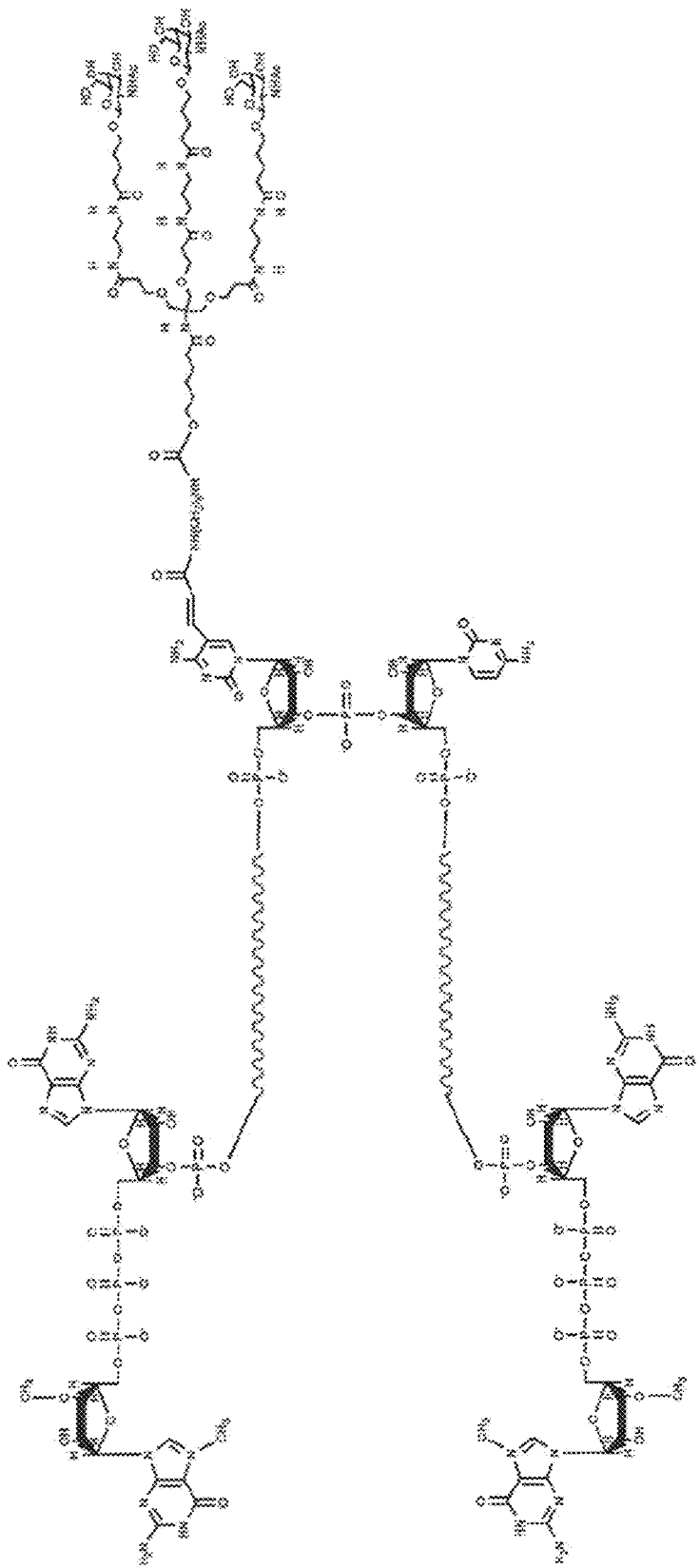
FIG. 2 shows an exemplary MCNA comprising two RNA species linked via a 3'-3' inverted RNA nucleotide dimer wherein the MCNA is functionalized with a tri-antennary GalNac targeting agent.
Figure 3:
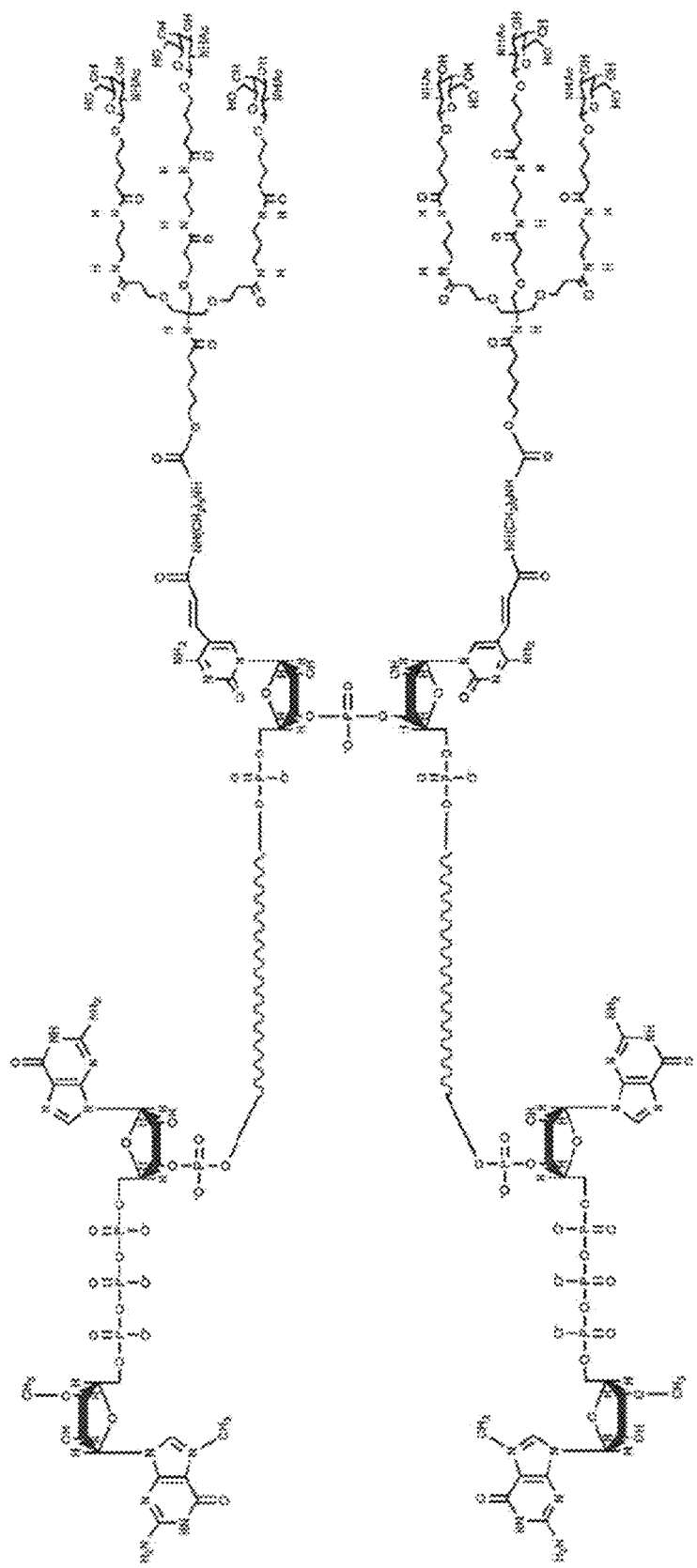
FIG. 3 shows an exemplary MCNA comprising two RNA species linked via a 3'-3' inverted RNA nucleotide dimer wherein the MCNA is functionalized with two tri-antennary GalNac targeting agent.
Figure 4:
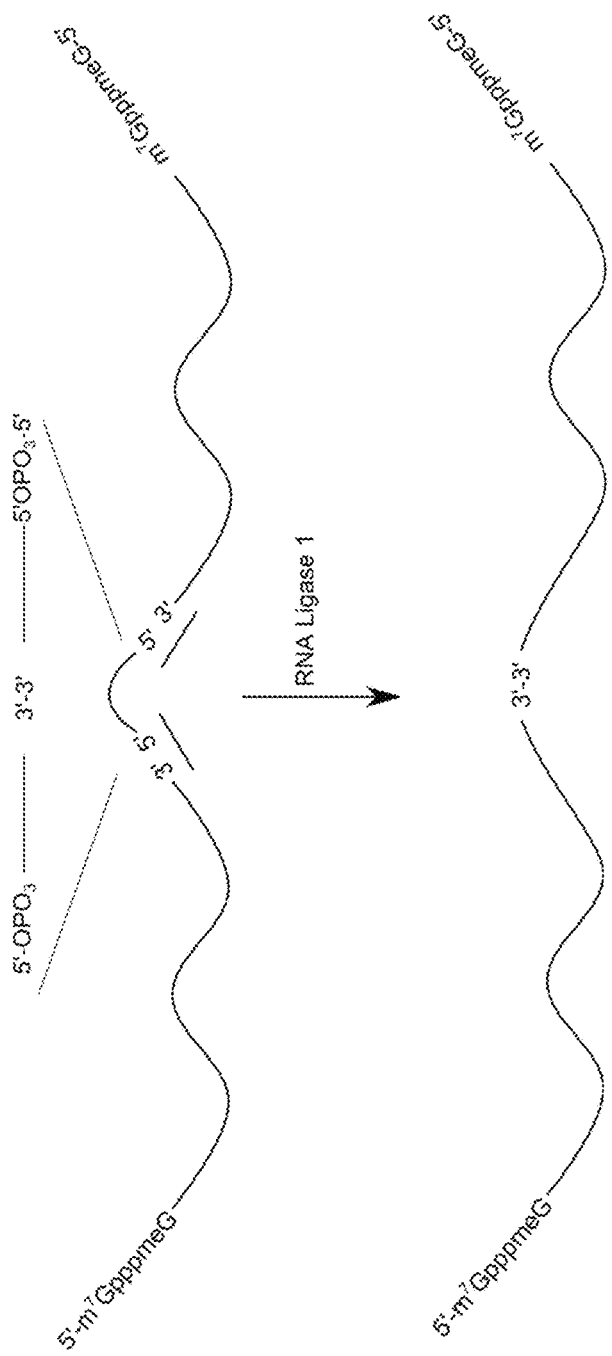
FIG. 4 shows a general scheme for synthesis of MCNA.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of MCNA encompasses situations in which an MCNA is delivered to a target tissue and the encoded protein is expressed and retained within the target tissue (also referred to as "local distribution" or "local delivery"), and situations in which an MCNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an MCNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" or "mRNA" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. A typical mRNA molecule has a 5' end and a 3' end. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods for synthesizing and compositions comprising multimeric coding nucleic acids (MCNA). In particular, the present invention provides MCNA compounds comprising two or more encoding polynucleotides linked via their 3' ends such that the MCNA compound comprises two or more 5' ends and methods of synthesizing the same. In some embodiments, each of the two or more encoding polynucleotides is a synthetic polyribonucleotide. In some embodiments, each of the two or more encoding polynucleotides is a synthetic polydeoxyribonucleotide. In some embodiments, a synthetic polyribonucleotide or polydeoxyribonucleotide of the invention codes for a polypeptide, protein, enzyme, antibody, or receptor. In some embodiments, the present invention provides a multimeric nucleic acid (MNA) comprising two or more polynucleotides linked via at least one 3' end linkage between two or more of the polynucleotides such that the MNA compound comprises two or more 5' ends. In some embodiments, one or more of the 5' ends is modified to facilitate stability of the MNA. In certain embodiments, the two or more polynucleotides linked via the at least one 3' end linkage each are non-coding nucleotides. In some embodiments, a MNA comprises a synthetic polyribonucleotide or polydeoxyribonucleotide that does not code for a polypeptide, protein, enzyme, antibody, or receptor. In some embodiments, MNA comprising a synthetic polyribonucleotide or polydeoxyribonucleotide inhibits gene expression. In some embodiments, a synthetic polyribonucleotide of the invention that inhibits gene expression is a small interfering ribonucleic acid (siRNA), a microRNA (miRNA), or a short hairpin RNA (shRNA).

While the administration of exogenous polynucleotides (e.g. DNA or RNA) represents a meaningful advancement for the treatment of diseases, the administration of such exogenous polynucleotides is often hampered by the limited stability of such polynucleotides, particularly following their in vivo administration. For example, following their administration to a subject, many polynucleotides may be subject to nuclease (e.g. exonuclease and/or endonuclease) degradation. Nuclease degradation may negatively influence the capability of a polynucleotide to reach a target cell or to be transcribed and/or translated, the result of which is to preclude the exogenous polynucleotide from exerting an intended therapeutic effect.

In some embodiments, the MCNA of the present invention exhibit increased in vivo stability compared to a single polynucleotide not linked to another polynucleotide by its 3' end (hereinafter "monomeric polynucleotide"). In some embodiments, the MCNA of the present invention, when delivered in vivo, lead to enhanced protein production compared to a monomeric polynucleotide encoding the same protein. In some embodiments, the MCNA of the present invention, when delivered to a subject, are tolerated better by the subject compared to a corresponding monomeric polynucleotide.

Multimeric Coding Nucleic Acids (MCNA)

In some embodiments, the present invention provides compositions comprising multimeric coding nucleic acids (MCNA) and methods for synthesizing the same. In particular, the present invention provides MCNA compounds comprising two or more encoding polynucleotides linked via their 3' ends such that the MCNA compound comprises two or more 5' ends and methods of synthesizing the same. In some embodiments, each of the two or more encoding polynucleotides is a synthetic polyribonucleotide. In some embodiments, each of the two or more encoding polynucleotides is a synthetic polydeoxyribonucleotide. In some embodiments, each of the two or more encoding polynucleotides is a synthetic polydeoxyribonucleotide or a polyribonucleotide. In some embodiments, each of the two or more encoding polynucleotides encodes a protein of interest. In some embodiments, each of the two or more encoding polynucleotides encodes a same protein. In some embodiments, each of the two or more encoding polynucleotides encodes a distinct protein. In some embodiments, each of the two or more encoding polynucleotides encoding a distinct protein are present in equal numbers. In some embodiments, each of the two or more encoding polynucleotides encoding a distinct protein are present in unequal numbers (e.g., 2 copies of a polynucleotide encoding protein of interest #1 and 1 copy of a polynucleotide encoding protein of interest #2). In some embodiments, a MCNA compound comprises three or more encoding polynucleotides. In some embodiments, a MCNA compound comprises four or more encoding polynucleotides. In some embodiments, a MCNA compound comprises five or more encoding polynucleotides.

In some embodiments, the present invention provides a multimeric nucleic acid (MNA) comprising two or more polynucleotides linked via at least one 3' end linkage between two or more of the polynucleotides such that the MNA compound comprises two or more 5' ends. In some embodiments, one or more of the 5' ends is modified to facilitate stability of the MNA. In certain embodiments, at least one of the two or more polynucleotides linked via the at least one 3' end linkage is an encoding polynucleotide and at least one of the two or more polynucleotides linked via the at least one 3' end linkage is a non-coding polynucleotide, thereby constituting a multimeric coding nucleic acid (MCNA). In certain embodiments, the encoding polynucleotide encodes a protein of interest and the non-coding polynucleotide inhibits gene expression (e.g., small interfering ribonucleic acid (siRNA), a microRNA (miRNA), or a short hairpin RNA (shRNA).

In some embodiments, a MCNA compound comprising two or more encoding polynucleotides encodes one or more chains of an antibody or antibody fragment. In some embodiments, the two or more encoding polynucleotides encode a heavy chain and light chain of an antibody. In some embodiments, the antibody is an intact immunoglobulin, (Fab)2, (Fab')2, Fab, Fab' or scFv. In some embodiments, the antibody is an IgG. In some embodiments, the antibody is selected from the group consisting of anti-CCL2, anti-lysyl oxidase-like-2 (LOXL2), anti-Flt-1, anti-TNF-α, anti-Interleukin-2Rα receptor (CD25), anti-TGFβ, anti-B-cell activating factor, anti-alpha-4 integrin, anti-BAGE, anti-β-catenin/m, anti-Bcr-abl, anti-CS, anti-CA125, anti-CAMEL, anti-CAP-1, anti-CASP-8, anti-CD4, anti-CD19, anti-CD20, anti-CD22, anti-CD25, anti-CDC27/m, anti-CD 30, anti-CD33, anti-CD52, anti-CD56, anti-CD80, anti-CDK4/m, anti-CEA, anti-CT, anti-CTL4, anti-Cyp-B, anti-DAM, anti-EGFR, anti-ErbB3, anti-ELF2M, anti-EMMPRIN, anti-Ep-Cam, anti-ETV6-AML1, anti-HER2, anti-G250, anti-GAGE, anti-GnT-V, anti-Gp100, anti-HAGE, anti-HER-2/neu, anti-HLA-A*0201-R170I, anti-IGF-1R, anti-IL-2R, anti-IL-S, anti-MC1R, anti-myosin/m, anti-MUC1, anti-MUM-1, -2, -3, anti-proteinase-3, anti-p190 minor bcr-abl, anti-Pml/RARa, anti-PRAMS, anti-PSA, anti-PSM, anti-PSMA, anti-RAGE, anti-RANKL, anti-RU1 or RU2, anti-SAGE, anti-SART-1 or anti-SART-3, anti-survivin, anti-TEL/AML1, anti-TPI/m, anti-TRP-1, anti-TRP-2, anti-TRP-2/INT2, and anti-VEGF or anti-VEGF receptor.

In some embodiments, a MCNA compound comprising two or more encoding polynucleotides encodes one or more nucleases. In some embodiments, each of the one or more nucleases is selected from the group comprising Cas9, zinc-finger nucleases (ZFN), TALEN, homing endonucleases, homing meganucleases, and combinations thereof. Exemplary nucleases include Afu Uracil-DNA Glycosylase (UDG), Tina Endonuclease III, Tth Endonuclease IV, Antarctic Thermolabile UDG, APE 1, Cas9 Nuclease NLS (*S. pyogenes*), Cas9 Nuclease (*S. pyogenes*), DNase I, Endonuclease IV, Endonuclease V, Endonuclease VIII, Exonuclease I, Exonuclease III (*E. coli*), Exonuclease T, Exonuclease V (RecBCD), Exonuclease VII, Exonuclease VIII (truncated), Fpg, hAAG, hOGG1, hSMUG1, Lambda Exonuclease, Micrococcal Nuclease, Mung Bean Nuclease, Nuclease BAL-31, RecA$_f$, RecJ$_f$, T4 PDG (T4 Endonuclease V), T5 Exonuclease, T7 Endonuclease I, T7 Exonuclease, Thermostable FEN1, Uracil Glycosylase Inhibitor (UGI). Exemplary homing nucleases include I-AabMI, I-Anil, I-Ceul, I-CkaMI, I-CpaMI, I-CreI, I-Dmol, I-GpeMI, I-Gpil, I-Gzel, I-GzeII, I-HjeMI, I-Ltrl, I-LtrWI, I-MpeMI, I-Msol, I-OnuI, I-PanMI, I-SceI, I-SmaMI, I-Vdi141I, PI-SceI, I-CreI (m), I-Msol (m), I-OnuI (E2), I-Anil/I-OnuI, I-Dmol/I-CreI, I-Gpil/I-OnuI, I-Gzel/I-PanMI, I-Ltrl/I-PanMI, I-OnuI/I-Ltrl, I-AaeMIP, I-ApaMIP, I-GzeMIIIP. I-NcrMIP, I-OsoMIIP, I-OsoMIP, I-PanMIIIP, I-PanMIIP, I-ScuMIIIP, I-ScuMIIP, I-ScuMIP, and I-ScuMIVP.

In some embodiments, a MCNA compound comprises two more more polynucleotides that include one, two, or more encoding polynucleotides, wherein each encoding polynucleotide comprises a polynucleotide portion that is an mRNA transcript for a gene and/or for a protein selected from Table 1, Table 2, Table 3, Table 4, Table 5 or Table 6.

TABLE 1

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; H1Fla; HIF3a; Met; HRG; Bcl2; PPARalpha; PPAR gamma; WT1 (Wilms Tumor); FGF Receptor Family members (5 members: 1, 2, 3, 4, 5); CDKN2a; APC; RB (retinoblastoma); MEN!; VHL; BRCA1; BRCA2; AR (Androgen Receptor); TSG101; IGF; IGF Receptor; Igf1 (4 variants); Igf2 (3 variants); Igf1 Receptor; Igf2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia Disorders | Neuregulinl (Nrgl); Erb4 (receptor for Neuregulin); Complexinl (Cplxl); Tphl Tryptophan hydroxylase; Tph2 Tryptophan hydroxylase 2; Neurexin 1; GSK3; GSK3a; GSK3b; 5-HTT (Slc6a4); COMT; DRD (Drdla); SLC6A3; DAOA; DTNBPl; Dao (Dao1) |

TABLE 1-continued

| DISEASE/DISORDERS | GENE(S) |
|---|---|
| Trinucleotide Repeat Disorders | HTT (Huntington's Dx); SBMA/SMAXl/AR (Kennedy's Dx); FXN/X25 (Friedrich's Ataxia); ATX3 (Machado-Joseph's Dx); ATXNl and ATXN2 (spinocerebellar ataxias); DMPK (myotonic dystrophy); Atrophin-1 and Atn1(DRPLA Dx); CBP (Creb-BP-global instability); VLDLR (Alzheimer's); Atxn7; Atxn10 |
| Fragile X Syndrome | FMR2; FXRl; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related Disorders | Prp |
| ALS | SOD1; ALS2; STEX; FUS; TARD BP; VEGF (VEGF-a; VEGF-b; VEGF-c) |
| Drug Addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-la; IL-lb); IL-13; IL-17 (IL-17a (CTLA8); IL-17b; IL-17c; IL-17d; IL-171); 11-23; Cx3crl; ptpn22; TNFa; NOD2/CARD15 for IBD; IL-6; IL-12 (IL-12a; IL-12b); CTLA4; Cx3cll |
| Parkinson's Disease | x-Synuclein; DJ-1; LRRK2; Parkin; PINK1 |

TABLE 2

| CELLULAR FUNCTION | GENES |
|---|---|
| Blood and coagulation diseases and disorders | Anemia (CDAN1, CDA1, RPS19, DBA, PKLR, PK1, NT5C3, UMPH1, PSNl, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor Hand factor H-like 1 (HF1, CFH, HUS); Factor V and Factor VIII (MCFD2); Factor VII deficiency (F7); Factor X deficiency (FlO); Factor XI deficiency (F11); Factor XII deficiency (F12, HAF); Factor XIIIA deficiency (F13Al, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCDl, FANCD2, FANCD, FACD, FAD, FANCE, FACE, FANCF, XRCC9, FANCG, BR1Pl, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, FSC, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TALl, TCL5, SCL, TAL2, FLT3, NBS1, NBS, ZNFN1Al, 1Kl, LYF1, HOXD4, HOX4B, BCR, CML, PHL, ALL, ARNT, KRAS2, RASK2, GMPS, AFlO, ARHGEF12, LARG, KIAA0382, CALM, CLTH, CEBPA, CEBP, CHIC2, BTL, FLT3, KIT, PBT, LPP, NPMl, NUP214, D9S46E, CAN, CAIN, RUNXl, CBFA2, AML1, WHSC1Ll, NSD3, FLT3, AF1Q, NPM1, NUMA1, ZNF145, PLZF, PML, MYL, STAT5B, AF1Q, CALM, CLTH, ARL11, ARLTS1, P2RX7, P2X7, BCR, CML, PHL, ALL, GRAF, NF1, VRNF, WSS, NFNS, PTPNll, PTP2C, SHP2, NS1, BCL2, CCND1, PRAD1, BCL1, TCRA, GATA1, GF1, ERYF1, NFE1, ABLl, NQO1, DIA4, NMOR1, NUP214, D9S46E, CAN, CAIN). |
| Inflammation and immune related diseases and disorders | AIDS (KIR3DL1, NKAT3, NKB1, AMB11, K1R3DS1, IFNG, CXCL12, SD F1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSFS, CD40LG, HIGM1, IGM, FOXP3, IPEX, AIID, XPID, PIDX, TNFRSF14B, TAC1); Inflammation (IL-10, IL-1 (IL-la, IL-lb), IL-13, IL-17 (IL-17a (CTLA8), IL-17b, IL-17c, IL-17d, IL-171), 11-23, Cx3crl, |

TABLE 2-continued

| CELLULAR FUNCTION | GENES |
|---|---|
| | ptpn22, TNFa, NOD2/CARD15 for IBD, IL-6, IL-12 (IL-12a, IL-12b), CTLA4, Cx3cll); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AX1N1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PAC1P1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), CONT, DRD (Drd1a), SLC6Aβ, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQPO, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, |

TABLE 2-continued

| CELLULAR FUNCTION | GENES |
|---|---|
| | AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |
| Epilepsy | NHLRC1, EPM2A, EPM2B |
| Duchenne muscular dystrophy | DMD, BMD |
| AIDS | KIR3DL1, NKAT3, NKB1, AMB11, KIR3DS1, IFNG, CDDCL12, SDF1 |
| Alpha 1-Antitrypsin Deficiency | SERPINA1 [serpin peptidase inhibitor, cladeA (alpha-1 antiproteinase, antitrypsin), member 1]; SERPINA2 [serpin peptidase inhibitor, cladeA (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, Glade A (alpha-1 antiproteinase, antitrypsin), member 7]; SERPINA6 (serpin peptidase inhibitor, cladeA (alpha-1 antiproteinase, antitrypsin), member 6) |

TABLE 3

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM!; ITGB7; YWHAZ; ILK; TP53; RAF!; IKBKG; RELB; DYRK1A; CDKNIA; ITGB1; MAP2K2; JAK1; AKT1; JAK2; PIK3Rl; CHUK; PDPK1; PPP2R5C; CTNNB1; MAP2K1; NFKB1; PAK3; ITGB3; CCND1; GSK3A; FRAP!; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKC1; PTK2; FOS; RPS6KA4; PIK3CB; PPP2R1A; PIK3C3; MAPK8; MAPK3; ITGA1; ETSI; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF!; FYN; DYRK1A; ITGB1; MAP2K2; PAK4; PIK3Rl; STAT3; PPP2R5C; MAP2Kl; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPKI; SMAD3; AKT2; IKBKB; NCOR2; UBE21; PIK3CA; CREBI; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; WN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |

TABLE 3-continued

| CELLULAR FUNCTION | GENES |
|---|---|
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNKIA1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; |

TABLE 3-continued

| CELLULAR FUNCTION | GENES |
|---|---|
| p53 Signaling | RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM! 7; AKT1; PIK3Rl; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3Rl; PDPK1; MAP2K1; GSK3A; FRAP1; CRKL; GSK3B; AKT3; FOXO1; SGK; RPS6KB1 |

TABLE 3-continued

| CELLULAR FUNCTION | GENES |
|---|---|
| IL-6 Signaling | HSPB1; TRAF6; MAPKAPK2; ELK1; MAPK1; PTPN11; IKBKB; FOS; NFKB2: MAP3K14; MAPKS; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2KI; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; REBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2Kl; NFKB1; JUN; IL1R1; HSP90AA1 |
| Fc Epsilon R1 Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3Rl; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |

TABLE 3-continued

| CELLULAR FUNCTION | GENES |
|---|---|
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GN-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; LK1; AKT2; T2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| P38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |

TABLE 3-continued

| CELLULAR FUNCTION | GENES |
|---|---|
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |

TABLE 3-continued

| CELLULAR FUNCTION | GENES |
| --- | --- |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2); Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

TABLE 4

| INDICATION(S) | THERAPEUTIC PROTEIN |
| --- | --- |
| Maple syrup urine disease | 3-methyl-2-oxobutanoate dehydrogenase |
| Medium-chain acyl-CoA dehydrogenase deficiency | Acyl-CoA dehydrogenase |

TABLE 4-continued

| INDICATION(S) | THERAPEUTIC PROTEIN |
|---|---|
| Alpha 1-antitrypsin deficiency | Alpha 1 protease inhibitor |
| Pompe disease | Alpha glucosidase |
| Paroxysmal nocturnal hemoglobinuria | Anti-complement factor C5 Mab |
| Familial dysbetalipoproteinemia | Apolipoprotein E |
| Argininemia | Arginase |
| Argininosuccinic acidemia | Argininosuccinate lyase |
| Citrullinemia, type I | Argininosuccinate synthase |
| Short-chain acyl-CoA dehydrogenase deficiency | Butyryl-CoA dehydrogenase |
| Hereditary angioedema | C1 esterase inhibitor |
| Carbamylphosphate synthetase deficiency | Carbamylphosphate synthetase |
| Cystic fibrosis | CFTR |
| Hemophilia B | Factor IX |
| Hemophilia A, Hemophilia B | Factor VII |
| Hemophilia A | Factor VIII |
| Classical galactosemia | Galactose-1-phosphate uridylyltransferase |
| von Gierke's disease | Glucose-6-phosphatase |
| Glutaric acidemia, type I | Glutaryl-CoA dehydrogenase |
| Isovaleric aciduria | Isovaleric acid CoA dehydrogenase deficiency |
| Homozygous familial hypercholesterolemia | LDL receptor |
| Long-chain 3-OH acyl-CoA dehydrogenase deficiency | Long-chain-3-hydroxyacyl-CoA dehydrogenase |
| Very long-chain acyl-CoA dehydrogenase deficiency | Long-chain-acyl-CoA dehydrogenase |
| Methylmalonyl-CoA mutase deficiency | Methylmalonyl-CoA mutase |
| Ornithine transcarbamylase deficiency | Ornithine transcarbamylase |
| Phenylketonuria | Phenylalanine hydroxylase |
| Acute intermittent porphyria | Porphobilinogen deaminase |
| Propionic acidemia | Propionyl-CoA carboxylase |
| Hyperoxaluria, type I | Serine-pyruvate aminotransferase |
| Crigler-Najjar syndrome | UDP-glucuronosyltransferase |
| Non-Hodgkin lymphoma | Anti-CD20 mAb |
| Allergic asthma | Anti-IgE mAb |
| Psoriasis | Anti-IL-12 & IL-23 mAb |
| Rheumatoid arthritis | Anti-interleukin-6 (IL-6) mAb |
| Anemia | Erythropoietin |
| Rheumatoid arthritis | T-cell costimulation blocker |
| Rheumatoid arthritis | TNF-alpha inhibitors (including anti-TNF-alpha mAb) |
| Gout | Urate oxidase |
| Familial chylomicronemia | Lipoprotein lipase |
| Melanoma | Anti-CTLA4 mAb |
| Head and neck cancer, Metastatic colorectal cancer | Anti-EGFr mAb |
| HER2+ breast cancer, gastric cancer | Anti-HER2 mAb |
| Metastatic colorectal cancer, NSCLC, others | Anti-VEGF mAb |
| Blepharospasm, Cervical dystonia, Chronic migraine, more | Botulinum toxin |
| Female infertility | Follicle stimulating hormone |
| Type 2 diabetes mellitus | Glucagon-like peptide 1 (GLP-1) agonist |
| Growth hormone deficiency | Growth hormone 1/Growth hormone 2 |
| Type 2 diabetes mellitus | Insulin |
| Hypoparathyroidism | Parathyroid hormone |
| Asthma | SERCA2 |
| Asthma | FoxP3 |
| Surfactant Deficiency | Pulmonary surfactants (SFTPA1, SFTPB, SFTPC, SFTPD) |
| Pulmonary Alveolar proteinosis | GM-CSF Receptor (CSF2RA, CSF2RB) |
| alport syndrome | Col4A5 |
| Stargardt's Disease | ABCA4 |
| Retinitis pigmentosa | Rhodopsins |
| Adrenoleukodystrophy | ABCD1 |
| Adenosine deaminase deficiency | Adenosine deaminase |
| Familial adenomatous polyposis | APC |
| Autosomal recessive polycystic kidney disease | ARPKD |
| Metachromatic leukodystrophy | Arylsulfatase A |
| Batten disease | Battenin + others |
| Beta-thalassemia | Beta globin |
| X-linked agammaglobulinemia | Bruton's tyrosine kinase |
| Becker muscular dystrophy | Dystrophin |
| Duchenne muscular dystrophy | Dystrophin |
| Marfan syndrome | FBN1 |

TABLE 4-continued

| INDICATION(S) | THERAPEUTIC PROTEIN |
|---|---|
| Fragile X syndrome | FMRP |
| Krabbe disease | Galactocerebrosidase |
| Sickle cell disease | Hemoglobin |
| Sanfilippo syndrome, type A (MPS IIIA) | Heparan N-sulfatase |
| GM2 gangliosidosis | HEXA, HEXB |
| Hemachromatosis | HFE protein |
| Huntington disease | Huntingtin |
| Lesch-Nyhan syndrome | Hypoxanthine phosphoribosyltransferase 1 |
| McArdle disease | Muscle glycogen phosphorylase |
| Sanfilippo syndrome, type B (MPS IIIB) | N-acetyl-alpha-D-glucosaminidase |
| Leber's hereditary optic neuropathy | NADH dehydrogenase |
| Neurofibromatosis, type 1 | NF-1 |
| Niemann Pick disease, type C | NPC1 |
| Alpers' disease | POLG |
| Von Hippel-Lindau disease | pVHL |
| Paget disease of bone | Sequestosome 1 |
| Carnitine uptake defect | SLC22A5 |
| Cystinuria | SLC7A9 |
| Niemann Pick disease, type A/B | SMPD1 |
| Spinal muscular atrophy | Survival motor neuron protein |
| Li-Fraumeni syndrome | TP53 |
| Fabry disease | Alpha galactosidase |
| Alpha-mannosidosis | Alpha-D-mannosidase |
| Hurler syndrome (MPS I) | Alpha-L iduronidase |
| Hemolytic uremic syndrome | Anti-complement factor C5 mAb |
| Morquio syndrome, type B (MPS IVB) | Beta-galactosidase |
| Multiple carboxylase deficiency | Biotin-methylcrotonoyl-CoA-carboxylase ligase |
| Homocystinuria | Cystathionine beta-synthase |
| Cystinosis | Cystinosin |
| Cystic fibrosis | Deoxyribonuclease I |
| Erythropoietic protoporphyria | Ferrochelatase |
| Tyrosinemia, type I | Fumarylacetoacetase |
| GALK deficiency | Galactokinase |
| Morquio syndrome, type A (MPS IVA) | Galactose 6-sulfate sulfatase |
| GALE deficiency | Galactose epimerase |
| Gaucher disease | Glucocerebrosidase |
| Alkaptonuria | Homogentisate 1,2-dioxygenase |
| Hunter syndrome (MPS II) | Iduronate-2-sulfatase |
| Lysosomal acid lipase deficiency | Lysosomal acid lipase |
| Hypermethioninemia | Methionine adenosyltransferase |
| 3-Methylcrotonyl-CoA carboxylase deficiency | Methylcrotonoyl-CoA carboxylase |
| 3-Methylglutaconic aciduria | Methylglutaconyl-CoA hydratase |
| Maroteaux-Lamy syndrome (MPS VI) | N-acetylgalactosamine 4-sulfatase |
| Familial mediterranean fever | Pyrin (MEFV) |
| Tetrahydrobiopterin-deficient hyperphenylalaninemia | Tetrahydrobiopterin |
| Juvenile rheumatoid arthritis | TNF-alpha inhibitors |
| Psoriatic arthritis | TNF-alpha inhibitors |
| Hypophosphatasia | TNSALP |
| Gilbert syndrome | UDP-glucuronosyltransferase |
| Porphyria cutanea tarda | Uroporphyrinogen decarboxylase |
| Wilson disease | Wilson disease protein |
| Systemic lupus erythematosus | Anti-BAFF |
| Osteoporosis | Anti-RANKL mAb |
| Multiple sclerosis | Anti-VLA-4 mAb |
| Neutropenia | G-CSF |
| Immunoglobulin deficiency | Immunoglobulin |
| Primary humoral immune deficiencies (e.g., CVID) | Immunoglobulin |
| Infectious diseases vaccines | Infectious antigen |
| Hepatitis B, Hepatitis C | Interferon alpha |
| Multiple sclerosis | Interferon beta |
| Chronic immune thrombocytopenia | Thrombopoietin |
| Ehlers-Danlos syndrome, type 1 | Proteins encoded by ADAMTS2, B3GALT6, B4GALT7, CHST14, COL1A1, COL1A2, COL3A1, COL5A1, COL5A2, DSE, FKBP14, PLOD1, PRDM5, SLC39A13, TNXB, and ZNF469 |
| Stickler syndrome | Proteins encoded by COL11A1, COL11A2, COL2A1, COL9A1, COL9A2, and COL9A3 |

TABLE 4-continued

| INDICATION(S) | THERAPEUTIC PROTEIN |
|---|---|
| Hereditary hemorrhagic telangiectasia | Proteins encoded by ACVRL1, ENG, and SMAD4 |
| Hereditary spherocytosis | Proteins encoded by ANK1, EPB42, SLC4A1, SPTA1 and SPTB |
| Brugada syndrome | Proteins encoded by CACNA1C, CACNA2D1, CACNB2, GPD1L, HCN4, KCND3, KCNE3, KCNE5, KCNJ8, RANGRF, SCN1B, SCN2B, SCN3B, SCN5A, SLMAP, and TRPM4 |
| Osteopetrosis | Proteins encoded by CA2, CLCN7, IKBKG, ITGB3, OSTM1, PLEKHM1, TCIRG1, TNFRSF11A, and TNFSF11 |
| Mitochondrial oxidative phosphorylation disorders | Proteins encoded by FBXL4, and NDUFB9 |

TABLE 5

| INDICATION(S) | THERAPEUTIC PROTEIN | GENE |
|---|---|---|
| Achromatopsia type 2 | Cyclic nucleotide-gated channel, α3 subunit | CNGA3 |
| Achromatopsia type 3 | Cyclic nucleotide-gated channel, β3 subunit | CNGB3 |
| Aland Island eye disease | Cav1.4: calcium channel, voltage-gated, L type, α1F subunit | CACNA1F |
| Andersen-Tawil syndrome | Kir2.1: potassium channel, inwardly-rectifying, subfamily J, member 2 | KCNJ2 |
| Benign familial infantile epilepsy | Nav2.1: sodium channel, voltage-gated, type II, α subunit | SCN2A |
|  | Kv7.2: potassium channel, voltage-gated, KQT-like subfamily, member 2 | KCNQ2 |
|  | Kv7.3: potassium channel, voltage-gated, KQT-like subfamily, members | KCNQ3 |
| Bestrophinopathy, autosomal-recessive | Bestrophin 1 | BEST1 |
| Central core disease | RyR1: ryanodine receptor 1 | RYR1 |
| Charcot-Marie-Tooth disease type 2C | Transient receptor potential cation channel, subfamily V, member 4 | TRPV4 |
| Childhood absence epilepsy | γ-aminobutyric acid A receptor, α1 subunit | GABRA1 |
|  | γ-aminobutyric acid A receptor, α6 subunit | GABRA6 |
|  | γ-aminobutyric acid A receptor, β3 subunit | GABRB3 |
|  | γ-aminobutync acid A receptor, γ2 subunit | GABRG2 |
|  | Cav3.2: calcium channel, voltage-gated, T type, α1H subunit | CACNA1H |
| Cognitive impairment with or without cerebellar ataxia | Nav1.6: sodium channel, voltage-gated, type VIM, α subunit | SCN8A |
| Cone-rod dystropy, X-linked, type 3 | Cav1.4: calcium channel, voltage-gated, L type, α1F subunit | CACNA1F |
| Congenital distal spinal muscular atrophy | Transient receptor potential cation channel, subfamily V, member 4 | TRPV4 |
| Congenital indifference to pain, autosomal-recessive | Nav1.7: Sodium channel, voltage-gated, type IX, α subunit | SCN9A |
| Congenital myasthenic syndrome | Cholinergic receptor, muscle nicotinic, α1 subunit | CHRNA1 |
|  | Cholinergic receptor, muscle nicotinic, β1 subunit | CHRNB1 |
|  | Cholinergic receptor, muscle nicotinic, δ subunit | CHRND |
|  | Cholinergic receptor, muscle nicotinic, ε subunit | CHRNE |
|  | Nav1.4: sodium channel, voltage-gated, type IV, α subunit | SCN4A |
| Congenital stationary night blindness type 1C | Transient receptor potential cation channel, subfamily M, member 1 | TRPM1 |
| Congenital stationary night blindness type 2A | Cav1.4: calcium channel, voltage-gated, L type, α1F subunit | CACNA1F |
| Deafness, autosomal-dominant, type 2A | Kv7.4: potassium channel, voltage-gated, KQT-like subfamily, member 4 | KCNQ4 |

TABLE 5-continued

| INDICATION(S) | THERAPEUTIC PROTEIN | GENE |
|---|---|---|
| Deafness, autosomal-recessive, type 4, with enlarged vestibular aqueduct | Kir4.1: potassium channel, inwardly-rectifying, subfamily J, member 10 | KCNJ10 |
| Dravet syndrome | Nav1.1: sodium channel, voltage-gated, type I, α subunit | SCN1A |
| | γ-aminobutyric acid A receptor, γ2 subunit | GABRG2 |
| Early infantile epileptic encephalopathy type 7 | Kv7.2: potassium channel, voltage-gated, KQT-like subfamily, member 2 | KCNQ2 |
| Early infantile epileptic encephalopathy type 11 | Nav2.1: sodium channel, voltage-gated, type II, α subunit | SCN2A |
| Early infantile epileptic encephalopathy type 13 | Nav1.6: sodium channel, voltage-gated, type VIII, α subunit | SCN8A |
| Early infantile epileptic encephalopathy type 14 | KCa4.1: potassium channel, subfamily T, member 1 | KCNT1 |
| EAST/SeSAME syndrome | Kir4.1: potassium channel, inwardly-rectifying, subfamily J, member 10 | KCNJ10 |
| Episodic ataxia type 1 | Kv1.1: potassium channel, voltage-gated, shaker-related subfamily, member 1 | KCNA1 |
| Episodic ataxia type 2 | Cav2.1: calcium channel, voltage-gated, P/Q type, α1A subunit | CACNA1A |
| Episodic ataxia type 5 | Cavβ4: calcium channel, voltage-gated, β4 subunit | CACNB4 |
| Familial episodic pain syndrome | Transient receptor potential cation channel, subfamily A, member 1 | TRPA1 |
| Familial hemiplegic migraine type 1 | Cav2.1: calcium channel, voltage-gated, P/Q type, α1A subunit | CACNA1A |
| Familial hemiplegic migraine type 3 | Nav1.1: sodium channel, voltage-gated, type I, α subunit | SCN1A |
| Generalized epilepsy with febrile seizures plus (GEFS+) | Navβ1: sodium channel, voltage-gated, type I, β subunit | SCN1B |
| | Nav1.1: sodium channel, voltage-gated, type I, α subunit | SCN1A |
| | γ-aminobutyric acid A receptor, γ2 subunit | GABRG2 |
| Generalized epilepsy with paroxysmal dyskinesia | KCa1.1: potassium channel, calcium-activated, large conductance, subfamily M, α1 subunit | KCNMA1 |
| Hereditary hyperekplexia | Glycine receptor, α1 subunit | GLRA1 |
| | Glycine receptor, β subunit | GLRB |
| Hyperkalemic periodic paralysis | Nav1.4: sodium channel, voltage-gated, type IV, α subunit | SCN4A |
| Hypokalemic periodic paralysis type 1 | Cav1.1: calcium channel, voltage-gated, L type, α1S subunit | CACNA1S |
| Hypokalemic periodic paralysis type 2 | Nav1.4: sodium channel, voltage-gated, type IV, α subunit | SCN4A |
| Juvenile macular degeneration | Cyclic nucleotide-gated channel, β3 subunit | CNGB3 |
| Juvenile myoclonic epilepsy | γ-aminobutyric acid A receptor, α1 subunit | GABRA1 |
| | Cavβ4: calcium channel, voltage-gated, β4 subunit | CACNB4 |
| Malignant hyperthermia susceptibility | RyR1: ryanodine receptor 1 | RYR1 |
| | Cav1.1: calcium channel, voltage-gated, L type, α1S subunit | CACNA1S |
| Mucolipidosis type IV | TRPML1/mucolipin 1 | MCOLN1 |
| Multiple pterygium syndrome, lethal type | Cholinergic receptor, muscle nicotinic, α1 subunit | CHRNA1 |
| Multiple pterygium syndrome, nonlethal type (Escobar variant) | Cholinergic receptor, muscle nicotinic, δ subunit | CHRND |
| | Cholinergic receptor, muscle nicotinic, γ subunit | CHRNG |
| Myotonia congenita, autosomal-dominant (Thomsen disease) | ClC-1: chloride channel 1, voltage-gated | CLCN1 |
| Myotonia congenita, autosomal-recessive (Becker disease) | ClC-1: chloride channel 1, voltage-gated | CLCN1 |
| Nocturnal frontal lobe epilepsy type 1 | Cholinergic receptor, neuronal nicotinic, α4 subunit | CHRNA4 |
| Nocturnal frontal lobe epilepsy type 3 | Cholinergic receptor, neuronal nicotinic, β2 subunit | CHRNB2 |
| Nocturnal frontal lobe epilepsy type 4 | Cholinergic receptor, neuronal nicotinic, α2 subunit | CHRNA2 |

TABLE 5-continued

| INDICATION(S) | THERAPEUTIC PROTEIN | GENE |
|---|---|---|
| Nocturnal frontal lobe epilepsy type 5 | KCa4.1: potassium channel, subfamily T, member 1 | KCNT1 |
| Paramyotonia congenita | Nav1.4: sodium channel, voltage-gated, type IV, α subunit | SCN4A |
| Paroxysmal extreme pain disorder | Nav1.7: Sodium channel, voltage-gated, type IX, α subunit | SCN9A |
| Potassium-aggravated myotonia | Nav1.4: sodium channel, voltage-gated, type IV, α subunit | SCN4A |
| Primary erythermalgia | Nav1.7: sodium channel, voltage-gated, type IX, α subunit | SCN9A |
| Retinitis pigmentosa type 45, autosomal-recessive | Cyclic nucleotide-gated channel, β1 subunit | CNGB1 |
| Retinitis pigmentosa type 49, autosomal-recessive | Cyclic nucleotide-gated channel, α1 subunit | CNGA1 |
| Retinitis pigmentosa type 50, autosomal-dominant | Bestrophin 1 | BEST1 |
| Scapuloperoneal spinal muscular atrophy | Transient receptor potential cation channel, subfamily V, member 4 | TRPV4 |
| Small fiber neuropathy | Nav1.7: sodium channel, voltage-gated, type IX, α subunit | SCN9A |
| Spinocerebellar ataxia type 6 | Cav2.1: calcium channel, voltage-gated, P/Q type, α1A subunit | CACNA1A |
| Spinocerebellar ataxia type 13 | Kv3.3: potassium channel, voltage-gated, Shaw-related subfamily, members | KCNC3 |
| Vitelliform macular dystrophy | Bestrophin 1 | BEST1 |
| Vitreoretinochoroidopathy | Bestrophin 1 | BEST1 |

TABLE 6

Secreted Proteins

| Uniprot ID | Protein Name | Gene Name |
|---|---|---|
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |

TABLE 6-continued

Secreted Proteins

| Uniprot ID | Protein Name | Gene Name |
|---|---|---|
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (*S. cerevisiae*), isoform CRA_a | SEC11L3 |
| B4DJF9 | Protein Wnt | WNT4 |
| B4DUL4 | SEC11-like 1 (*S. cerevisiae*), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |

TABLE 6-continued

Secreted Proteins

| Uniprot ID | Protein Name | Gene Name |
| --- | --- | --- |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |

TABLE 6-continued

Secreted Proteins

| Uniprot ID | Protein Name | Gene Name |
|---|---|---|
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |

TABLE 6-continued

Secreted Proteins

| Uniprot ID | Protein Name | Gene Name |
|---|---|---|
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |

TABLE 6-continued

Secreted Proteins

| Uniprot ID | Protein Name | Gene Name |
|---|---|---|
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |

TABLE 6-continued

Secreted Proteins

| Uniprot ID | Protein Name | Gene Name |
| --- | --- | --- |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |

TABLE 6-continued

Secreted Proteins

| Uniprot ID | Protein Name | Gene Name |
|---|---|---|
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |

TABLE 6-continued

Secreted Proteins

| Uniprot ID | Protein Name | Gene Name |
| --- | --- | --- |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |

TABLE 6-continued

Secreted Proteins

| Uniprot ID | Protein Name | Gene Name |
| --- | --- | --- |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |

TABLE 6-continued

Secreted Proteins

| Uniprot ID | Protein Name | Gene Name |
|---|---|---|
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |

TABLE 6-continued

Secreted Proteins

| Uniprot ID | Protein Name | Gene Name |
|---|---|---|
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |

TABLE 6-continued

Secreted Proteins

| Uniprot ID | Protein Name | Gene Name |
|---|---|---|
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |

TABLE 6-continued

Secreted Proteins

| Uniprot ID | Protein Name | Gene Name |
| --- | --- | --- |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1(XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |

TABLE 6-continued

Secreted Proteins

| Uniprot ID | Protein Name | Gene Name |
| --- | --- | --- |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |

TABLE 6-continued

Secreted Proteins

| Uniprot ID | Protein Name | Gene Name |
|---|---|---|
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |

TABLE 6-continued

Secreted Proteins

| Uniprot ID | Protein Name | Gene Name |
| --- | --- | --- |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |

TABLE 6-continued

Secreted Proteins

| Uniprot ID | Protein Name | Gene Name |
|---|---|---|
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroadherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |

TABLE 6-continued

Secreted Proteins

| Uniprot ID | Protein Name | Gene Name |
|---|---|---|
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q765I0 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |

TABLE 6-continued

Secreted Proteins

| Uniprot ID | Protein Name | Gene Name |
|---|---|---|
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |

TABLE 6-continued

Secreted Proteins

| Uniprot ID | Protein Name | Gene Name |
| --- | --- | --- |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |

TABLE 6-continued

Secreted Proteins

| Uniprot ID | Protein Name | Gene Name |
|---|---|---|
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCH |
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |

TABLE 6-continued

Secreted Proteins

| Uniprot ID | Protein Name | Gene Name |
| --- | --- | --- |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |

TABLE 6-continued

Secreted Proteins

| Uniprot ID | Protein Name | Gene Name |
|---|---|---|
| Q9BT56 | Spexin | C12orf39 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |

TABLE 6-continued

Secreted Proteins

| Uniprot ID | Protein Name | Gene Name |
|---|---|---|
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |

TABLE 6-continued

Secreted Proteins

| Uniprot ID | Protein Name | Gene Name |
|---|---|---|
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |

TABLE 6-continued

Secreted Proteins

| Uniprot ID | Protein Name | Gene Name |
|---|---|---|
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In one set of embodiments, the MCNA compound comprises two encoding polynucleotides. For example, the MCNA compound may be a palindromic coding nucleic acid (PCNA) having two encoding polynucleotides each having a polynucleotide portion that codes for the same protein.

In some embodiments, a MCNA compound comprises an encoding polynucleotide that encodes Cystic Fibrosis Transmembrane Conductance Regulator (hCFTR) mRNA, linked to a non-coding polynucleotide via a 3' end linkage between the polynucleotides. In some embodiments, a MCNA compound comprises two or more encoding polynucleotides linked via a 3' end linkage between the polynucleotides such that the MCNA compound comprises two or more 5' ends, wherein at least one of the encoding polynucleotides encodes hCFTR. In some embodiments, a MCNA compound is a palindromic coding nucleic acid (PCNA) comprising two encoding polynucleotides linked via a 3' end linkage between the polynucleotides such that the MCNA compound comprises two or more 5' ends, wherein each encoding polynucleotide codes for hCFTR. In some embodiments, a MCNA compound comprises two or more polynucleotides linked via a 3' end linkage between the polynucleotides such that the MCNA compound comprises two or more 5' ends, wherein at least one polynucleotide is an encoding polynucleotide that encodes hCFTR and at least one polynucleotide acts as a protecting group.

In some embodiments, a MCNA compound comprises an encoding polynucleotide that encodes human phenylalanine hydroxylase (hPAH) mRNA, linked to a non-coding polynucleotide via a 3' end linkage between the polynucleotides. In some embodiments, a MCNA compound comprises two or more encoding polynucleotides linked via a 3' end linkage between the polynucleotides such that the MCNA compound comprises two or more 5' ends, wherein at least one of the encoding polynucleotides encodes hPAH. In some embodiments, a MCNA compound is a palindromic coding nucleic acid (PCNA) comprising two encoding polynucleotides linked via a 3' end linkage between the polynucleotides such that the MCNA compound comprises two or more 5' ends, wherein each encoding polynucleotide codes for hPAH. In some embodiments, a MCNA compound comprises two or more polynucleotides linked via a 3' end linkage between the polynucleotides such that the MCNA compound comprises two or more 5' ends, wherein at least one polynucleotide is an encoding polynucleotide that encodes hPAH and at least one polynucleotide acts as a protecting group.

In some embodiments, a MCNA compound comprises an encoding polynucleotide that encodes human Ornithine transcarbamylase (hOTC) mRNA, linked to a non-coding polynucleotide via a 3' end linkage between the polynucleotides. In some embodiments, a MCNA compound comprises two or more encoding polynucleotides linked via a 3' end linkage between the polynucleotides such that the MCNA compound comprises two or more 5' ends, wherein at least one of the encoding polynucleotides encodes hOTC. In some embodiments, a MCNA compound is a palindromic coding nucleic acid (PCNA) comprising two encoding polynucleotides linked via a 3' end linkage between the polynucleotides such that the MCNA compound comprises two or more 5' ends, wherein each polynucleotide codes for hOTC. In some embodiments, a MCNA compound comprises two or more polynucleotides linked via a 3' end linkage between the polynucleotides such that the MCNA compound comprises two or more 5' ends, wherein at least one polynucleotide is an encoding polynucleotide that encodes hOTC and at least one polynucleotide acts as a protecting group.

Bridge (w/3'-3' Linkage)

In some embodiments, a MCNA compound comprises two or more polynucleotides wherein the 3' ends of each polynucleotide are linked via an oligonucleotide bridge (also "bridging oligonucleotide" or "bridging olio") comprising a 3'-3' inverted phosphodiester linkage. In some embodiments, the oligonucleotide bridge comprises modified nucleotides. In some embodiments, the oligonucleotide bridge comprises 2'-O-methyl RNA. In some embodiments, the oligonucleotide bridge comprises DNA. In some embodiments, the oligonucleotide bridge is between 2 and 1000 nucleotides in length. In some embodiments, the oligonucleotide bridge comprises one or more active moieties that are bound to the bridge by covalent links. In some embodiments, an active moiety is a targeting group, peptide, contrast agent, small molecule, protein, DNA and/or RNA. In some embodiments, an active moiety binds a receptor ligand for a cell surface receptor. In some embodiments, the active moiety is one or more tri-antennary GalNac targeting agents.

MCNA Synthesis

In some embodiments, the present invention provides methods of synthesizing MCNA. In some embodiments, the synthesis of MCNA comprises ligating two or more polynucleotides such that the 3' end of each polynucleotide is ligated to the 5' end of an oligonucleotide bridge, wherein the oligonucleotide bridge comprises two 5' ends and an internal 3'-3' inverted phosphodiester linkage. In some embodiments, the method of synthesizing MCNA comprises the use of oligonucleotide splints complementary to regions of the two or more polynucleotides such that a ligase can join each polynucleotide to a 5' end of an oligonucleotide bridge. In some embodiments, oligonucleotide splints are complementary to regions of the two or more polynucleotides such that a ligase joins perfect ends of each polynucleotide to a 5' end of an oligonucleotide bridge. In some embodiments, oligonucleotide splints are complementary to regions of the two or more polynucleotides such that a ligase joins the 3' end of each polynucleotide to a 5' end of an oligonucleotide bridge. In some embodiments, an oligonucleotide splint comprises DNA. In some embodiments, a ligase is RNA Ligase. In some embodiments, a ligase is T4 RNA Ligase 1. In some embodiments, a ligase is T4 RNA Ligase 2.

In some embodiments, the molar ratio of polynucleotide to oligonucleotide bridge to oligonucleotide splint when synthesizing MCNA is 2:1:2. In some embodiments, the molar ratio of polynucleotide to oligonucleotide bridge when synthesizing MCNA is 2:1. In some embodiments, the molar ratio of polynucleotide to oligonucleotide splint when synthesizing MCNA is 2:2. In some embodiments, synthesis of MCNA further comprises PEG.

In some embodiments, MCNA can be prepared by splint ligation of the 3' end of two copies of an RNA to the 5' ends of a single oligonucleotide containing two 5' ends and a linked 3'-3' phosphodiester bond within the sequence. Briefly, a 5'-capped RNA containing a 5' untranslated region (UTR) and a 3' UTR flanking an RNA coding sequence is transcribed using T7 RNA polymerase, enzymatically capped to contain a 5'-Cap 1 structure and purified. This transcript is then ligated in a single step to a "bridge" oligonucleotide containing a 20 nucleotide (nt) palindromic sequence with a 3'-3' phosphodiester linkage between the $10^{th}$ and $11^{th}$ nt using either (A) T4 RNA ligase 1, (B) T4 RNA ligase 1+PEG 8K, or (C) T4 RNA Ligase 2 and a DNA oligonucleotide "splint" complementary to the 3'-UTR and bridging oligo. To prepare the samples for ligation, the bridging oligo is 5'-end phosphorylated in a reaction containing 50 μM oligo, ATP, 1× PNK Buffer and T4 Polynucleotide Kinase at 37° C. for 1 hour. Phosphorylated bridging oligo is then desalted using a Sephadex G-25 desalting column and hybridized to the transcript and splint in a reaction containing capped RNA transcript, 1× bridging oligo and 2× splint oligo by heating to 75° C. for 5 minutes followed by gradual cooling to room temperature over 5 minutes. An RNA ligation reaction is subsequently prepared to contain a 50% diluted hybridization reaction and (A) 1× RNA ligase Buffer, ATP and T4 RNA ligase 1 (NEB), (B) 1× RNA ligase Buffer, ATP, 10% PEG and T4 RNA ligase 1 (NEB), or (C) 1× T4RNA Ligase 2 Buffer and T4 RNA ligase 2 (NEB). Each is reacted for 90 minutes at 37° C. The completed ligation reaction is then purified using an RNeasy Mini Kit (Qiagen). The purified MCNA product is subsequently treated with DNase I to remove residual bridge oligonucleotide.

In some embodiments, MCNA can be prepared by splint-independent ligation of the 3' end of two copies of an RNA to the 5' ends of a single oligonucleotide containing two 5' ends and a linked 3'-3' phosphodiester bond within the sequence.

Untranslated Regions

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

In some embodiments, one or more polynucleotides of the MCNA include a 5' and/or 3' untranslated region. In some embodiments, a 5' untranslated region (5' UTR) includes one or more elements that affect an mRNA's stability or translation, for example, an iron responsive element. In some embodiments, a 5' untranslated region may be between about 50 and 500 nucleotides in length.

In some embodiments, a 3' untranslated region (3' UTR) includes one or more of a polyadenylation signal, a binding site for proteins that affect MCNA's stability of location in a cell, or one or more binding sites for miRNAs. In some embodiments, a 3' untranslated region may be between 50 and 500 nucleotides in length or longer. In some embodiments, a 3' untranslated region may be between 5 and 2,000 nucleotides in length.

Exemplary 3' and/or 5' UTR sequences can be derived from nucleic acid molecules that are stable (e.g., globin, actin, GAPDH, tubulin, histone, or citric acid cycle enzymes) to increase the stability of the sense MCNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., MCNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

3' UTR

In some embodiments, a 3' UTR comprises a plurality of multi-A segments with spacers in between. In some embodiments, spacers comprise DNA, RNA and/or modified bases. In some embodiments, each of the multi-A segments comprises 8-50 consecutive adenosines. In some embodiments, the plurality of multi-A segments range from 1-100 in number. In some embodiments, the spacers are of varying lengths ranging from 5-100. In some embodiments, a 3' UTR comprises a pseudoknot structure. A pseudoknot can be defined as an RNA structure minimally composed of two helical segments connected by single stranded regions or loops (Staple, D. W. et al., PLoS Biology, 2005, 3, e213). They are predominantly formed through secondary structures such as hairpin or stem loops and a distal single strand region. In some embodiments, a 3' UTR comprises a "kissing loop" sequence motif. Broadly defined, a kissing loop can be described as the structure formed when unpaired nucleotides in a stem/hairpin loop of one RNA molecule base pair with unpaired nucleotides of a second stem/hairpin loop of a separate RNA molecule. In some embodiments, a 3' UTR is not followed with a polyadenylation (poly-A) tail. In some embodiments, a 3' UTR binds to poly-A binding proteins (PABPs).

In some embodiments, MCNA include a 3' poly(A) tail structure. In some embodiments, a poly-A tail is 25-5,000 nucleotides in length. A poly-A tail on the 3' terminus of MCNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of MCNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

Typically, the presence of a "tail" serves to protect the MCNA from exonuclease degradation. The poly A tail is thought to stabilize natural messengers and synthetic sense MCNA. Therefore, in certain embodiments a long poly A tail can be added to an MCNA molecule thus rendering the MCNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, one or more polynucleotides of the MCNA includes a 3' poly(A) tail structure. Typically, the length of the poly-A tail can be at least about 10, 50, 100, 200, 300, 400 at least 500 nucleotides. In some embodiments, a poly-A tail on the 3' terminus of MCNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, MCNA include a 3' poly-C tail structure. A suitable poly-C tail on the 3' terminus of MCNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly-A or poly-C tail is adjusted to control the stability of a modified sense MCNA molecule of the invention and, thus, the transcription of protein that is coded for by one or more of the encoding polynucleotides of the MCNA. For example, since the length of the poly-A tail can influence the half-life of a sense MCNA molecule, the length of the poly-A tail can be adjusted to modify the level of resistance of the MCNA to nucleases and thereby control the time course of polynucleotide expression and/or polypeptide production in a target cell.

5' UTR

In some embodiments, MCNA include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp(5'(A,G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

One cap for MCNA produced by in vitro transcription is $m^7G(5')ppp(5')G$, which has been used as the dinucleotide cap in transcription with T7 or SP6 RNA polymerase in vitro to obtain MCNA having a cap structure in their 5'-termini. A method for the in vitro synthesis of capped MCNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with $—OCH_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}$ GpppG), trimethylated cap analog (e.g., $m^{2,2,7}$ GpppG), dimethylated symmetrical cap analogs (e.g., $m^7Gpppm^7G$), or anti reverse cap analogs (e.g., ARCA; $m^{7,2'Ome}$ GpppG, $m^{7\,2'd}$ GpppG, $m^{7,3'Ome}$ GpppG, $m^{7,3'd}$ GpppG and their tetraphosphate derivatives) (see, e.g., Jemielity, J. et al., "Novel 'anti-reverse' cap analogs with superior translational properties", RNA, 9:1108-1122 (2003)).

In some embodiments, a suitable cap is a 7-methyl guanylate ("$m^7G$") linked via a triphosphate bridge to the 5'-end of the first transcribed nucleotide, resulting in $m^7G$(5')ppp(5')N, where N is any nucleoside. A preferred embodiment of a $m^7G$ cap utilized in embodiments of the invention is $m^7G$(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-OCH$_3$ and 2'-OCH$_3$ cap analogs (Jemielity, J. et al., RNA, 9:1108-1122 (2003)). Additional cap analogs for use in embodiments of the invention include N7-benzylated dinucleoside tetraphosphate analogs (described in Grudzien, E. et al., RNA, 10:1479-1487 (2004)), phosphorothioate cap analogs (described in Grudzien-Nogalska, E., et al., RNA, 13:1745-1755 (2007)), and cap analogs (including biotinylated cap analogs) described in U.S. Pat. Nos. 8,093,367 and 8,304,529, incorporated by reference herein.

Nucleotide Modifications

In some embodiments, MCNA according to the present invention may be synthesized as unmodified or modified nucleic acid. Typically, nucleic acids are modified to enhance stability. Modifications of MCNA can include, for example, modifications of the nucleotides of the MCNA. A modified MCNA according to the invention can thus include, for example, backbone modifications, sugar modifications or base modifications. In some embodiments, MCNA may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as, e.g. 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thio-uridine (2sU), 5-methyl-cytidine (5mC), pseudouridine (ΨU), and 1-methyl-pseudouridine, 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonyl-methyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, MCNA of the of the present invention comprise encoding polynucleotides that comprise one or more modified nucleotides. In some embodiments, the one or more modified nucleotides are selected from the group consisting of 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine. In some embodiments, the modified nucleotides substitute 1-100% of corresponding native bases. In some embodiments, at least 25% of uridines are replaced with 2-thiouridines. In some embodiments, 100% cytidines are replaced with 5-methylcytidines. In some embodiments, modified nucleotides are further modified with a 4'-thio substitution on the ribose ring. In some embodiments, native nucleotides are modified with a 4'-thio substitution on the ribose ring.

In some embodiments, MCNA may contain nucleic acid backbone modifications. Typically, a backbone modification is a modification in which the phosphates of the backbone of the nucleotides contained in the MCNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, MCNA may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, MCNA may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate. In some embodiments, MCNA comprises modified bases selected from 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine.

Delivery Vehicles

According to the present invention, MCNA as described herein may be delivered as naked polynucleotides or via delivery vehicles. As used herein, the terms "delivery vehicle", "transfer vehicle", "nanoparticle" or grammatical equivalent, are used interchangeably.

In some embodiments, MCNA may be delivered via a single delivery vehicle. In some embodiments, MCNA may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16:307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired MCNA to a target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)-N,N-dimethyl-6-(9Z,12Z)-octadeca-9, 12-dien-1-yl) tetracosa-15,18-dien-1-amine (HGT5000), (15Z,18Z)-N,N-dimethyl-6-((9Z,12Z)-octadeca-9, 12-dien-1-yl)tetracosa-4, 15,18-trien-1-amine (HGT5001), and (15Z,18Z)-N,N-dimethyl-6-((9Z,12Z)-octadeca-9, 12-dien-1-yl)tetracosa-5, 15,18-trien-1-amine (HGT5002).

In some embodiments, provided liposomes include a cationic lipid described in WO 2013/063468 and in U.S. provisional application entitled "Lipid Formulations for Delivery of Messenger RNA" filed concurrently with the present application on even date, both of which are incorporated by reference herein.

In some embodiments, a cationic lipid comprises a compound of formula I-c1-a:

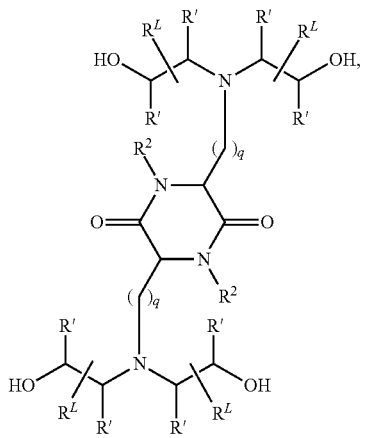

I-c1-a or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

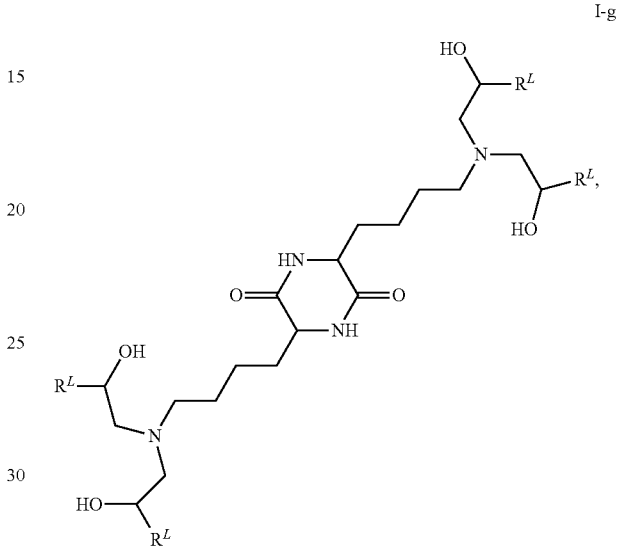

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). The structure of cKK-E12 is shown below:

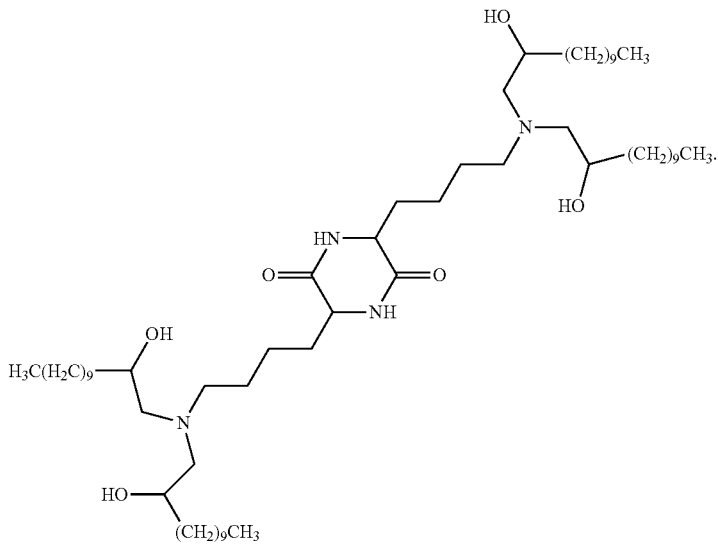

Additional exemplary cationic lipids include those of formula I:

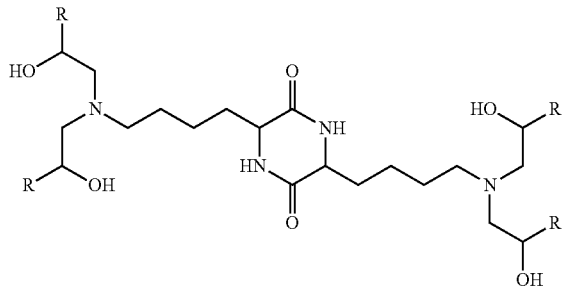

and pharmaceutically acceptable salts thereof, wherein,
R is

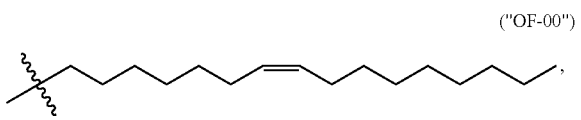 [SMILES: *CCCCCC/C=C\CCCCCCCC] ("OF-00")

R is

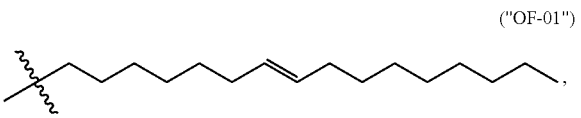 [SMILES: *CCCCCC/C=C/CCCCCCCC] ("OF-01")

R is

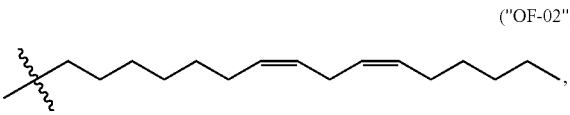 ("OF-02")

or
R is

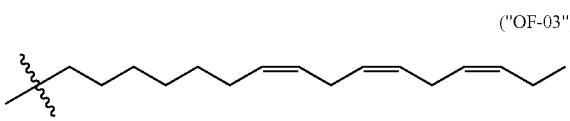 [SMILES: *CCCCCC/C=C\C/C=C\C/C=C\CC] ("OF-03")

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, the one or more cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N, N-dimethylpropylamine or "DLinDAP", 1,2-N,N*-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin- -DMA", 2,2-dilinoleyl-4-dimethylaminoethyl-[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof. (Heyes, J., et al., J Controlled Release 107:276-287 (2005); Morrissey, DV., et al., Nat. Biotechnol. 23(8):1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N, N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K.

T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5%, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the MCNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the MCNA is associated on both the surface of the liposome and encapsulated within the same liposome. For example, during preparation of the compositions of the present invention, cationic liposomes may associate with the MCNA through electrostatic interactions. For example, during preparation of the compositions of the present invention, cationic liposomes may associate with the MCNA through electrostatic interactions.

In some embodiments, the compositions and methods of the invention comprise MCNA encapsulated in a liposome. In some embodiments, the one or more MCNA species may be encapsulated in the same liposome. In some embodiments, the one or more MCNA species may be encapsulated in different liposomes. In some embodiments, the MCNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired MCNA into a liposome is often referred to as "loading". Exemplary methods are described in Lasic, et al., FEBS Lett., 312:255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a MCNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the MCNA contained therein and/or facilitate the delivery of MCNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of MCNA. Selection of an appropriate liposome size may take into consideration the site of the target cell or tissue and to some extent the application for which the liposome is being made.

In some embodiments, an appropriate size of lipo some is selected to facilitate systemic distribution of polypeptide encoded by the MCNA. In some embodiments, it may be desirable to limit transfection of the MCNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEGylated lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Pharmaceutical Compositions

To facilitate expression of MCNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

In some embodiments, a composition comprises MCNA encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels.

Provided liposomally-encapsulated or liposomally-associated MCNA, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

The present invention provides methods of delivering MCNA for in vivo protein production, comprising administering MCNA to a subject in need of delivery. In some embodiments, MCNA is administered via a route of delivery selected from the group consisting of intravenous delivery, subcutaneous delivery, oral delivery, subdermal delivery, ocular delivery, intratracheal injection pulmonary delivery (e.g. nebulization), intramuscular delivery, intrathecal delivery, or intraarticular delivery.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the MCNA to a muscle cell. In some embodiments the administration results in delivery of the MCNA to a hepatocyte (i.e., liver cell). In a particular embodiment, the intramuscular administration results in delivery of the MCNA to a muscle cell.

Alternatively or additionally, liposomally-encapsulated MCNA and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., MCNA) described herein. Therapeutic agents can be administered at regular intervals, depending on the nature, severity and extent of the subject's condition. In some embodiments, a therapeutically effective amount of the therapeutic agents (e.g., MCNA) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the MCNA contained therein. Such extended-release compositions may be conveniently administered to a subject at extended dosing intervals. For example, in one embodiment, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release MCNA over extended periods of time. Preferably, the extended-release means employed are combined with modifications made to the MCNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating a disease or disorder). For example, a therapeutically effective amount may be an amount sufficient to achieve a desired therapeutic and/or prophylactic effect. Generally, the amount of a therapeutic agent (e.g., MCNA) administered to a subject in need thereof will depend upon the characteristics of the subject.

Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the MCNA delivered by provided liposomes or compositions is expressed in the tissue in which the liposomes and/or compositions were administered. In some embodiments, the MCNA delivered is expressed in a tissue different from the tissue in which the liposomes and/or compositions were administered. Exemplary tissues in which delivered MCNA may be delivered and/or expressed include, but are not limited to the liver, kidney, heart, spleen, serum, brain, skeletal muscle, lymph nodes, skin, and/or cerebrospinal fluid.

In some embodiments, administering the provided composition results in an increased MCNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts) . In some embodiments, administering the provided composition results in an increased MCNA expression level by at least about 10%, 20%, 30%, 40%, 50%, 60%, 70%, 80%, 90%, or 95% as compared to the baseline level immediately before treatment. In some embodiments, administering the provided composition results in an increased MCNA expression level as compared to a MCNA expression level in subjects who are not treated According to various embodiments, the timing of expression of delivered MCNA can be tuned to suit a particular medical need. In some embodiments, the expression of the protein encoded by delivered MCNA is detectable 1, 2, 3, 6, 12, 24, 48, 72, and/or 96 hours after administration of provided liposomes and/or compositions. In some embodiments, the expression of the protein encoded by delivered MCNA is detectable 1 week, two weeks, and/or 1 month after administration.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Synthesis of Multimeric Coding Nucleic Acid (MCNA)

This example provides exemplary schemes for synthesizing the MCNA described in this application, for effective delivery and expression of MCNA encoding therapeutic proteins in vivo.

Synthesis of MCNA was attempted by ligating a synthetic oligonucleotide containing a 3'-3' phosphodiester bond to multiple polynucleotides using a complementary DNA splint. Several different T4 RNA ligases were tested for the ability to ligate a synthetic oligonucleotide containing a 3'-3' phosphodiester bond to multiple polynucleotides using a complementary DNA splint. The first RNA ligase ("RNA Ligase 1") was a "single-strand" RNA ligase that ligated single RNA strands, double RNA strands and double RNA strands designed to implement a single strand overhang. The second RNA ligase ("RNA Ligase 2") was a "double-stranded" RNA ligase that ligated nicks in RNA bound to a complementary oligonucleotide. Both RNA Ligase 1 and RNA Ligase 2 required phosphorylated 5' ends of the oligonucleotide bridge to proceed with adenylation for the ligation reaction.

As a non-limiting example, Erythropoietin (EPO) mRNA was ligated to a bridging oligo containing a 3'-3' phosphodiester bond using a complementary DNA splint. Examples of a bridging oligonucleotide that contains a 3'-3' phosphodiester bond and DNA splints are described below. The exemplary sequence for EPO used in the examples herein are listed below.

```
Erythropoietin (EPO) mRNA (including 5' and 3' UTR):
                                                              (SEQ ID NO: 1)
GGACAGAUCGCCUGGAGACGCCAUCCACGCUGUUUUGACCUCCAUAGAAGACACCGGGACCGAUCCAGCCUCCGCG

GCCGGGAACGGUGCAUUGGAACGCGGAUUCCCCGUGCCAAGAGUGACUCACCGUCCUUGACACGAUGGGGGUGCAC

GAAUGUCCUGCCUGGCUGUGGCUUCUCCUGUCCCUGCUGUCGCUCCCUCUGGGCCUCCCAGUCCUGGGCGCCCCAC

CACGCCUCAUCUGUGACAGCCGAGUCCUGGAGAGGUACCUCUUGGAGGCCAAGGAGGCCGAGAAUAUCACGACGGG

CUGUGCUGAACACUGCAGCUUGAAUGAGAAUAUCACUGUCCCAGACACCAAAGUUAAUUUCUAUGCCUGGAAGAGG

AUGGAGGUCGGGCAGCAGGCCGUAGAAGUCUGGCAGGGCCUGGCCCUGCUGUCGGAAGCUGUCCUGCGGGGCCAGG

CCCUGUUGGUCAACUCUUCCCAGCCGUGGGAGCCCCUGCAGCUGCAUGUGGAUAAAGCCGUCAGUGGCCUUCGCAG

CCUCACCACUCUGCUUCGGGCUCUGGGAGCCCAGAAGGAAGCCAUCUCCCCUCCAGAUGCGGCCUCAGCUGCUCCA

CUCCGAACAAUCACUGCUGACACUUUCCGCAAACUCUUCCGAGUCUACUCCAAUUUCCUCCGGGGAAAGCUGAAGC

UGUACACAGGGGAGGCCUGCAGGACAGGGGACAGAUGACGGGUGGCAUCCCUGUGACCCCUCCCCAGUGCCUCUCC

UGGCCCUGGAAGUUGCCACUCCAGUGCCCACCAGCCUUGUCCUAAUAAAAUUAAGUUGCAUCAAGCU

Erythropoietin (EPO) mRNA (including 5' and 3' UTR with 200 A poly(A) Tail):
                                                              (SEQ ID NO: 2)
GGACAGAUCGCCUGGAGACGCCAUCCACGCUGUUUUGACCUCCAUAGAAGACACCGGGACCGAUCCAGCCUCCGCG

GCCGGGAACGGUGCAUUGGAACGCGGAUUCCCCGUGCCAAGAGUGACUCACCGUCCUUGACACGAUGGGGGUGCAC

GAAUGUCCUGCCUGGCUGUGGCUUCUCCUGUCCCUGCUGUCGCUCCCUCUGGGCCUCCCAGUCCUGGGCGCCCCAC

CACGCCUCAUCUGUGACAGCCGAGUCCUGGAGAGGUACCUCUUGGAGGCCAAGGAGGCCGAGAAUAUCACGACGGG

CUGUGCUGAACACUGCAGCUUGAAUGAGAAUAUCACUGUCCCAGACACCAAAGUUAAUUUCUAUGCCUGGAAGAGG

AUGGAGGUCGGGCAGCAGGCCGUAGAAGUCUGGCAGGGCCUGGCCCUGCUGUCGGAAGCUGUCCUGCGGGGCCAGG

CCCUGUUGGUCAACUCUUCCCAGCCGUGGGAGCCCCUGCAGCUGCAUGUGGAUAAAGCCGUCAGUGGCCUUCGCAG

CCUCACCACUCUGCUUCGGGCUCUGGGAGCCCAGAAGGAAGCCAUCUCCCCUCCAGAUGCGGCCUCAGCUGCUCCA

CUCCGAACAAUCACUGCUGACACUUUCCGCAAACUCUUCCGAGUCUACUCCAAUUUCCUCCGGGGAAAGCUGAAGC

UGUACACAGGGGAGGCCUGCAGGACAGGGGACAGAUGACGGGUGGCAUCCCUGUGACCCCUCCCCAGUGCCUCUCC

UGGCCCUGGAAGUUGCCACUCCAGUGCCCACCAGCCUUGUCCUAAUAAAAUUAAGUUGCAUCAAGCUAAAAAAAAA

AAAAAAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA

Erythropoietin (EPO) mRNA (including 5' and 3' UTR with internal 65A poly(A)
region in 3' UTR):
                                                              (SEQ ID NO: 3)
GGACAGAUCGCCUGGAGACGCCAUCCACGCUGUUUUGACCUCCAUAGAAGACACCGGGACCGAUCCAGCCUCCGCG

GCCGGGAACGGUGCAUUGGAACGCGGAUUCCCCGUGCCAAGAGUGACUCACCGUCCUUGACACGAUGGGGGUGCAC

GAAUGUCCUGCCUGGCUGUGGCUUCUCCUGUCCCUGCUGUCGCUCCCUCUGGGCCUCCCAGUCCUGGGCGCCCCAC

CACGCCUCAUCUGUGACAGCCGAGUCCUGGAGAGGUACCUCUUGGAGGCCAAGGAGGCCGAGAAUAUCACGACGGG
```

-continued

CUGUGCUGAACACUGCAGCUUGAAUGAGAAUAUCACUGUCCCAGACACCAAAGUUAAUUUCUAUGCCUGGAAGAGG

AUGGAGGUCGGGCAGCAGGCCGUAGAAGUCUGGCAGGGCCUGGCCCUGCUGUCGGAAGCUGUCCUGCGGGGCCAGG

CCCUGUUGGUCAACUCUUCCCAGCCGUGGGAGCCCCUGCAGCUGCAUGUGGAUAAAGCCGUCAGUGGCCUUCGCAG

CCUCACCACUCUGCUUCGGGCUCUGGGAGCCCAGAAGGAAGCCAUCUCCCCUCCAGAUGCGGCCUCAGCUGCUCCA

CUCCGAACAAUCACUGCUGACACUUUCCGCAAACUCUUCCGAGUCUACUCCAAUUUCCUCCGGGGAAAGCUGAAGC

UGUACACAGGGGAGGCCUGCAGGACAGGGGACAGAUGACGGGUGGCAUCCCUGUGACCCCUCCCCAGUGCCUCUCC

UGGCCCUGGAAGUUGCCACUCCAGUGCCCACCAAAAAAAAAAAAAAAAAAAAAAAAAAAAAAAAAAAAAAAAAAAA

AAAAAAAAAAAAAAAAAAAAGCCUUGUCCUAAUAAAAUUAAGUUGCAUCAAGCU

Erythropoietin (EPO) mRNA (including 5' and 3' UTR with multiple short
internal poly(A) regions in 3' UTR):

(SEQ ID NO: 4)

GGACAGAUCGCCUGGAGACGCCAUCCACGCUGUUUUGACCUUCCAUAGAAGACACCGGGACCGAUCCAGCCUCCGCG

GCCGGGAACGGUGCAUUGGAACGCGGAUUCCCCGUGCCAAGAGUGACUCACCGUCCUUGACACGAUGGGGGUGCAC

GAAUGUCCUGCCUGGCUGUGGCUUCUCCUGUCCCUGCUGUCGCUCCCUCUGGGCCUCCCAGUCCUGGGCGCCCCAC

CACGCCUCAUCUGUGACAGCCGAGUCCUGGAGAGGUACCUCUUGGAGGCCAAGGAGGCCGAGAAUAUCACGACGGG

CUGUGCUGAACACUGCAGCUUGAAUGAGAAUAUCACUGUCCCAGACACCAAAGUUAAUUUCUAUGCCUGGAAGAGG

AUGGAGGUCGGGCAGCAGGCCGUAGAAGUCUGGCAGGGCCUGGCCCUGCUGUCGGAAGCUGUCCUGCGGGGCCAGG

CCCUGUUGGUCAACUCUUCCCAGCCGUGGGAGCCCCUGCAGCUGCAUGUGGAUAAAGCCGUCAGUGGCCUUCGCAG

CCUCACCACUCUGCUUCGGGCUCUGGGAGCCCAGAAGGAAGCCAUCUCCCCUCCAGAUGCGGCCUCAGCUGCUCCA

CUCCGAACAAUCACUGCUGACACUUUCCGCAAACUCUUCCGAGUCUACUCCAAUUUCCUCCGGGGAAAGCUGAAGC

UGUACACAGGGGAGGCCUGCAGGACAGGGGACAGAUGACGGGUGGCAAAAAAAAAAAAAAAUCCCUGUGACCCCUC

CCCAAAAAAAAAAAAAAAAGUGCCUCUCCUGGCCCUGGAAAAAAAAAAAAAAAAGUUGCCACUCCAGUGCCCACCAA

AAAAAAAAAAAAGCCUUGUCCUAAUAAAAUUAAGUUGCAUCAAGCU

Bridging Oligonucleotide 1:

(SEQ ID NO: 5)

5'-CGA CUC UCG G-3'-PO₄-3'-G GCU CUC AGC-5'
The bases included in SEQ ID NO: 5 are 2'-O-methyl RNA and the 3'-3' bridge
comprises PO₄.

Bridging Oligonucleotide 2:

(SEQ ID NO: 6)

5'-AAAAAAAAAA-3'-PO₄-3'-AAAAAAAAAA-5'

Bridging Oligonucleotide 3:

(SEQ ID NO: 7)

5'-AAA-3'-PO₄-3'-AAA-5'

Bridging Oligonucleotide 4:

(SEQ ID NO: 8)

5'-A-3'-PO₄-3'-A-5'

Splint Oligonucleotide 1:

(SEQ ID NO: 9)

5'-CCG AGA GTC GAG CTT GAT GCA ACT TAA TTT TAT TAG G-3'

Splint Oligonucleotide 2:

(SEQ ID NO: 10)

5'-CCG AGA GTG ATG CAA CTT AAT TTT ATT AGG-3'

Splint Oligonucleotide 3:

(SEQ ID NO: 11)

5'-TTT TTT TTT TAG CTT GAT GCA ACT TAA TTT TAT TAG G-3'

Splint Oligonucleotide 4:

(SEQ ID NO: 12)

5'-CCG AGA GTC GTT TTT TTT TTT TTT TTT-3'

-continued

Splint Oligonucleotide 5:
(SEQ ID NO: 13)
3'-G GAT TAT TTT AAT TCA ACG TAG TTC GAG CTG AGA GCC-5'-PO$_4$-5'-CCG AGA GTC

GAG CTT GAT GCA ACT TAA TTT TAT TAG G-3'

Splint Oligonucleotide 6:
(SEQ ID NO: 14)
3'-GGA TTA TTT TAA TTC AAC GTA GTG AGA GCC-5'-PO$_4$-5'-CCG AGA GTG ATG CAA CTT

AAT TTT ATT AGG-3'

Splint Oligonucleotide 7:
(SEQ ID NO: 15)
3'-G GAT TAT TTT AAT TCA ACG TAG TTC GAT TTT TTT TTT-5'-PO$_4$-5'-TTT TTT TTT

TAG CTT GAT GCA ACT TAA TTT TAT TAG G-3'

Splint Oligonucleotide 8:
(SEQ ID NO: 16)
3'-TTT TTT TTT TTT TTT TTT TTG CTG AGA GCC-5'-PO$_4$-5'-CCG AGA GTC GTT TTT TTT

TTT TTT TTT TTT-3'

EPO MCNA #1 (No Poly A Tail)

MCNA 1 (SEQ ID NO: 17) was prepared by splint ligation of the 3' end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5' untranslated region (UTR) and a 3' UTR flanking an RNA sequence encoding hEPO was transcribed using T7 RNA polymerase, enzymatically capped to contain a 5'-Cap 1 structure, and purified. This hEPO transcript was then ligated in a single step to a 2'-hydroxymethylated RNA (OMeRNA) "bridging" oligonucleotide containing a 20 nucleotide (nt) palindromic sequence with a 3'-3' phosphodiester linkage between the 10$^{th}$ and 11$^{th}$ nt (bridging oligo 1 (SEQ ID NO: 5);

5'-CGA CUC UCG G-3'-3'-G GCU CUC AGC-5', bold bases OMeRNA) using either (A) T4 RNA ligase 1+PEG 8K, (B) T4 RNA ligase 1 or (C) T4 RNA Ligase 2 and a DNA oligonucleotide "splint" complementary to the 3'-UTR and bridging oligo 1 (splint oligo 1 (SEQ ID NO: 9); 5' CCG AGA GTC GAG CTT GAT GCA ACT TAA TTT TAT TAG G 3'; all bases DNA). Alternatively, MCNA was prepared using splint oligonucleotide 5 (SEQ ID NO: 13), a palindromic sequence containing 2 copies of oligo 2 connected with a 5'-5' phosphodiester bond. To prepare the samples for ligation, bridging oligo 1 was 5'-end phosphorylated in a reaction containing 50 µM bridging oligo 1, 1 mM ATP, 1× PNK Buffer (NEB; 70 mM Tris-HCl, 10 mM MgCl$_2$, 5 mM DTT pH 7.6 at 25° C.) and 0.5 U/µL T4 Polynucleotide Kinase (NEB) at 37° C. for 1 h. Phosphorylated bridging oligo 1 was then desalted using a Sephadex G-25 desalting column (Princeton Separations) and hybridized to the transcript and splint in a reaction containing 3.2 µM capped hEPO transcript, 1.5 µM bridging oligo 1 and 3 µM splint oligo 1 (or 1.5 uM splint oligo 5) by heating to 75° C. for 5 min followed by gradual cooling to room temperature over 5 min. An RNA ligation reaction was subsequently prepared to contain a 50% diluted hybridization reaction and (A) 1× RNA ligase Buffer (NEB; 50 mM Tris-HCl, 10 mM MgCl$_2$, 1 mM DTT pH 7.5 at 25° C.), 1 mM ATP and 1 U/µL T4 RNA ligase 1 (NEB), (B) 1× RNA ligase Buffer (NEB; 50 mM Tris-HCl, 10 mM MgCl$_2$, 1 mM DTT pH 7.5 at 25° C.), 1 mM ATP, 10% PEG and 1 U/µL T4 RNA ligase 1 (NEB) or (C) 1× T4RNA Ligase 2 Buffer (NEB; 50 mM Tris-HCl, 2 mM MgCl$_2$, 1 mM DTT, 400 µM ATP at pH 7.5 at 25° C.) and 1 U/µL T4 RNA ligase 2 (NEB). Each was reacted for 90 minutes at 37° C. The completed ligation reaction was then purified using an RNeasy Mini Kit (Qiagen). A portion of the purified MCNA 1 product was subsequently treated with DNase I to remove residual bridge oligonucleotide to prevent potential endogenous RNase H cleavage of PCNA 1 in cells.

Alternatively, MCNA 1 (SEQ ID NO: 17) was prepared by splint ligation of the 3' end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5'-untranslated region (UTR) and a 3' UTR flanking an RNA sequence encoding hEPO was transcribed using T7 RNA polymerase, enzymatically capped to contain a 5'-Cap 1 structure and purified. This hEPO transcript was then ligated in a single step to a 2'-hydroxymethylated RNA (OMeRNA) "bridging" oligonucleotide containing a 20 nucleotide (nt) palindromic sequence with a 3'-3' phosphodiester linkage between the 10$^{th}$ and 11$^{th}$ nt (bridging oligo 1 (SEQ ID NO: 5);

5'-CGA CUC UCG G-3'-3'-G GCU CUC AGC-5', bold bases OMeRNA) using either (A) T4 RNA ligase 1+PEG 8K, (B) T4 RNA ligase 1 or (C) T4 RNA Ligase 2 and a DNA oligonucleotide "splint" complementary to the 3'-UTR and bridging oligo 1 (splint oligo 1 (SEQ ID NO: 9); 5' CCG AGA GTC GAG CTT GAT GCA ACT TAA TTT TAT TAG G 3'; all bases DNA). Alternatively, MCNA was prepared using splint oligonucleotide 6 (SEQ ID NO: 14), and a palindromic sequence containing 2 copies of oligo 2 connected with a 5'-5' phosphodiester bond. To prepare the samples for ligation, bridging oligo 1 was 5'-end phosphorylated in a reaction containing 50 µM bridging oligo 1, 1 mM ATP, 1× PNK Buffer (NEB; 70 mM Tris-HCl, 10 mM MgCl$_2$, 5 mM DTT pH 7.6 at 25° C.) and 0.5 U/µL T4 Polynucleotide Kinase (NEB) at 37° C. for 1 hour. Phosphorylated bridging oligo 1 was then desalted using a Sephadex G-25 desalting column (Princeton Separations) and hybridized to the transcript and splint in a reaction containing 3.2 µM capped hEPO transcript, 1.5 µM bridging oligo 1 and 3 µM splint oligo 1 (or 1.5 uM splint oligo 6) by heating to 75° C. for 5 minutes followed by gradual cooling to room temperature over 5 minutes. An RNA ligation reaction was subsequently prepared to contain a 50% diluted hybridization reaction and (A) 1× RNA ligase Buffer (NEB; 50 mM Tris-HCl, 10 mM MgCl$_2$, 1 mM DTT pH 7.5 at 25° C.), 1 mM ATP and 1 U/µL T4 RNA ligase 1 (NEB), (B) 1× RNA ligase Buffer (NEB; 50 mM Tris-HCl, 10 mM MgCl$_2$, 1 mM DTT pH 7.5 at 25° C.), 1 mM ATP, 10% PEG and 1 U/µL T4 RNA ligase 1 (NEB) or (C) 1× T4RNA Ligase 2 Buffer (NEB; 50 mM Tris-HCl, 2 mM MgCl$_2$, 1 mM DTT, 400 µM ATP pH 7.5 at 25° C.) and 1 U/µL T4 RNA ligase 2 (NEB). Each was reacted for 90 minutes 37° C. The completed ligation reaction was then purified using an RNeasy Mini Kit (Qiagen). A portion of the purified MCNA 1 product was subsequently treated with DNase I to remove residual bridge oligonucleotide to prevent potential endogenous RNase H cleavage of PCNA 1 in cells.

MCNA 1 (No Poly(A) Tail Sequence):
(SEQ ID NO: 17)
5'-GGACAGAUCGCCUGGAGACGCCAUCCACGCUGUUUUGACCUCCAUA

GAAGACACCGGGACCGAUCCAGCCUCCGCGGCCGGGAACGGUGCAUUGG

AACGCGGAUUCCCCGUGCCAAGAGUGACUCACCGUCCUUGACACGAUGG

GGGUGCACGAAUGUCCUGCCUGGCUGUGGCUUCUCCUGUCCCUGCUGUC

GCUCCCUCUGGGCCUCCCAGUCCUGGGCGCCCCACCACGCCUCAUCUGU

GACAGCCGAGUCCUGGAGAGGUACCUCUUGGAGGCCAAGGAGGCCGAGA

AUAUCACGACGGGCUGUGCUGAACACUGCAGCUUGAAUGAGAAUAUCAC

UGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAG

CUGUCCUGCGGGGCCAGGCCCUGUUGGUCAACUCUUCCCAGCCGUGGGA

GCCCCUGCAGCUGCAUGUGGAUAAAGCCGUCAGUGGCCUUCGCAGCCUC

ACCACUCUGCUUCGGGCUCUGGGAGCCCAGAAGGAAGCCAUCUCCCCUC

CAGAUGCGGCCUCAGCUGCUCCACUCCGAACAAUCACUGCUGACACUUU

CCGCAAACUCUUCCGAGUCUACUCCAAUUUCCUCCGGGGAAAGCUGAAG

CUGUACACAGGGGAGGCCUGCAGGACAGGGGACAGAUGACGGGUGGCAU

CCCUGUGACCCCUCCCCAGUGCCUCUCCUGGCCCUGGAAGUUGCCACUC

CAGUGCCCACCAGCCUUGUCCUAAUAAAAAUUAAGUUGCAUCAAGCU

CGACUCUCGG-3'-PO$_2$-3'-GGCUCUCAGCUCGAACUACGUUGAAUU

AAAAUAAUCCUGUUCCGACCACCCGUGACCUCACCGUUGAAGGUCCCGG

UCCUCUCCGUGACCCCUCCCCAGUGUCCCUACGGUGGGCAGUAGACAGG

GGACAGGACGUCCGGAGGGGACACAUGUCGAAGUCGAAAGGGGCCUCCU

UUAACCUCAUCUGAGCCUUCUCAAACGCCUUUCACAGUCGUCACUAACA

AGCCUCACCUCGUCGACUCCGGCGUAGACCUCCCCUCUACCGAAGGAAG

ACCCGAGGGUCUCGGGCUUCGUCUCACCACUCCGACGCUUCCGGUGACU

GCCGAAAUAGGUGUACGUCGACGUCCCCGAGGGUGCCGACCCUUCUCAA

CUGGUUGUCCCGGACCGGGGCGUCCUGUCGAAGGCUGUCGUCCCGGUCC

GGGACGGUCUGAAGAUGCCGGACGACGGGCUGGAGGUAGGAGAAGGUCC

GUAUCUUUAAUUGAAACCACAGACCCUGUCACUAUAAGAGUAAGUUCGA

CGUCACAAGUCGUGUCGGGCAGCACUAUAAGAGCCGGAGGAACCGGAGG

UUCUCCAUGGAGAGGUCCUGAGCCGACAGUGUCUACUCCGCACCACCCC

GCGGGUCCUGACCCUCCGGGUCUCCCUCGCUGUCGUCCCUGUCCUCUUC

GGUGUCGGUCCGUCCUGUAAGCACGUGGGGGUAGCACAGUUCCUGCCAC

UCAGUGAGAACCGUGCCCCUUAGGCGCAAGGUUACGUGGCAAGGGCCGG

CGCCUCCGACCUAGCCAGGGCCACAGAAGAUACCUCCAGUUUUGUCGCA

CCUACCGCAGAGGUCCGCUAGACAGG-5'

EPO MCNA #2

MCNA 2 (SEQ ID NO: 18) was prepared by splint ligation of the 3' end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5'-untranslated region (UTR) and a 3' UTR flanking an RNA sequence encoding hEPO was transcribed using T7 RNA polymerase, enzymatically capped to contain a 5'-Cap 1 structure and purified. This hEPO transcript was then ligated in a single step to an RNA "bridging" oligonucleotide containing a 20 nucleotide (nt) palindromic sequence with a 3'-3' phosphodiester linkage between the 10$^{th}$ and 11$^{th}$ nt (bridging oligo 2 (SEQ ID NO: 6);

5'-<u>AAA AAA AAA A</u>-3'-3'-A <u>AAA AAA AAA</u>-5', underlined bases RNA) using T4 RNA ligase 1+PEG 8K and a DNA oligonucleotide "splint" complementary to the 3'-UTR and bridging oligo 2 (splint oligo 3 (SEQ ID NO: 11); 5' TTT TTT TTT TAG CTT GAT GCA ACT TAA TTT TAT TAG G 3'; all bases DNA). Alternatively, MCNA was prepared using splint oligo 7 (SEQ ID NO: 15), a palindromic sequence containing 2 copies of splint oligo 7 connected with a 5'-5' phosphodiester bond. To prepare the samples for ligation, bridging oligo 2 was 5'-end phosphorylated in a reaction containing 50 µM oligo 3, 1 mM ATP, 1× PNK Buffer (NEB; 70 mM Tris-HCl, 10 mM MgCl$_2$, 5 mM DTT, pH 7.6 at 25° C.) and 0.5 U/µL, T4 Polynucleotide Kinase (NEB) at 37° C. for 1 hour. Phosphorylated bridging oligo 2 was then desalted using a Sephadex G-25 desalting column (Princeton Separations) and hybridized to the transcript and splint in a reaction containing 3.2 µM capped hEPO transcript, 1.5 µM bridging oligo 2 and 3 µM splint oligo 3 (or 1.5 uM splint oligo 7) by heating to 75° C. for 5 minutes followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT, pH 7.5 at 25° C.), 1 mM ATP, 10% PEG and 1 U/µL, T4 RNA ligase 1 (NEB), and was reacted for 90 min at 37° C. The completed ligation reaction was then purified using an RNeasy Mini Kit (Qiagen).

EPO PCNA #2 (10A-10A Bridge):
(SEQ ID NO: 18)
5'-GGACAGAUCGCCUGGAGACGCCAUCCACGCUGUUUUGACCUCCAUA

GAAGACACCGGGACCGAUCCAGCCUCCGCGGCCGGGAACGGUGCAUUGG

AACGCGGAUUCCCCGUGCCAAGAGUGACUCACCGUCCUUGACACGAUGG

GGGUGCACGAAUGUCCUGCCUGGCUGUGGCUUCUCCUGUCCCUGCUGUC

```
-continued
GCUCCCUCUGGGCCUCCCAGUCCUGGGCGCCCCACCACGCCUCAUCUGU

GACAGCCGAGUCCUGGAGAGGUACCUCUUGGAGGCCAAGGAGGCCGAGA

AUAUCACGACGGGCUGUGCUGAACACUGCAGCUUGAAUGAGAAUAUCAC

UGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAG

CUGUCCUGCGGGGCCAGGCCCUGUUGGUCAACUCUUCCCAGCCGUGGGA

GCCCCUGCAGCUGCAUGUGGAUAAAGCCGUCAGUGGCCUUCGCAGCCUC

ACCACUCUGCUUCGGGCUCUGGGAGCCCAGAAGGAAGCCAUCUCCCCUC

CAGAUGCGGCCUCAGCUGCUCCACUCCGAACAAUCACUGCUGACACUUU

CCGCAAACUCUUCCGAGUCUACUCCAAUUUCCUCCGGGGAAAGCUGAAG

CUGUACACAGGGGAGGCCUGCAGGACAGGGGACAGAUGACGGGUGGCAU

CCCUGUGACCCCUCCCCAGUGCCUCUCCUGGCCCUGGAAGUUGCCACUC

CAGUGCCCACCAGCCUUGUCCUAAUAAAAUUAAGUUGCAUCAAGCUAAA

AAAAAAA-3'-PO4-3'-AAAAAAAAAAUCGAACUACGUUGAAUUAAA

AUAAUCCUGUUCCGACCACCCGUGACCUCACCGUUGAAGGUCCCGGUCC

UCUCCGUGACCCCUCCCCAGUGUCCCUACGGUGGGCAGUAGACAGGGGA

CAGGACGUCCGGAGGGGACACAUGUCGAAGUCGAAAGGGGCCUCCUUUA

ACCUCAUCUGAGCCUUCUCAAACGCCUUUCACAGUCGUCACUAACAAGC

CUCACCUCGUCGACUCCGGCGUAGACCUCCCCUCUACCGAAGGAAGACC

CGAGGGUCUCGGGCUUCGUCUCACCACUCCGACGCUUCCGGUGACUGCC

GAAAUAGGUGUACGUCGACGUCCCGAGGGUGCCGACCCUUCUCAACUG

GUUGUCCCGGACCGGGGCGUCCUGUCGAAGGCUGUCGUCCCGGUCCGGG

ACGGUCUGAAGAUGCCGGACGACGGGCUGGAGGUAGGAGAAGGUCCGUA

UCUUUAAUUGAAACCACAGACCCUGUCACUAUAAGAGUAAGUUCGACGU

CACAAGUCGUGUCGGGCAGCACUAUAAGAGCCGGAGGAACCGGAGGUUC

UCCAUGGAGAGGUCCUGAGCCGACAGUGUCUACUCCGCACCACCCCGCG

GGUCCUGACCCUCCGGGUCUCCCUCGCUGUCGUCCCUGUCCUCUUCGGU

GUCGGUCCGUCCUGUAAGCACGUGGGGGUAGCACAGUUCCUGCCACUCA

GUGAGAACCGUGCCCCUUAGGCGCAAGGUUACGUGGCAAGGGCCGGCGC

CUCCGACCUAGCCAGGGCCACAGAAGAUACCUCCAGUUUUGUCGCACCU

ACCGCAGAGGUCCGCUAGACAGG-5'
```

EPO MCNA #3

MCNA 3 (SEQ ID NO: 19) was prepared by splint ligation of the 3'end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5' untranslated region (UTR), a 3' UTR with both UTRs flanking an RNA sequence encoding hEPO was transcribed using T7 RNA polymerase, enzymatically capped to contain a 5'-Cap 1 structure and purified. The construct was treated further to incorporate a poly(A) tail length of ~200 As using poly(A) polymerase. This hEPO transcript was then ligated in a single step to OMeRNA "bridge" oligonucleotide containing a 20 nucleotide (nt) palindromic sequence with a 3'-3' phosphodiester linkage between the 10<sup>th</sup> and 11<sup>th</sup> nt (bridging oligo 1 (SEQ ID NO: 5);

5'-<u>CGA CUC UCG G</u>-3'-3'-<u>G GCU CUC AGC</u>-5' bold bases OMeRNA) using T4 RNA ligase 1+PEG 8K and a DNA oligonucleotide "splint" complementary to the 3'-UTR and bridging oligo 1 (splint oligo 4 (SEQ ID NO: 12); 5' CCG AGA GTC GTT TTT TTT TTT TTT TTT TTT 3'; all bases DNA). Alternatively, MCNA could be prepared using splint oligo 8 (SEQ ID NO: 16), a palindromic sequence containing 2 copies of splint oligo 4 connected with a 5'-5' phosphodiester bond. To prepare the samples for ligation, bridging oligo 1 was 5'-end phosphorylated in a reaction containing 50 µM oligo 1, 1 mM ATP, 1× PNK Buffer (NEB; 70 mM Tris-HCl, 10 mM MgCl$_2$, 5 mM DTT, pH 7.6 at 25° C.) and 0.5 U/µL, T4 Polynucleotide Kinase (NEB) at 37° C. for 1 hour. Phosphorylated bridging oligo 1 was then desalted using a Sephadex G-25 desalting column (Princeton Separations) and hybridized to the transcript and splint in a reaction containing 3.2 µM capped hEPO transcript, 1.5 µM bridging oligo 1 and 3 µM splint oligo 4 by heating to 75° C. for 5 minutes followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT, pH 7.5 at 25° C.), 1 mM ATP, 10% PEG and 1 U/µL, T4 RNA ligase 1 (NEB), and was reacted for 90 minutes at 37° C. The completed ligation reaction was then purified using an RNeasy Mini Kit (Qiagen).

```
EPO PCNA #3 (includes 200A Poly(A) Tail):
                                          (SEQ ID NO: 19)
5'-GGACAGAUCGCCUGGAGACGCCAUCCACGCUGUUUUGACCUCCAUA

GAAGACACCGGGACCGAUCCAGCCUCCGCGGCCGGGAACGGUGCAUUGG

AACGCGGAUUCCCCGUGCCAAGAGUGACUCACCGUCCUUGACACGAUGG

GGGUGCACGAAUGUCCUGCCUGGCUGUGGCUUCUCCUGUCCCUGCUGUC

GCUCCCUCUGGGCCUCCCAGUCCUGGGCGCCCCACCACGCCUCAUCUGU

GACAGCCGAGUCCUGGAGAGGUACCUCUUGGAGGCCAAGGAGGCCGAGA

AUAUCACGACGGGCUGUGCUGAACACUGCAGCUUGAAUGAGAAUAUCAC

UGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAG

CUGUCCUGCGGGGCCAGGCCCUGUUGGUCAACUCUUCCCAGCCGUGGGA

GCCCCUGCAGCUGCAUGUGGAUAAAGCCGUCAGUGGCCUUCGCAGCCUC

ACCACUCUGCUUCGGGCUCUGGGAGCCCAGAAGGAAGCCAUCUCCCCUC

CAGAUGCGGCCUCAGCUGCUCCACUCCGAACAAUCACUGCUGACACUUU

CCGCAAACUCUUCCGAGUCUACUCCAAUUUCCUCCGGGGAAAGCUGAAG

CUGUACACAGGGGAGGCCUGCAGGACAGGGGACAGAUGACGGGUGGCAU

CCCUGUGACCCCUCCCCAGUGCCUCUCCUGGCCCUGGAAGUUGCCACUC

CAGUGCCCACCAGCCUUGUCCUAAUAAAAUUAAGUUGCAUCAAGCUAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA
```

-continued
AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

A-_CGACUCUCGG_-3'-_PO__2_-3'-_GGCUCUCAGC_-AAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAUCGAACUACGU

UGAAUUAAAAUAAUCCUGUUCCGACCACCCGUGACCUCACCGUUGAAGG

UCCCGGUCCUCUCCGUGACCCCUCCCCAGUGUCCCUACGGUGGGCAGUA

GACAGGGGACAGGACGUCCGGAGGGGACACAUGUCGAAGUCGAAAGGGG

CCUCCUUUAACCUCAUCUGAGCCUUCUCAAACGCCUUUCACAGUCGUCA

CUAACAAGCCUCACCUCGUCGACUCCGGCGUAGACCUCCCCUCUACCGA

AGGAAGACCCGAGGGUCUCGGGCUUCGUCUCACCACUCCGACGCUUCCG

GUGACUGCCGAAAUAGGUGUACGUCGACGUCCCCGAGGGUGCCGACCCU

UCUCAACUGGUUGUCCCGGACCGGGGCGUCCUGUCGAAGGCUGUCGUCC

CGGUCCGGGACGGUCUGAAGAUGCCGGACGACGGGCUGGAGGUAGGAGA

AGGUCCGUAUCUUUAAUUGAAACCACAGACCCUGUCACUAUAAGAGUAA

GUUCGACGUCACAAGUCGUGUCGGGCAGCACUAUAAGAGCCGGAGGAAC

CGGAGGUUCUCCAUGGAGAGGUCCUGAGCCGACAGUGUCUACUCCGCAC

CACCCCGCGGGUCCUGACCCUCCGGGUCUCCCUCGCUGUCGUCCCUGUC

CUCUUCGGUGUCGGUCCGUCCUGUAAGCACGUGGGGGUAGCACAGUUCC

UGCCACUCAGUGAGAACCGUGCCCCUUAGGCGCAAGGUUACGUGGCAAG

GGCCGGCGCCUCCGACCUAGCCAGGGCCACAGAAGAUACCUCCAGUUUU

GUCGCACCUACCGCAGAGGUCCGCUAGACAGG-5'

EPO MCNA #4

MCNA 4 (SEQ ID NO: 20) was prepared by splint-independent ligation of the 3'-end of two copies of an RNA encoding the human Erythropoietin (hEPO) protein to the 5'-ends of a single dinucleotide containing two A's linked by a 3'-3' phosphodiester bond. Briefly, a 5'-capped RNA containing a 5'-untranslated region (UTR), a 3' UTR with both UTRs flanking an RNA sequence encoding hEPO was transcribed using T7 RNA polymerase, enzymatically capped to contain a 5'-Cap 1 structure and purified. The construct was treated further to incorporate a poly(A) tail length of ~200 As using poly(A) polymerase. This hEPO transcript was then ligated via two steps to an RNA bridge oligonucleotide containing a trimeric repeat of As with a 3'-3' phosphodiester linkage to another trimeric repeat of As (bridging oligo 3 (SEQ ID NO: 7); 5'-_AAA_-3'-3'-_AAA_-5', underlined bases RNA) using T4 RNA ligase 1+PEG 8K. To prepare the samples for ligation, bridging oligo 3 was 5'-end phosphorylated in a reaction containing 50 µM oligo 7, 1 mM ATP, 1× PNK Buffer (NEB; 70 mM Tris-HCl, 10 mM MgCl$_2$, 5 mM DTT, pH 7.6 at 25° C.) and 0.5 U/µL, T4 Polynucleotide Kinase (NEB) at 37° C. for 1 hour. Phosphorylated bridging oligo 3 was then desalted using a Sephadex G-25 desalting column (Princeton Separations) and denatured in a reaction containing 2.4 µM capped and tailed hEPO transcript and 50 µM bridging oligo 3 by heating to 75° C. for 5 min followed by gradual cooling to room temperature over 5 min. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT pH 7.5 at 25° C.), 1 mM ATP, 10% PEG and 1 U/µL, T4 RNA ligase 1 (NEB), and was reacted for 90 minutes at 37° C. The partial ligation reaction was then purified using an RNeasy Mini Kit (Qiagen). The ligation reaction was repeated using a 1:1 molar ratio of the partial ligation product and additional capped and tailed hEPO transcript, and purified as previously.

EPO PCNA #4 (includes 200A Poly(A) Tail with 3A-3A Bridge):

(SEQ ID NO: 20)
5'-GGACAGAUCGCCUGGAGACGCCAUCCACGCUGUUUUGACCUCCAU

AGAAGACACCGGGACCGAUCCAGCCUCCGCGGCCGGGAACGGUGCAUU

GGAACGCGGAUUCCCCGUGCCAAGAGUGACUCACCGUCCUUGACACGA

UGGGGGUGCACGAAUGUCCUGCCUGGCUGUGGCUUCUCCUGUCCCUGC

UGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGG

CCGAGAAUAUCACGACGGGCUGUGCUGAACACUGCAGCUUGAAUGAGA

AUAUCACUGUCCCAGACACCAAAGUUAAUUUCUAUGCCUGGAAGAGGA

UGGAGGUCGGGCAGCAGGCCGUAGAAGUCUGGCAGGGCCUGGCCCUGC

UGUCGGAAGCUGUCCUGCGGGGCCAGGCCCUGUUGGUCAACUCUUCCC

AGCCGUGGGAGCCCCUGCAGCUGCAUGUGGAUAAAGCCGUCAGUGGCC

UUCGCAGCCUCACCACUCUGCUUCGGGCUCUGGGAGCCCAGAAGGAAG

CCAUCUCCCCUCCAGAUGCGGCCUCAGCUGCUCCACUCCGAACAAUCA

CUGCUGACACUUUCCGCAAACUCUUCCGAGUCUACUCCAAUUUCCUCC

GGGGAAAGCUGAAGCUGUACACAGGGGAGGCCUGCAGGACAGGGGACA

GAUGACGGGUGGCAUCCCUGUGACCCUCCCCAGUGCCUCUCCUGGCC

CUGGAAGUUGCCACUCCAGUGCCCACCAGCCUUGUCCUAAUAAAAUUA

AGUUGCAUCAAGCUAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAA-_AAA_-3'-_PO__2_-3'-_AAA_-AAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AUCGAACUACGUUGAAUUAAAAUAAUCCUGUUCCGACCACCCGUGACC

UCACCGUUGAAGGUCCCGGUCCUCUCCGUGACCCCUCCCCAGUGUCCC

UACGGUGGGCAGUAGACAGGGGACAGGACGUCCGGAGGGGACACAUGU

CGAAGUCGAAAGGGGCCUCCUUUAACCUCAUCUGAGCCUUCUCAAACG

CCUUUCACAGUCGUCACUAACAAGCCUCACCUCGUCGACUCCGGCGUA

GACCUCCCCUCUACCGAAGGAAGACCCGAGGGUCUCGGGCUUCGUCUC

-continued
```
ACCACUCCGACGCUUCCGGUGACUGCCGAAAUAGGUGUACGUCGACGU

CCCCGAGGGUGCCGACCCUUCUCAACUGGUUGUCCCGGACCGGGGCGU

CCUGUCGAAGGCUGUCGUCCCGGUCCGGGACGGUCUGAAGAUGCCGGA

CGACGGGCUGGAGGUAGGAGAAGGUCCGUAUCUUUAAUUGAAACCACA

GACCCUGUCACUAUAAGAGUAAGUUCGACGUCACAAGUCGUGUCGGC

AGCACUAUAAGAGCCGGAGGAACCGGAGGUUCUCCAUGGAGAGGUCCU

GAGCCGACAGUGUCUACUCCGCACCACCCCGCGGGUCCUGACCCUCCG

GGUCUCCCUCGCUGUCGUCCCUGUCCUCUUCGGUGUCGGUCCGUCCUG

UAAGCACGUGGGGGUAGCACAGUUCCUGCCACUCAGUGAGAACCGUGC

CCCUUAGGCGCAAGGUUACGUGGCAAGGGCCGGCGCCUCCGACCUAGC

CAGGGCCACAGAAGAUACCUCCAGUUUUGUCGCACCUACCGCAGAGGU

CCGCUAGACAGG-5'
```

EPO MCNA #5

MCNA 5 (SEQ ID NO: 21) was prepared by splint-independent ligation of the 3' end of two copies of an RNA encoding the human Erythropoietin (hEPO) protein to the 5' ends of a single dinucleotide containing two A's linked by a 3'-3' phosphodiester bond. Briefly, a 5'-capped RNA containing a 5'-untranslated region (UTR), a 3' UTR with both UTRs flanking an RNA sequence encoding hEPO was transcribed using T7 RNA polymerase, enzymatically capped to contain a 5'-Cap 1 structure and purified. The construct was treated further to incorporate a poly(A) tail length of ~200 As using poly(A) polymerase. This hEPO transcript was then ligated via two steps to an RNA "bridging" dinucleotide containing an A with a 3'-3' phosphodiester linkage to another A (bridging oligo 4 (SEQ ID NO: 8); 5'A 3'3'A 5', underlined bases RNA) using T4 RNA ligase 1+PEG 8K. To prepare the samples for ligation, bridging oligo 4 was 5'-end phosphorylated in a reaction containing 50 μM bridging oligo 4, 1 mM ATP, 1× PNK Buffer (NEB; 70 mM Tris-HCl, 10 mM MgCl$_2$, 5 mM DTT, pH 7.6 at 25° C.) and 0.5 U/μL, T4 Polynucleotide Kinase (NEB) at 37° C. for 1 hour. Phosphorylated bridging oligo 4 was then desalted using a Sephadex G-25 desalting column (Princeton Separations) and denatured in a reaction containing 2.4 μM capped and tailed hEPO transcript and 50 μM bridging oligo 4 by heating to 75° C. for 5 minutes followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT, pH 7.5 at 25° C.), 1 mM ATP, 10% PEG and 1 U/μL, T4 RNA ligase 1 (NEB), and was reacted for 90 minutes at 37° C. The partial ligation reaction was then purified using an RNeasy Mini Kit (Qiagen). The ligation reaction was repeated using a 1:1 molar ratio of the partial ligation product and additional capped and tailed hEPO transcript, and purified as previously.

EPO PCNA #5 (includes 200A Poly(A) Tail with 1A-1A Bridge):

(SEQ ID NO: 21)
```
5'-GGACAGAUCGCCUGGAGACGCCAUCCACGCUGUUUUGACCUCCAU

AGAAGACACCGGGACCGAUCCAGCCUCCGCGGCCGGGAACGGUGCAUU

GGAACGCGGAUUCCCCGUGCCAAGAGUGACUCACCGUCCUUGACACGA
```

-continued
```
UGGGGGUGCACGAAUGUCCUGCCUGGCUGUGGCUUCUCCUGUCCCUGC

UGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGG

CCGAGAAUAUCACGACGGGCUGUGCUGAACACUGCAGCUUGAAUGAGA

AUAUCACUGUCCCAGACACCAAAGUUAAUUUCUAUGCCUGGAAGAGGA

UGGAGGUCGGGCAGCAGGCCGUAGAAGUCUGGCAGGGCCUGGCCCUGC

UGUCGGAAGCUGUCCUGCGGGGCCAGGCCCUGUUGGUCAACUCUUCCC

AGCCGUGGGAGCCCCUGCAGCUGCAUGUGGAUAAAGCCGUCAGUGGCC

UUCGCAGCCUCACCACUCUGCUUCGGGCUCUGGGAGCCCAGAAGGAAG

CCAUCUCCCCUCCAGAUGCGGCCUCAGCUGCUCCACUCCGAACAAUCA

CUGCUGACACUUUCCGCAAACUCUUCCGAGUCUACUCCAAUUUCCUCC

GGGGAAAGCUGAAGCUGUACACAGGGGAGGCCUGCAGGACAGGGGACA

GAUGACGGGUGGCAUCCCUGUGACCCCUCCCCAGUGCCUCUCCUGGCC

CUGGAAGUUGCCACUCCAGUGCCCACCAGCCUUGUCCUAAUAAAAUUA

AGUUGCAUCAAGCUAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAA-A-3'-PO$_4$-3'-A-AAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAUCG

AACUACGUUGAAUUAAAAUAAUCCUGUUCCGACCACCCGUGACCUCAC

CGUUGAAGGUCCCGGUCCUCUCCGUGACCCCUCCCCAGUGUCCCUACG

GUGGGCAGUAGACAGGGGACAGGACGUCCGGAGGGGACACAUGUCGAA

GUCGAAAGGGGCCUCCUUUAACCUCAUCUGAGCCUUCUCAAACGCCUU

UCACAGUCGUCACUAACAAGCCUCACCUCGUCGACUCCGGCGUAGACC

UCCCCUCUACCGAAGGAAGACCCGAGGGUCUCGGGCUUCGUCUCACCA

CUCCGACGCUUCCGGUGACUGCCGAAAUAGGUGUACGUCGACGUCCCC

GAGGGUGCCGACCCUUCUCAACUGGUUGUCCCGGACCGGGGCGUCCUG

UCGAAGGCUGUCGUCCCGGUCCGGGACGGUCUGAAGAUGCCGGACGAC

GGGCUGGAGGUAGGAGAAGGUCCGUAUCUUUAAUUGAAACCACAGACC

CUGUCACUAUAAGAGUAAGUUCGACGUCACAAGUCGUGUCGGGCAGCA

CUAUAAGAGCCGGAGGAACCGGAGGUUCUCCAUGGAGAGGUCCUGAGC

CGACAGUGUCUACUCCGCACCACCCCGCGGGUCCUGACCCUCCGGGUC

UCCCUCGCUGUCGUCCCUGUCCUCUUCGGUGUCGGUCCGUCCUGUAAG

CACGUGGGGUAGCACAGUUCCUGCCACUCAGUGAGAACCGUGCCCU

UAGGCGCAAGGUUACGUGGCAAGGGCCGGCGCCUCCGACCUAGCCAGG

GCCACAGAAGAUACCUCCAGUUUUGUCGCACCUACCGCAGAGGUCCGC

UAGACAGG-5'
```

EPO PCNA #6

PCNA 6 (SEQ ID NO: 22) is prepared by splint ligation of the 3' end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5'-untranslated region (UTR), a 3' UTR containing an internal section of 65 consecutive As with both UTRs flanking an RNA sequence encoding hEPO is transcribed using T7 RNA polymerase, enzymatically capped to contain a 5'-Cap 1 structure and purified. This hEPO transcript is then ligated in a single step to a OMeRNA "bridging" oligonucleotide containing a 20 nucleotide (nt) palindromic sequence with a 3'-3' phosphodiester linkage between the $10^{th}$ and $11^{th}$ nt (bridging oligo 1 (SEQ ID NO: 5);

```
5'-CGA CUC UCG G-3'-3'-G GCU CUC AGC-5',
``` underlined bases OMeRNA) using T4 RNA ligase 1+PEG 8K and a DNA oligonucleotide "splint" complementary to the 3' UTR and bridging oligo 1 (splint oligo 1 (SEQ ID NO: 9); 5' CCG AGA GTC GAG CTT GAT GCA ACT TAA TTT TAT TAG G 3'; all bases DNA). To prepare the samples for ligation, bridging oligo 1 is 5'-end phosphorylated in a reaction containing 50 μM bridging oligo 1, 1 mM ATP, 1× PNK Buffer (NEB; 70 mM Tris-HCl, 10 mM MgCl$_2$, 5 mM DTT pH 7.6 at 25° C.) and 0.5 U/μL, T4 Polynucleotide Kinase (NEB) at 37° C. for 1 hour. Phosphorylated bridging oligo 1 is then desalted using a Sephadex G-25 desalting column (Princeton Separations) and hybridized to the transcript and splint in a reaction containing 3.2 μM capped hEPO transcript, 1.5 μM bridging oligo 1 and 3 μM splint oligo 1 by heating to 75° C. for 5 minutes followed by gradual cooling to room temperature over 5 minutes. An RNA ligation reaction is subsequently prepared to contain a 50% diluted hybridization reaction and 1× RNA ligase Buffer (NEB; 50 mM Tris-HCl, 10 mM MgCl$_2$, 1 mM DTT, pH 7.5 at 25° C.), 1 mM ATP, 10% PEG and 1 U/μL, T4 RNA ligase 1 (NEB), and is reacted for 90 minutes at 37° C. The completed ligation reaction is then purified using an RNeasy Mini Kit (Qiagen).

```
EPO PCNA #6 (includes internal 65A poly(A)
region):
                                        (SEQ ID NO: 22)
5'-GGACAGAUCGCCUGGAGACGCCAUCCACGCUGUUUUGACCUCCAUA

GAAGACACCGGGACCGAUCCAGCCUCCGCGGCCGGGAACGGUGCAUUGG

AACGCGGAUUCCCCGUGCCAAGAGUGACUCACCGUCCUUGACACGAUGG

GGGUGCACGAAUGUCCUGCCUGGCUGUGGCUUCUCCUGUCCUGCUGUC

GCUCCCUCUGGGCCUCCCAGUCCUGGGCGCCCCACCACGCCUCAUCUGU

GACAGCCGAGUCCUGGAGAGGUACCUCUUGGAGGCCAAGGAGGCCGAGA

AUAUCACGACGGGCUGUGCUGAACACUGCAGCUUGAAUGAGAAUAUCAC

UGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAG

CUGUCCUGCGGGGCCAGGCCCUGUUGGUCAACUCUUCCCAGCCGUGGGA

GCCCCUGCAGCUGCAUGUGGAUAAAGCCGUCAGUGGCCUUCGCAGCCUC

ACCACUCUGCUUCGGGCUCUGGGGAGCCCAGAAGGAAGCCAUCUCCCCUC
```

-continued
```
CAGAUGCGGCCUCAGCUGCUCCACUCCGAACAAUCACUGCUGACACUUU

CCGCAAACUCUUCCGAGUCUACUCCAAUUUCCUCCGGGGAAAGCUGAAG

CUGUACACAGGGGAGGCCUGCAGGACAGGGGACAGAUGACGGGUGGCAU

CCCUGUGACCCCUCCCCAGUGCCUCUCCUGGCCCUGGAAGUUGCCACUC

CAGUGCCCACCAAAAAAAAAAAAAAAAAAAAAAAAAAAAAAAAAAAAAA

AAAAAAAAAAAAAAAAAAAAAAAAAAGCCUUGUCCUAAUAAAAUUAAG

UUGCAUCAAGCUCGACUCUCGG-3'-PO₄-3'-GGCUCUCAGCUCGAAC

UACGUUGAAUUAAAAUAAUCCUGUUCCGAAAAAAAAAAAAAAAAAAAAA

AAAAAAAAAAAAAAAAAAAAAAAAAAAAAAAAAAAAAAAAAAAACCACC

CGUGACCUCACCGUUGAAGGUCCCGGUCCUCUCCGUGACCCCUCCCCAG

UGUCCCUACGGUGGGCAGUAGACAGGGGACAGGACGUCCGGAGGGGACA

CAUGUCGAAGUCGAAAGGGGCCUCCUUUAACCUCAUCUGAGCCUUCUCA

AACGCCUUUCACAGUCGUCACUAACAAGCCUCACCUCGUCGACUCCGGC

GUAGACCUCCCCUCUACCGAAGGAAGACCCGAGGGUCUCGGGCUUCGUC

UCACCACUCCGACGCUUCCGGUGACUGCCGAAAUAGGUGUACGUCGACG

UCCCCGAGGGUGCCGACCCUUCUCAACUGGUUGUCCCGGACCGGGGCGU

CCUGUCGAAGGCUGUCGUCCCGGUCCGGGACGGUCUGAAGAUGCCGGAC

GACGGGCUGGAGGUAGGAGAAGGUCCGUAUCUUUAAUUGAAACCACAGA

CCCUGUCACUAUAAGAGUAAGUUCGACGUCACAAGUCGUGUCGGGCAGC

ACUAUAAGAGCCGGAGGAACCGGAGGUUCUCCAUGGAGAGGUCCUGAGC

CGACAGUGUCUACUCCGCACCACCCCGCGGGUCCUGACCCUCCGGGUCU

CCCUCGCUGUCGUCCCUGUCCUCUUCGGUGUCGGUCCGUCCUGUAAGCA

CGUGGGGGUAGCACAGUUCCUGCCACUCAGUGAGAACCGUGCCCCUUAG

GCGCAAGGUUACGUGGCAAGGGCCGGCGCCUCCGACCUAGCCAGGGCCA

CAGAAGAUACCUCCAGUUUUGUCGCACCUACCGCAGAGGUCCGCUAGAC

AGG-5'
```

EPO PCNA #7

PCNA? (SEQ ID NO: 23) is prepared by splint ligation of the 3' end of two copies of an RNA encoding the human Erythropoietin (hEPO) protein to the 5' ends of a single oligonucleotide containing two 5' ends and a linked 3'-3' phosphodiester bond within the sequence. Briefly, a 5'-capped RNA containing a 5' untranslated region (UTR), a 3' UTR containing 3 stretches of 15 As and 1 stretch of 16 As with both UTRs flanking an RNA sequence encoding hEPO is transcribed using T7 RNA polymerase, enzymatically capped to contain a 5'-Cap 1 structure and purified. This hEPO transcript is then ligated in a single step to a OMeRNA "bridge" oligonucleotide containing a 20 nucleotide (nt) palindromic sequence with a 3'-3' phosphodiester linkage between the $10^{th}$ and $11^{th}$ nt (bridging oligo 1 (SEQ ID NO: 5);

```
5'-CGA CUC UCG G-3'-3'-G GCU CUC AGC-5',
``` underlined bases OMeRNA) using T4 RNA ligase 1+PEG 8K and a DNA oligonucleotide "splint" complementary to the 3'-UTR and bridging oligo 1 (splint oligo 1 (SEQ ID NO: 9); 5' CCG AGA GTC GAG CTT GAT GCA ACT TAA TTT TAT TAG G 3'; all bases DNA). To prepare the samples for ligation, oligo 1 is 5'-end phosphorylated in a reaction containing 50 μM bridging oligo 1, 1 mM ATP, 1× PNK Buffer (NEB; 70 mM Tris-HCl, 10 mM MgCl₂, 5 mM DTT, pH 7.6 at 25° C.) and 0.5 U/μL, T4 Polynucleotide Kinase (NEB) at 37° C. for 1 hour. Phosphorylated bridging oligo 1 is then desalted using a Sephadex G-25 desalting column (Princeton Separations) and hybridized to the transcript and splint in a reaction containing 3.2 μM capped hEPO transcript, 1.5 μM bridging oligo 1 and 3 μM splint oligo 1 by heating to 75° C. for 5 minutes followed by gradual cooling to room temperature over 5 minutes. An RNA ligation reaction is subsequently prepared to contain a 50% diluted hybridization reaction and 1× RNA ligase Buffer (NEB; 50 mM Tris-HCl, 10 mM MgCl₂, 1 mM DTT, pH 7.5 at 25° C.), 1 mM ATP, 10% PEG and 1 U/μL, T4 RNA ligase 1 (NEB), and is reacted for 90 min at 37° C. The completed ligation reaction is then purified using an RNeasy Mini Kit (Qiagen).

EPO PCNA #7 (includes multiple short internal poly(A) regions):
(SEQ ID NO: 23)
5'-GGACAGAUCGCCUGGAGACGCCAUCCACGCUGUUUUGACCUCCAUAG

AAGACACCGGGACCGAUCCAGCCUCCGCGGCCGGGAACGGUGCAUUGGAA

CGCGGAUUCCCCGUGCCAAGAGUGACUCACCGUCCUUGACACGAUGGGGG

UGCACGAAUGUCCUGCCUGGCUGUGGCUUCUCCUGUCCCUGCUGUCGCUC

CCUCUGGGCCUCCCAGUCCUGGGCGCCCCACCACGCCUCAUCUGUGACAG

CCGAGUCCUGGAGAGGUACCUCUUGGAGGCCAAGGAGGCCGAGAAUAUCA

CGACGGGCUGUGCUGAACACUGCAGCUUGAAUGAGAAUAUCACUGUCCCA

GACACCAAAGUUAAUUUCUAUGCCUGGAAGAGGAUGGAGGUCGGGCAGCA

GGCCGUAGAAGUCUGGCAGGGCCUGGCCCUGCUGUCGGAAGCUGUCCUGC

GGGGCCAGGCCCUGUUGGUCAACUCUUCCCAGCCGUGGGAGCCCCUGCAG

CUGCAUGUGGAUAAAGCCGUCAGUGGCCUUCGCAGCCUCACCACUCUGCU

UCGGGCUCUGGGAGCCCAGAAGGAAGCCAUCUCCCCUCCAGAUGCGGCCU

CAGCUGCUCCACUCCGAACAAUCACUGCUGACACUUUCCGCAAACUCUUC

CGAGUCUACUCCAAUUUCCUCCGGGGAAAGCUGAAGCUGUACACAGGGGA

GGCCUGCAGGACAGGGGACAGAUGACGGGUGGCAAAAAAAAAAAAAAUC

CCUGUGACCCCUCCCCAAAAAAAAAAAAAAAGUGCCUCUCCUGGCCCUG

GAAAAAAAAAAAAAAGUUGCCACUCCAGUGCCCACCAAAAAAAAAAAA

AAGCCUUGUCCUAAUAAAAUUAAGUUGCAUCAAGCU<u>CGACUCUCGG-</u>

<u>3'-PO₄-3'-GGCUCUCAGC</u>UCGAACUACGUUGAAUUAAAAUAAUCCUGU

UCCGAAAAAAAAAAAAAAACCACCCGUGACCUCACCGUUGAAAAAAAAA

AAAAAGGUCCCGGUCCUCUCCGUGAAAAAAAAAAAAAAACCCUCCCCA

GUGUCCCUAAAAAAAAAAAAAACGGUGGGCAGUAGACAGGGGACAGGAC

GUCCGGAGGGGACACAUGUCGAAGUCGAAAGGGGCCUCCUUUAACCUCAU

CUGAGCCUUCUCAAACGCCUUUCACAGUCGUCACUAACAAGCCUCACCUC

GUCGACUCCGGCGUAGACCUCCCCUCUACCGAAGGAAGACCCGAGGGUCU

CGGGCUUCGUCUCACCACUCCGACGCUUCCGGUGACUGCCGAAAUAGGUG

UACGUCGACGUCCCGAGGGUGCCGACCCUUCUCAACUGGUUGUCCCGGA

CCGGGGCGUCCUGUCGAAGGCUGUCGUCCCGGUCCGGGACGGUCUGAAGA

-continued
UGCCGGACGACGGGCUGGAGGUAGGAGAAGGUCCGUAUCUUUAAUUGAAA

CCACAGACCCUGUCACUAUAAGAGUAAGUUCGACGUCACAAGUCGUGUCG

GGCAGCACUAUAAGAGCCGGAGGAACCGGAGGUUCUCCAUGGAGAGGUCC

UGAGCCGACAGUGUCUACUCCGCACCACCCCGCGGGUCCUGACCCUCCGG

GUCUCCCUCGCUGUCGUCCCUGUCCUCUUCGGUGUCGGUCCGUCCUGUAA

GCACGUGGGGGUAGCACAGUUCCUGCCACUCAGUGAGAACCGUGCCCCUU

AGGCGCAAGGUUACGUGGCAAGGGCCGGCGCCUCCGACCUAGCCAGGGCC

ACAGAAGAUACCUCCAGUUUUGUCGCACCUACCGCAGAGGUCCGCUAGAC

AGG-5'

Figure 5:
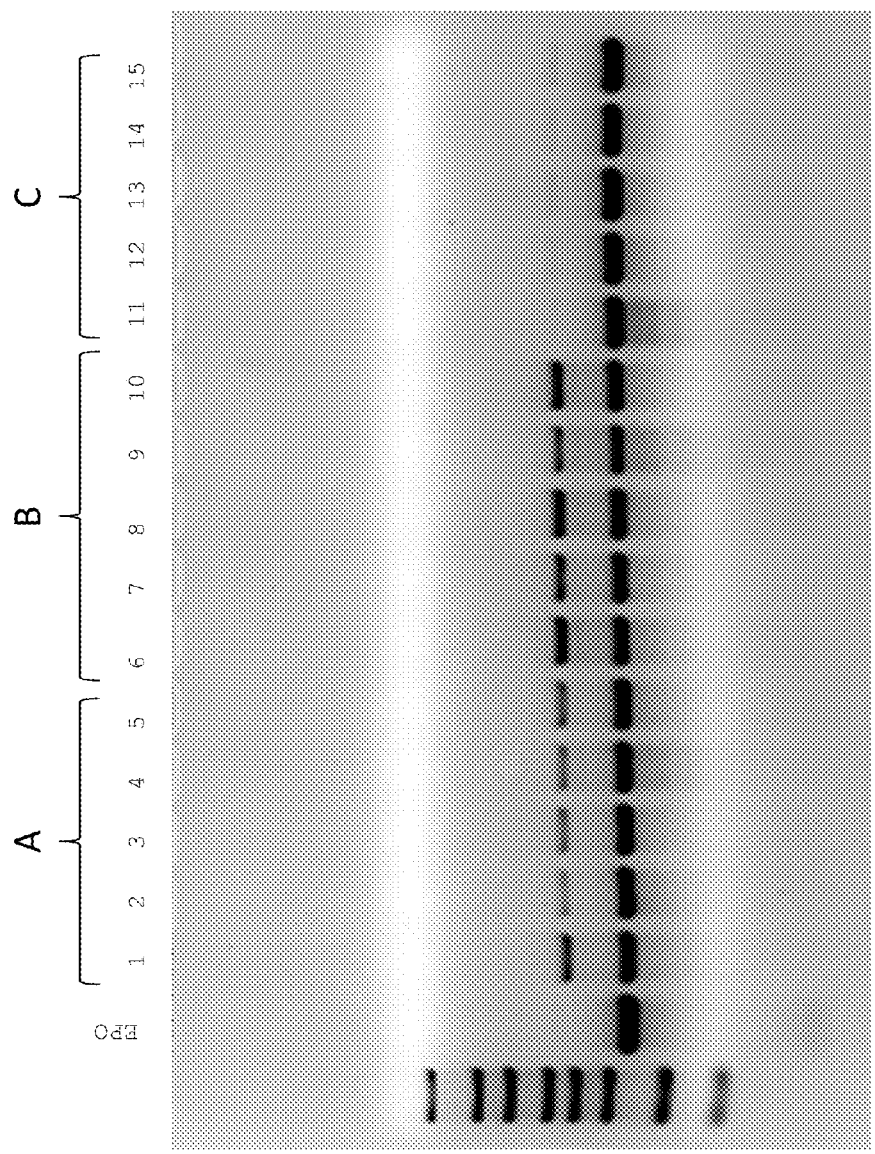
FIG. 5 shows exemplary results of synthesized EPO MCNA detected via gel electrophoresis. Constructs were synthesized under the following conditions: RNA Ligase 1 (A); RNA Ligase 1+10% PEG (B); and RNA Ligase 2 (C).

FIG. 5 shows the results of MCNA detected via gel electrophoresis. MCNA run in lanes 1-15 were the result of a ligation reaction comprising an EPO mRNA to bridging oligonucleotide to DNA splint (SEQ ID NO: 9) molar ratio of 2:1:2. The molar amounts of EPO mRNA and RNA ligase are included in the below table:

| Lane | EPO (μM) | Ligase (μM) |
|---|---|---|
| 1 | 1.7 | 2.25 RNA Ligase 1 |
| 2 | 1.7 | 0.6 RNA Ligase 1 |
| 3 | 0.85 | 0.6 RNA Ligase 1 |
| 4 | 0.425 | 0.6 RNA Ligase 1 |
| 5 | 0.2125 | 0.6 RNA Ligase 1 |
| 6 | 1.7 | 2.25 RNA Ligase 1 + 10% PEG |
| 7 | 1.7 | 0.6 RNA Ligase 1 + 10% PEG |
| 8 | 0.85 | 0.6 RNA Ligase 1 + 10% PEG |
| 9 | 0.425 | 0.6 RNA Ligase 1 + 10% PEG |
| 10 | 0.2125 | 0.6 RNA Ligase 1 + 10% PEG |
| 11 | 1.7 | 0.3 RNA Ligase 2 |
| 12 | 1.7 | 0.6 RNA Ligase 2 |
| 13 | 0.85 | 0.6 RNA Ligase 2 |
| 14 | 0.425 | 0.6 RNA Ligase 2 |
| 15 | 0.2125 | 0.6 RNA Ligase 2 |

FIG. 5 demonstrates that RNA Ligase 1 was superior to RNA Ligase 2 in producing MCNA comprising EPO RNA under the conditions tested. Further, the addition of 10% PEG to the reaction conditions enhanced ligation.

Figure 6:
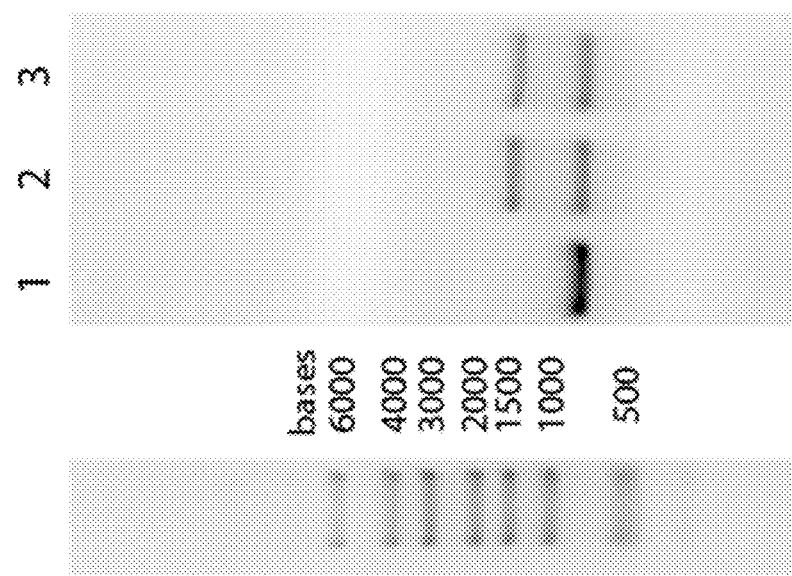
FIG. 6 shows exemplary results of synthesized EPO MCNA detected via gel electrophoresis. Lane 1 show capped EPO RNA with no tail. Lane 2 shows an EPO MCNA mixture with no DNAse treatment. Lane 3 shows an EPO MCNA mixture treated with DNAse.

FIG. 6 shows MCNA detected via gel electrophoresis. Lane 1 shows Capped EPO mRNA (no poly(A) tail). Lane 2 shows a MCNA mixture of full length MCNA ligation product mixed with unreacted/partially reacted EPO RNA product (with no DNAse treatment). Lane 3 shows a MCNA mixture of full length MCNA ligation product mixed with unreacted/partially reacted EPO RNA product (with DNAse treatment).

Figure 8:
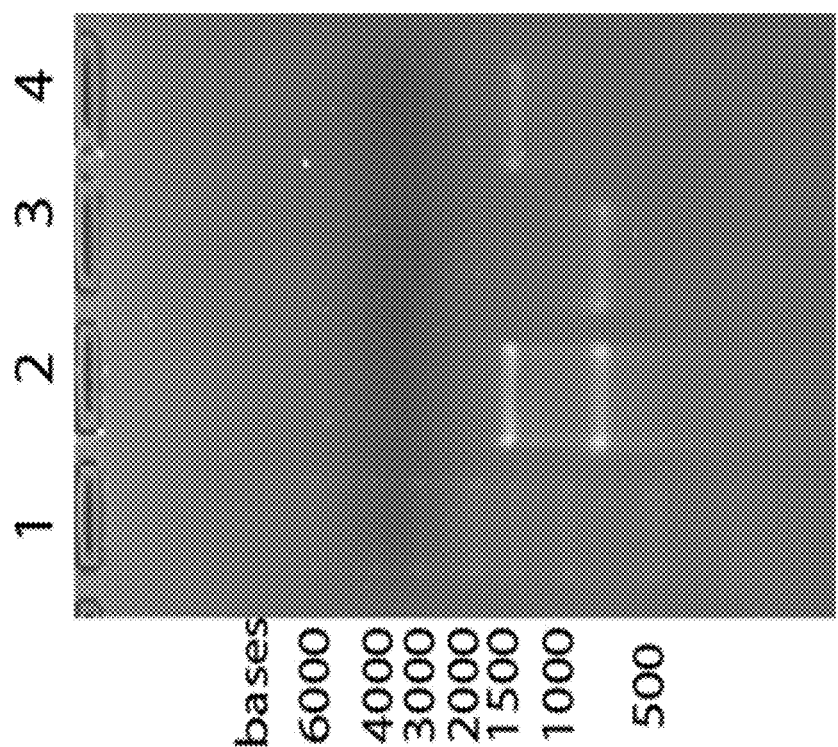
FIG. 8 shows exemplary results of synthesized EPO MCNA detected via gel electrophoresis. Lane 1 contains an RNA Ladder, Lane 2 contains a ligation product for EPO MCNA that was not purified, Lane 3 contains purified unreacted/partially reacted product and Lane 4 contains purified EPO MCNA ligation product.

FIG. 8 shows MCNA detected via gel electrophoresis. Lane 1 shows a RNA sizing ladder. Lane 2 shows a MCNA mixture of full length MCNA ligation product mixed with unreacted/partially reacted EPO RNA product. Lane 3 shows purified unreacted/partially reacted EPO RNA product. Lane 4 shows purified EPO MCNA ligation product.

MCNA-OTC Preparation

Figure 10:
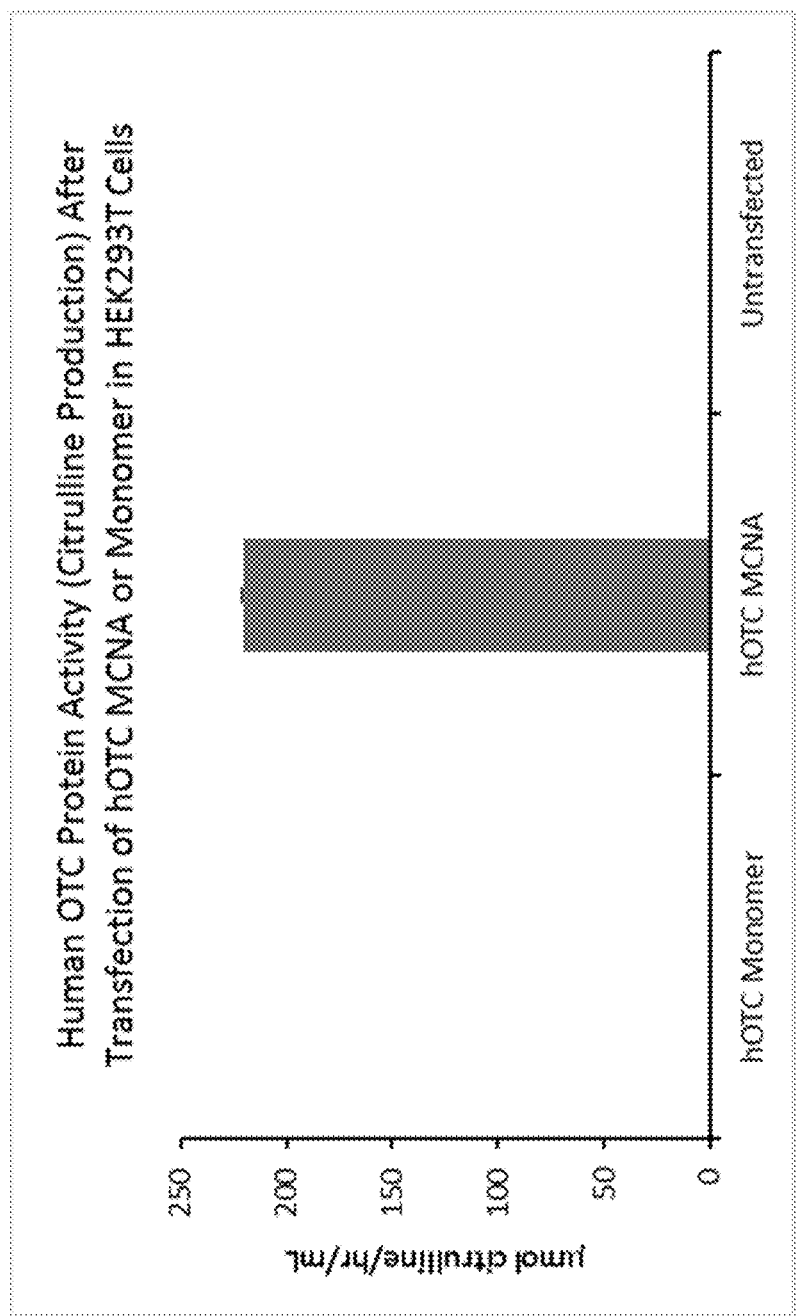
FIG. 10 shows an exemplary graph of the level of hOTC protein activity measured in cell lysate after transfection of HEK293T cells with synthetic constructs comprising untailed hOTC mRNA (hOTC monomer) or MCNA comprising hOTC mRNA.

MCNA-OTC comprising human Ornithine Transcarbamylase (hOTC) RNA (SEQ ID NO: 24) was prepared by splint ligation of the 3'-end of two copies of an RNA encoding the hOTC protein to the 5'-ends of a single oligonucleotide containing two 5' ends and a linked 3'-3' phosphodiester bond within the sequence. Briefly, a 5'-capped RNA containing a 5'-untranslated region (UTR) and a 3' UTR flanking an RNA sequence encoding hOTC was transcribed using RNA polymerase, enzymatically capped to contain a 5'-Cap 1 structure and purified. This hOTC transcript was then ligated in a single step to a 2'-hydroxymethylated RNA (OMeRNA) "bridge" oligonucleotide containing a 20 nucleotide (nt) palindromic sequence with a 3'-3' phosphodiester linkage between the 10$^{th}$ and 11$^{th}$ nt (oligo 1 (bridge) (SEQ ID NO: 5);

```
5'-CGA CUC UCG G-3'-3'-G GCU CUC AGC-5',
``` bold bases OMeRNA) using either T4 RNA ligase 1+PEG 8K and a DNA oligonucleotide "splint" complementary to the 3'-UTR and oligo 1 (oligo 2 (splint) (SEQ ID NO: 9); 5' CCG AGA GTC GAG CTT GAT GCA ACT TAA TTT TAT TAG G 3'; all bases DNA). To prepare the samples for ligation, oligo 1 was 5'-end phosphorylated in a reaction containing 50 μM oligo 1, 1 mM ATP, 1× PNK Buffer (NEB; 70 mM Tris-HCl, 10 mM MgCl$_2$, 5 mM DTT pH 7.6 at 25° C.) and 0.5 U/μL T4 Polynucleotide Kinase (NEB) at 37° C. for 1 hour. Phosphorylated oligo 1 (bridge) was then desalted using a Sephadex G-25 desalting column (Princeton Separations) and hybridized to the transcript and splint in a reaction containing 3.3 μM capped hOTC transcript, 1.5 μM oligo 1 and 3.3 μM oligo 2 by heating to 75° C. for 5 minutes, followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT pH 7.5 at 25° C.), 1 mM ATP, 10% PEG and 0.33 U/μL T4 RNA ligase 1. Each was reacted for 60 minutes at 37° C. The completed ligation reaction was then reacted with DNase I and subsequently purified using an RNeasy Maxi Kit (Qiagen). The reaction products were evaluated for ligation efficiency using TBE/agarose gel electrophoresis. The isolated MCNA-OTC product was equilibrated with Lipofectamine and transfected into adherent HEK293 cells. Unfractionated cell lysate was then assayed for citrulline production from ornithine and carbamoyl phosphate (FIG. 10).

```
MCNA-OTC
                                          (SEQ ID NO: 24)
5'-GGACAGAUCGCCUGGAGACGCCAUCCACGCUGUUUUGACCUCCAUAG

AAGACACCGGGACCGAUCCAGCCUCCGCGGCCGGGAACGGUGCAUUGGAA

CGCGGAUUCCCCGUGCAAGAGUGACUCACCGUCCUUGACACGAUGCUGU

UCAACCUUCGGAUCUUGCUGAACAACGCUGCGUUCCGGAAUGGUCACAAC

UUCAUGGUCCGGAACUUCAGAUGCGGCCAGCCGCUCCAGAACAAGGUGCA

GCUCAAGGGGAGGGACCUCCUCACCCUGAAAAACUUCACCGGAGAAGAGA

UCAAGUACAUGCUGUGGCUGUCAGCCGACCUCAAAUUCCGGAUCAAGCAG

AAGGGCGAAUACCUUCCUUUGCUGCAGGGAAAGUCCCUGGGGAUGAUCUU

CGAGAAGCGCAGCACUCGCACUAGACUGUCAACUGAAACCGGCUUCGCGC

UGCUGGGAGGACACCCCUGCUUCCUGACCACCCAAGAUAUCCAUCUGGGU

GUGAACGAAUCCCUCACCGACACAGCGCGGGUGCUGUCGUCCAUGGCAGA

CGCGGUCCUCGCCCGCGUGUACAAGCAGUCUGAUCUGGACACUCUGGCCA

AGGAAGCCUCCAUUCCUAUCAUUAAUGGAUUGUCCGACCUCUACCAUCCC

AUCCAGAUUCUGGCCGAUUAUCUGACUCUGCAAGAACAUUACAGCUCCCU

GAAGGGGCUUACCCUUUCGUGGAUCGGCGACGGCAACAACAUUCUGCACA

GCAUUAUGAUGAGCGCUGCCAAGUUUGGAAUGCACCUCCAAGCAGCGACC

CCGAAGGGAUACGAGCCAGACGCCUCCGUGACGAAGCUGGCUGAGCAGUA

CGCCAAGGAGAACGGCACUAAGCUGCUGCUCACCAACGACCCUCUCGAAG

CCGCCCACGGUGGCAACGUGCUGAUCACCGAUACCUGGAUCUCCAUGGGA

CAGGAGGAGGAAAAGAAGAAGCGCCUGCAAGCAUUUCAGGGGUACCAGGU

GACUAUGAAAACCGCCAAGGUCGCCGCCUCGGACUGGACCUUCUUGCACU

GUCUGCCCAGAAAGCCCGAAGAGGUGGACGACGAGGUGUUCUACAGCCCG

CGGUCGCUGGUCUUUCCGGAGGCCGAAAACAGGAAGUGGACUAUCAUGGC

CGUGAUGGUGUCCCUGCUGACCGAUUACUCCCCGCAGCUGCAGAAACCAA

AGUUCUGACGGGUGGCAUCCCUGUGACCCCUCCCCAGUGCCUCUCCUGGC

CCUGGAAGUUGCCACUCCAGUGCCCACCAGCCUUGUCCUAAUAAAAUUAA

GUUGCAUCAAGCUCGACUCUCGG-3'-PO$_3$-3'-GGCUCUCAGC

UCGAACUACGUUGAAUUAAAAUAAUCCUGUUCCGACCACCCGUGACCUCA

CCGUUGAAGGUCCCGGUCCUCUCCGUGACCCCUCCCCAGUGUCCCUACGG

UGGGCAGUCUUGAAACCAAAGACGUCGACGCCCCUCAUUAGCCAGUCGUC

CCUGUGGUAGUGCCGGUACUAUCAGGUGAAGGACAAAAGCCGGAGGCCUU

UCUGGUCGCUGGCGCCCGACAUCUUGUGGAGCAGCAGGUGGAGAAGCCCG

AAAGACCCGUCUGUCACGUUCUUCCAGGUCAGGCUCCGCCGCUGGAACCG

CCAAAAGUAUCAGUGGACCAUGGGGACUUUACGAACGUCCGCGAAGAAGA

AAAGGAGGAGGACAGGGUACCUCUAGGUCCAUAGCCACUAGUCGUGCAAC

GGUGGCACCCGCCGAAGCUCUCCCAGCAACCACUCGUCGUCGAAUCACGG

CAAGAGGAACCGCAUGACGAGUCGGUCGAAGCAGUGCCUCCGCAGACCGA

GCAUAGGGAAGCCCCAGCGACGAACCUCCACGUAAGGUUUGAACCGUCGC

GAGUAGUAUUACGACACGUCUUACAACAACGGCAGCGGCUAGGUGCUUUC

CCAUUCGGGGAAGUCCCUCGACAUUACAAGAACGUCUCAGUCUAUUAGCC

GGUCUUAGACCUACCCUACCAUCUCCAGCCUGUUAGGUAAUUACUAUCCU

UACCUCCGAAGGAACCGGUCUCACAGGUCUAGUCUGACGAACAUGUGCGC

CCGCUCCUGGCGCAGACGGUACCUGCUGUCGUGGGCGCGACACAGCCACU

CCCUAAGCAAGUGUGGGUCUACCUAUAGAACCCACCAGUCCUUCGUCCCC

ACAGGAGGGUCGUCGCGCUUCGGCCAAAGUCAACUGUCAGAUCACGCUCA

CGACGCGAAGAGCUUCUAGUAGGGUCCCUGAAAGGGACGUCGUUUCCUU

CCAUAAGCGGGAAGACGAACUAGGCCUUAAACUCCAGCCGACUGUCGGUG

UCGUACAUGAACUAGAGAAGAGGCCACUUCAAAAAGUCCACUCCUCCAG

GGAGGGAACUCGACGUGGAACAAGACCUCGCCGACCGGCGUAGACUUCA

AGGCCUGGUACUUCAACACUGGUAAGGCCUUGCGUCGCAACAAGUCGUUC

UAGGCUUCCAACUUGUCGUAGCACAGUUCCUGCCACUCAGUGAGAACCGU

GCCCCUUAGGCGCAAGGUUACGUGGCAAGGGCCGGCGCUCCGACCUAGC

CAGGGCCACAGAAGAUACCUCCAGUUUUGUCGCACCUACCGCAGAGGUCC

GCUAGACAGG-5'
(Bold base are OMeRNA)
```

MCNA-PAH Preparation

Figure 11:
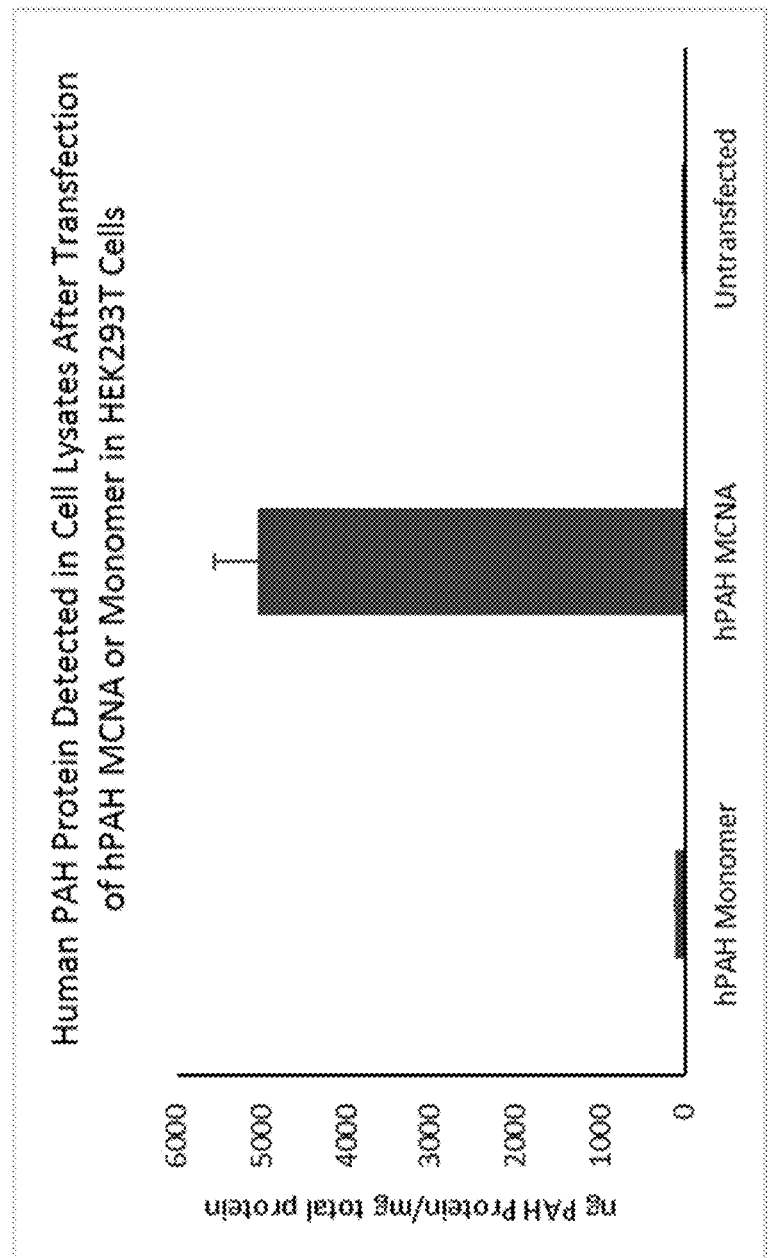
FIG. 11 shows an exemplary graph of the level of hPAH protein produced after transfection of HEK293T cells with synthetic constructs comprising untailed hPAH mRNA (hPAH monomer) or MCNA comprising hPAH mRNA.

MCNA-PAH comprising human Phenylalanine Hydroxylase (hPAH) RNA (SEQ ID NO: 25) was prepared by splint ligation of the 3'-end of two copies of an RNA encoding the hPAH protein to the 5'-ends of a single oligonucleotide containing two 5' ends and a linked 3'-3' phosphodiester bond within the sequence. Briefly, a 5'-capped RNA containing a 5'-untranslated region (UTR) and a 3' UTR flanking an RNA sequence encoding hPAH was transcribed using RNA polymerase, enzymatically capped to contain a 5'-Cap 1 structure and purified. This hPAH transcript was then ligated in a single step to a 2'-hydroxymethylated RNA (OMeRNA) "bridge" oligonucleotide containing a 20 nucleotide (nt) palindromic sequence with a 3'-3' phosphodiester linkage between the 10$^{th}$ and 11$^{th}$ nt (oligo 1 (bridge)) (SEQ ID NO: 5);

5'-CGA CUC UCG G-3'-3'-G GCU CUC AGC-5', bold bases OMeRNA) using either T4 RNA ligase 1+PEG 8K and a DNA oligonucleotide "splint" complementary to the 3'-UTR and oligo 1 (oligo 2 (splint) (SEQ ID NO: 9); 5' CCG AGA GTC GAG CTT GAT GCA ACT TAA TTT TAT TAG G 3'; all bases DNA). To prepare the samples for ligation, oligo 1 was 5'-end phosphorylated in a reaction containing 50 µM oligo 1, 1 mM ATP, 1× PNK Buffer (NEB; 70 mM Tris-HCl, 10 mM MgCl$_2$, 5 mM DTT pH 7.6 at 25° C.) and 0.5 U/µL T4 Polynucleotide Kinase (NEB) at 37° C. for 1 hour. Phosphorylated oligo 1 (bridge) was then desalted using a Sephadex G-25 desalting column (Princeton Separations) and hybridized to the transcript and splint in a reaction containing 2.7 µM capped hPAH transcript, 1.2 µM oligo 1 and 2.7 µM oligo 2 by heating to 75° C. for 5 minutes, followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT pH 7.5 at 25° C.), 1 mM ATP, 10% PEG and 0.33 U/µL T4 RNA ligase 1. Each was reacted for 60 minutes at 37° C. The completed ligation reaction was then reacted with DNase I and subsequently purified using an RNeasy Maxi Kit (Qiagen). The reaction products were evaluated for ligation efficiency using TBE/agarose gel electrophoresis. The isolated MCNA-PAH reaction product was equilibrated with Lipofectamine and transfected into adherent HEK293 cells. Unfractionated cell lysate was then assayed for PAH protein expression using a PAH-specific ELISA (FIG. 11).

MCNA-PAH
(SEQ ID NO: 25)
5'-GGACAGAUCGCCUGGAGACGCCAUCCACGCUGUUUUGACCUCCAUAG

AAGACACCGGGACCGAUCCAGCCUCCGCGGCCGGGAACGGUGCAUUGGAA

CGCGGAUUCCCCGUGCCAAGAGUGACUCACCGUCCUUGACACGAUGAGCA

CCGCCGUGCUGGAGAACCCCGGCCUGGGCGCAAGCUGAGCGACUUCGGC

CAGGAGACCAGCUACAUCGAGGACAACUGCAACCAGAACGGCGCCAUCAG

CCUGAUCUUCAGCCUGAAGGAGGAGGUGGGCGCCCUGGCCAAGGUGCUGC

GCCUGUUCGAGGAGAACGACGUGAACCUGACCCACAUCGAGAGCCGCCCC

AGCCGCCUGAAGAAGGACGAGUACGAGUUCUUCACCCACCUGGACAAGCG

CAGCCUGCCCGCCCUGACCAACAUCAUCAAGAUCCUGCGCCACGACAUCG

GCGCCACCGUGCACGAGCUGAGCCGCGACAAGAAGAAGGACACCGUGCCC

UGGUUCCCCCGCACCAUCCAGGAGCUGGACCGCUUCGCCAACCAGAUCCU

GAGCUACGGCGCCGAGCUGGACGCCGACCACCCCGGCUUCAAGGACCCCG

UGUACCGCGCCCGCCGCAAGCAGUUCGCCGACAUCGCCUACAACUACCGC

CACGGCCAGCCCAUCCCCCGCGUGGAGUACAUGGAGGAGGAGAAGAAGAC

CUGGGGCACCGUGUUCAAGACCCUGAAGAGCCUGUACAAGACCCACGCCU

GCUACGAGUACAACCACAUCUUCCCCCUGCUGGAGAAGUACUGCGGCUUC

CACGAGGACAACAUCCCCCAGCUGGAGGACGUGAGCCAGUUCCUGCAGAC

CUGCACCGGCUUCCGCCUGCGCCCCGUGGCCGGCCUGCUGAGCAGCCGCG

ACUUCCUGGGCGGCCUGGCCUUCCGCGUGUUCCACUGCACCCAGUACAUC

CGCCACGGCAGCAAGCCCAUGUACACCCCCGAGCCCGACAUCUGCCACGA

GCUGCUGGGCCACGUGCCCCUGUUCAGCGACCGCAGCUUCGCCCAGUUCA

GCCAGGAGAUCGGCCUGGCCAGCCUGGGCGCCCCCGACGAGUACAUCGAG

AAGCUGGCCACCAUCUACUGGUUCACCGUGGAGUUCGGCCUGUGCAAGCA

GGGCGACAGCAUCAAGGCCUACGGCGCCGGCCUGCUGAGCAGCUUCGGCG

AGCUGCAGUACUGCCUGAGCGAGAAGCCCAAGCUGCUGCCCCUGGAGCUG

GAGAAGACCGCCAUCCAGAACUACACCGUGACCGAGUUCCAGCCCCUGUA

CUACGUGGCCGAGAGCUUCAACGACGCCAAGGAGAAGGUGCGCAACUUCG

CCGCCACCAUCCCCCGCCCCUUCAGCGUGCGCUACGACCCCUACACCCAG

CGCAUCGAGGUGCUGGACAACACCCAGCAGCUGAAGAUCCUGGCCGACAG

CAUCAACAGCGAGAUCGGCAUCCUGUGCAGCGCCCUGCAGAAGAUCAAGU

AACGGGUGGCAUCCCUGUGACCCCUCCCCAGUGCCUCUCCUGGCCCUGGA

AGUUGCCACUCCAGUGCCCACCAGCCUUGUCCUAAUAAAAUUAAGUUGCA

UCAAGCUCGACUCUCGG-3'-PO$_4$-3'-GGCUCUCAGCUCGAACUACGUU

GAAUUAAAAUAAUCCUGUUCCGACCACCCGUGACCUCACCGUUGAAGGUC

CCGGUCCUCUCCGUGACCCCUCCCCAGUGUCCCUACGGUGGGCAAUGAAC

UAGAAGACGUCCCGCGACGUGUCCUACGGCUAGAGCGACAACUACGACAG

CCGGUCCUAGAAGUCGACGACCCACAACAGGUCGUGGAGCUACGCGACCC

ACAUCCCCAGCAUCGCGUGCGACUUCCCCGCCCCCUACCACCGCCGCUUC

AACGCGUGGAAGAGGAACCGCAGCAACUUCGAGAGCCGGUGCAUCAUGUC

CCCGACCUUGAGCCAGUGCCACAUCAAGACCUACCGCCAGAAGAGGUCGA

GGUCCCGUCGUCGAACCCGAAGAGCGAGUCCGUCAUGACGUCGAGCGGC

UUCGACGAGUCGUCCGGCCGCGGCAUCCGGAACUACGACAGCGGGACGAA

CGUGUCCGGCUUGAGGUGCCACUUGGUCAUCUACCACCGGUCGAAGAGCU

ACAUGAGCAGCCCCGCGGGUCCGACCGGUCCGGCUAGAGGACCGACUUG

ACCCGCUUCGACGCCAGCGACUUGUCCCCGUGCACCGGGUCGUCGAGCAC

CGUCUACAGCCCGAGCCCCACAUGUACCCGAACGACGGCACCGCCUACA

UGACCCACGUCACCUUGUGCGCCUUCCGGUCCGGCGGGUCCUUCAGCGCC

GACGAGUCGUCCGGCCGGUGCCCCGCGUCCGCCUUCGGCCACGUCCAGAC

GUCCUUGACCGAGUGCAGGAGGUCGACCCCCUACAACAGGAGCACCUUCG

GCGUCAUGAAGAGGUCGUCCCCCUUCUACACCAACAUGAGCAUCGUCCGC

-continued
ACCCAGAACAUGUCCGAGAAGUCCCAGAACUUGUGCCACGGGGUCCAGAA

GAAGAGGAGGAGGUACAUGAGGUGCGCCCCCUACCCGACCGGCACCGCCA

UCAACAUCCGCUACAGCCGCUUGACGAACGCCGCCCGCGCCAUGUGCCCC

AGGAACUUCGGCCCCACCAGCCGCAGGUCGAGCCGCGGCAUCGAGUCCUA

GACCAACCGCUUCGCCAGGUCGAGGACCUACCACGCCCCUUGGUCCCGU

GCCACAGGAAGAAGAACAGCGCCGAGUCGAGCACGUGCCACCGCGGCUAC

AGCACCGCGUCCUAGAACUACUACAACCAGUCCCGCCCGUCCGACGCGAA

CAGGUCCACCCACUUCUUGAGCAUGAGCAGGAAGAAGUCCGCCGACCCCG

CCGAGAGCUACACCCAGUCCAAGUGCAGCAAGAGGAGCUUGUCCGCGUCG

UGGAACCGGUCCCGCGGGUGGAGGAGGAAGUCCGACUUCUAGUCCGACUA

CCGCGGCAAGACCAACGUCAACAGGAGCUACAUCGACCAGAGGACCGGCU

UCAGCGAGUCGAACGCCGGGUCCGGCCCCAAGAGGUCGUGCCGCCACGAG

UAGCACAGUUCCUGCCACUCAGUGAGAACCGUGCCCCUUAGGCGCAAGGU

UACGUGGCAAGGGCCGGCGCCUCCGACCUAGCCAGGGCCACAGAAGAUAC

CUCCAGUUUUGUCGCACCUACCGCAGAGGUCCGCUAGACAGG-5'
(Bold base are OMeRNA)

MCNA-CFTR Preparation

Figure 12:
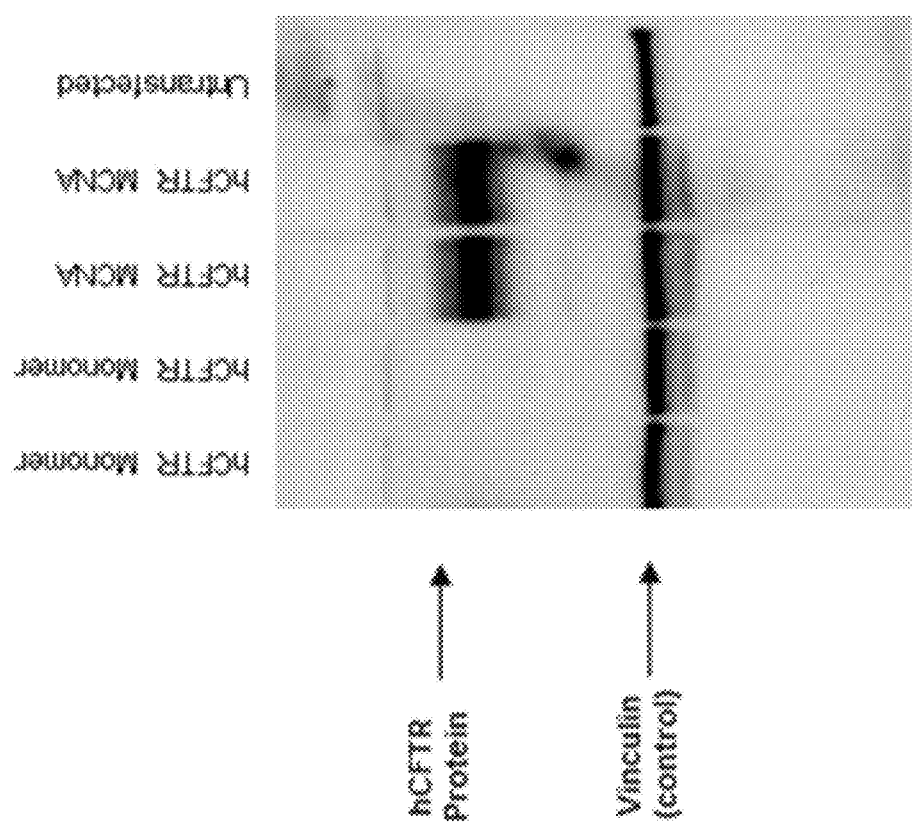
FIG. 12 shows an exemplary Western blot demonstrating hCFTR protein production after transfection of HEK293T cells with synthetic constructs comprising untailed hCFTR mRNA (hCFTR monomer) or MCNA comprising hCFTR mRNA.

MCNA-CFTR comprising human Cystic Fibrosis Transmembrane Conductance Regulator (hCFTR) RNA (SEQ ID NO: 26) was prepared by splint ligation of the 3'-end of two copies of an RNA encoding the hCFTR protein to the 5'-ends of a single oligonucleotide containing two 5' ends and a linked 3'-3' phosphodiester bond within the sequence. Briefly, a 5'-capped RNA containing a 5'-untranslated region (UTR) and a 3' UTR flanking an RNA sequence encoding hCFTR was transcribed using RNA polymerase, enzymatically capped to contain a 5'-Cap 1 structure and purified. This hCFTR transcript was then ligated in a single step to a 2'-hydroxymethylated RNA (OMeRNA) "bridge" oligonucleotide containing a 20 nucleotide (nt) palindromic sequence with a 3'-3' phosphodiester linkage between the 10$^{th}$ and 11$^{th}$ nt (oligo 1 (bridge) (SEQ ID NO: 5);

5'-CGA CUC UCG G-3'-3'-G GCU CUC AGC-5', bold bases OMeRNA) using either T4 RNA ligase 1+PEG 8K and a DNA oligonucleotide "splint" complementary to the 3'-UTR and oligo 1 (oligo 2 (splint) (SEQ ID NO: 9); 5' CCG AGA GTC GAG CTT GAT GCA ACT TAA TTT TAT TAG G 3'; all bases DNA). To prepare the samples for ligation, oligo 1 was 5'-end phosphorylated in a reaction containing 50 µM oligo 1, 1 mM ATP, 1× PNK Buffer (NEB; 70 mM Tris-HCl, 10 mM MgCl$_2$, 5 mM DTT pH 7.6 at 25° C.) and 0.5 U/µL T4 Polynucleotide Kinase (NEB) at 37° C. for 1 hour. Phosphorylated oligo 1 (bridge) was then desalted using a Sephadex G-25 desalting column (Princeton Separations) and hybridized to the transcript and splint in a reaction containing 0.92 µM capped hCFTR transcript, 0.42 µM oligo 1 and 0.92 µM oligo 2 by heating to 75° C. for 5 minutes followed by gradual cooling to room temperature over 5 minutes. An RNA ligation reaction was subsequently prepared to contain a 50% diluted hybridization reaction and 1× RNA ligase Buffer (NEB; 50 mM Tris-HCl, 10 mM MgCl$_2$, 1 mM DTT pH 7.5 at 25° C.), 1 mM ATP, 10% PEG and 0.33 U/µL T4 RNA ligase 1. Each was reacted for 60 minutes at 37° C. The completed ligation reaction was then reacted with DNase I and subsequently purified using an RNeasy Maxi Kit (Qiagen). The reaction products were evaluated for ligation efficiency using TBE/agarose gel electrophoresis. The isolated MCNA-CFTR product was equilibrated with Lipofectamine and transfected into adherent HEK293 cells. Unfractionated cell lysate was then assayed for CFTR protein expression using CFTR-specific Western Blotting (FIG. 12).

MCNA-CFTR
(SEQ ID NO: 26)
5'-GGACAGAUCGCCUGGAGACGCCAUCCACGCUGUUUUGACCUCCAUAG

AAGACACCGGGACCGAUCCAGCCUCCGCGGCCGGGAACGGUGCAUUGGAA

CGCGGAUUCCCCGUGCCAAGAGUGACUCACCGUCCUUGACACGAUGCAAC

GCUCUCCUCUUGAAAAGGCCUCGGUGGUGUCCAAGCUCUUCUUCUCGUGG

ACUAGACCCAUCCUGAGAAAGGGGUACAGACAGCGCUUGGAGCUGUCCGA

UAUCUAUCAAAUCCCUUCCGUGGACUCCGCGGACAACCUGUCCGAGAAGC

UCGAGAGAAUGGGACAGAGAACUCGCCUCAAAGAAGAACCCGAAGCUG

AUUAAUGCGCUUAGGCGGUGCUUUUUCUGGCGGUUCAUGUUCUACGGCAU

CUUCCUCUACCUGGGAGAGGUCACCAAGGCCGUGCAGCCCCUGUUGCUGG

GACGGAUUAUUGCCUCCUACGACCCCGACAACAAGGAAGAAAGAAGCAUC

GCUAUCUACUUGGGCAUCGGUCUGUGCCUGCUUUUCAUCGUCCGGACCCU

CUUGUUGCAUCCUGCUAUUUUCGGCCUGCAUCACAUUGGCAUGCAGAUGA

GAAUUGCCAUGUUUUCCCUGAUCUACAAGAAAACUCUGAAGCUCUCGAGC

CGCGUGCUUGACAAGAUUUCCAUCGGCCAGCUCGUGUCCCUGCUCUCCAA

CAAUCUGAACAAGUUCGACGAGGGCCUCGCCCUGGCCCACUUCGUGUGGA

UCGCCCCUCUGCAAGUGGCGCUUCUGAUGGGCCUGAUCUGGGAGCUGCUG

CAAGCCUCGGCAUUCUGUGGGCUUGGAUUCCUGAUCGUGCUGGCACUGUU

CCAGGCCGGACUGGGGCGGAUGAUGAUGAAGUACAGGGACCAGAGAGCCG

GAAAGAUUUCCGAACGGCUGGUGAUCACUUCGGAAAUGAUCGAAAACAUC

CAGUCAGUGAAGGCCUACUGCUGGGAAGAGGCCAUGGAAAAGAUGAUUGA

AAACCUCCGGCAAACCGAGCUGAAGCUGACCCGCAAGGCCGCUUACGUGC

GCUAUUUCAACUCGUCCGCUUUCUUCUUCUCCGGGUUCUUCGUGGUGUUU

CUCUCCGUGCUCCCCUACGCCCUGAUUAAGGGAAUCAUCCUCAGGAAGAU

CUUCACCACCAUUUCCUUCUGUAUCGUGCUCCGCAUGGCCGUGACCCGGC

AGUUCCCAUGGGCCGUGCAGACUUGGUACGACUCCCUGGGAGCCAUUAAC

AAGAUCCAGGACUUCCUUCAAAAGCAGGAGUACAAGACCCUCGAGUACAA

CCUGACUACUACCGAGGUCGUGAUGGAAAACGUCACCGCCUUUUGGGAGG

AGGGAUUUGGCGAACUGUUCGAGAAGGCCAAGCAGAACAACAACAACCGC

AAGACCUCGAACGGUGACGACUCCCUCUUCUUUUCAAACUUCAGCCUGCU

CGGGACGCCCGUGCUGAAGGACAUUAACUUCAAGAUCGAAAGAGGACAGC

UCCUGGCGGUGGCCGGAUCGACCGGAGCCGGAAAGACUUCCCUGCUGAUG

GUGAUCAUGGGAGAGCUUGAACCUAGCGAGGGAAAGAUCAAGCACUCCGG

CCGCAUCAGCUUCUGUAGCCAGUUUUCCUGGAUCAUGCCCGGAACCAUUA

AGGAAAACAUCAUCUUCGGCGUGUCCUACGAUGAAUACCGCUACCGGUCC

-continued

GUGAUCAAAGCCUGCCAGCUGGAAGAGGAUAUUUCAAAGUUCGCGGAGAA
AGAUAACAUCGUGCUGGGCGAAGGGGGUAUUACCUUGUCGGGGGCCAGC
GGGCUAGAAUCUCGCUGGCCAGAGCCGUGUAUAAGGACGCCGACCUGUAU
CUCCUGGACUCCCCCUUCGGAUACCUGGACGUCCUGACCGAAAAGGAGAU
CUUCGAAUCGUGCGUGUGCAAGCUGAUGGCUAACAAGACUCGCAUCCUCG
UGACCUCCAAAAUGGAGCACCUGAAGAAGGCAGACAAGAUUCUGAUUCUG
CAUGAGGGGUCCUCCUACUUUUACGGCACCUUCUCGGAGUUGCAGAACUU
GCAGCCCGACUUCUCAUCGAAGCUGAUGGGUUGCGACAGCUUCGACCAGU
UCUCCGCCGAAAGAAGGAACUCGAUCCUGACGGAAACCUUGCACCGCUUC
UCUUUGGAAGGCGACGCCCCUGUGUCAUGGACCGAGACUAAGAAGCAGAG
CUUCAAGCAGACCGGGGAAUUCGGCGAAAAGAGGAAGAACAGCAUCUUGA
ACCCCAUUAACUCCAUCCGCAAGUUCUCAAUCGUGCAAAAGACGCCACUG
CAGAUGAACGGCAUUGAGGAGGACUCCGACGAACCCCUUGAGAGGCGCCU
GUCCCUGGUGCCGGACAGCGAGCAGGGAGAAGCCAUCCUGCCUCGGAUUU
CCGUGAUCUCCACUGGUCCGACGCUCCAAGCCCGGCGGCGGCAGUCCGUG
CUGAACCUGAUGACCCACAGCGUGAACCAGGGCCAAAACAUUCACCGCAA
GACUACCGCAUCCACCCGGAAAGUGCCCUGGCACCUCAAGCGAAUCUUA
CCGAGCUCGACAUCUACUCCCGGAGACUGUCGCAGGAAACCGGGCUCGAA
AUUUCCGAAGAAAUCAACGAGGAGGAUCUGAAAGAGUGCUUCUUCGACGA
UAUGGAGUCGAUACCCGCCGUGACGACUUGGAACACUUAUCUGCGGUACA
UCACUGUGCACAAGUCAUUGAUCUUCGUGCUGAUUUGGUGCCUGGUGAUU
UUCCUGGCCGAGGUCGCGGCCUCACUGGUGGUGCUCUGGCUGUUGGGAAA
CACGCCUCUGCAAGACAAGGGAAACUCCACGCACUCGAGAAACAACAGCU
AUGCCGUGAUUAUCACUUCCACCUCCUCUUAUUACGUGUUCUACAUCUAC
GUCGGAGUGGCGGAUACCCUGCUCGCGAUGGGUUUCUUCAGAGGACUGCC
GCUGGUCCACACCUUGAUCACCGUCAGCAAGAUUCUUCACCACAAGAUGU
UGCAUAGCGUGCUGCAGGCCCCCAUGUCCACCCUCAACACUCUGAAGGCC
GGAGGCAUUCUGAACAGAUUCUCCAAGGACAUCGCUAUCCUGGACGAUCU
CCUGCCGCUUACCAUCUUUGACUUCAUCCAGCUGCUGCUGAUCGUGAUUG
GAGCAAUCGCAGUGGUGGCGGUGCUGCAGCCUUACAUUUUCGUGGCCACU
GUGCCGGUCAUUGUGGCGUUCAUCAUGCUGCGGGCCUACUUCCUCCAAAC
CAGCCAGCAGCUGAAGCAACUGGAAUCCGAGGGACGAUCCCCCAUCUUCA
CUCACCUUGUGACGUCGUUGAAGGGACUGUGGACCCUCCGGGCUUUCGGA
CGGCAGCCCUACUUCGAAACCCUCUUCCACAAGGCCCUGAACCUCCACAC
CGCCAAUUGGUUCCUGUACCUGUCCACCCUGCGGUGGUUCCAGAUGCGCA
UCGAGAUGAUUUUCGUCAUCUUCUUCAUCGCGGUCACAUUCAUCAGCAUC
CUGACUACCGGAGAGGGAGAGGGACGGGUCGGAAUAAUCCUGACCCUCGC
CAUGAACAUUAUGAGCACCCUGCAGUGGGCAGUGAACAGCUCGAUCGACG
UGGACAGCCUGAUGCGAAGCGUCAGCCGCGUGUUCAAGUUCAUCGACAUG
CCUACUGAGGGAAAACCCACUAAGUCCACUAAGCCCUACAAAAAUGGCCA
GCUGAGCAAGGUCAUGAUCAUCGAAAACUCCCACGUGAAGAAGGACGAUA

-continued

UUUGGCCCUCCGGAGGUCAAAUGACCGUGAAGGACCUGACCGCAAAGUAC
ACCGAGGGAGGAAACGCCAUUCUCGAAAACAUCAGCUUCUCCAUUUCGCC
GGGACAGCGGGUCGGCCUUCUCGGGCGGACCGGUUCCGGGAAGUCAACUC
UGCUGUCGGCUUUCCUCCGGCUGCUGAAUACCGAGGGGGAAAUCCAAAUU
GACGGCGUGUCUUGGGAUUCCAUUACUCUGCAGCAGUGGCGGAAGGCCUU
CGGCGUGAUCCCCCAGAAGGGUGUUCAUCUUUCUCGGGUACCUUCCGGAAGA
ACCUGGAUCCUUACGAGCAGUGGAGCGACCAAGAAAUCUGGAAGGUCGCC
GACGAGGUCGGCCUGCGCUCCGUGAUUGAACAAUUUCCUGGAAAGCUGGA
CUUCGUGCUCGUCGACGGGGGAUGUGUCCUGUCGCACGGACAUAAGCAGC
UCAUGUGCCUCGCACGGUCCGUGCUCUCCAAGGCCAAGAUUCUGCUGCUG
GACGAACCUUCGGCCCACCUGGAUCCGGUCACCUACCAGAUCAUCAGGAG
GACCCUGAAGCAGGCCUUUGCCGAUUGCACCGUGAUUCUCUGCGAGCACC
GCAUCGAGGCCAUGCUGGAGUGCCAGCAGUUCCUGGUCAUCGAGGAGAAC
AAGGUCCGCCAAUACGACUCCAUUCAAAAGCUCCUCAACGAGCGGUCGCU
GUUCAGACAAGCUAUUUCACCGUCCGAUAGAGUGAAGCUCUUCCCGCAUC
GGAACAGCUCAAAGUGCAAAUCGAAGCCGCAGAUCGCAGCCUUGAAGGAA
GAGACUGAGGAAGAGGUGCAGGACACCCGGCUUUAACGGGUGGCAUCCCU
GUGACCCCUCCCCAGUGCCUCUCCUGGCCCUGGAAGUUGCCACUCCAGUG
CCCACCAGCCUUGUCCUAAUAAAAUUAAGUUGCAUCAAGCU
<u>CGACUCUCGG-3′-PO$_4$-3′-GGCUCUCAGC</u>UCGAACUACGUUGAAUUA
AAAUAAUCCUGUUCCGACCACCCGUGACCUCACCGUUGAAGGUCCCGGUC
CUCUCCGUGACCCCUCCCCAGUGUCCCUACGGUGGGCAAUUUCGGCCCAC
AGGACGUGGAGAAGGAGUCAGAGAAGGAAGUUCCGACGCUAGACGCCGAA
GCUAAACGUGAAACUCGACAAGGCUACGCCCUUCUCGAAGUGAGAUAGCC
UGCCACUUUAUCGAACAGACUUGUCGCUGGCGAGCAACUCCUCGAAAACU
UACCUCAGCAUAACCGCCUGGAACAAGAGGAGCUACUGGUCCUUGACGAC
CGUGAGGUCGUACCGGAGCUACGCCACGAGCGUCUCUUAGUGCCACGUUA
GCCGUUUCCGGACGAAGUCCCAGGAGGACUACUAGACCAUCCACUGGCCU
AGGUCCACCCGGCUUCCAAGCAGGUCGUCGUCUUAGAACCGAACCUCUC
GUGCCUGGCACGCUCCGUGUACUCGACGAAUACAGGCACGCUGUCCUGUG
UAGGGGGCAGCUGCUCGUGCUUCAGGUCGAAAGGUCCUUUAACAAGUUAG
UGCCUCGCGUCCGGCUGGAGCAGCCGCUGGAAGGUCUAAAGAACCAGCGA
GGUGACGAGCAUUCCUAGGUCCAAGAAGGCCUUCCAUGGGCUCUUCUACU
UGUGGAAGACCCCCUAGUGCGGCUUCCGGAAGGCGGUGACGACGUCUCAU
UACCUUAGGGUUCUGUGCGGCAGUUAAACCUAAAGGGGGAGCCAUAAGUC
GUCGGCCUCCUUUCGGCUGUCGUCUCAACUGAAGGGCCUUGGCCAGGCGG
GCUCUUCCGGCUGGGCGACAGGGCCGCUUUACCUCUUCGACUACAAAGC
UCUUACCGCAAAGGAGGGAGCCACAUGAAACGCCAGUCCAGGAAGUGCCA
GUAAACUGGAGGCCUCCCGGUUUAUAGCAGGAAGAAGUGCACCCUCAAAA
GCUACUAGUACUGGAACGAGUCGACCGGUAAAAACAUCCCGAAUCACCUG
AAUCACCCAAAAGGGAGUCAUCCGUACAGCUACUUGAACUUGUGCGCCGA

```
CUGCGAAGCGUAGUCCGACAGGUGCAGCUAGCUCGACAAGUGACGGGUGA
CGUCCCACGAGUAUUACAAGUACCGCUCCCAGUCCUAAUAAGGCUGGGCA
GGGAGAGGGAGAGGCCAUCAGUCCUACGACUACUUACACUGGCGCUACUU
CUUCUACUGCUUUUAGUAGAGCUACGCGUAGACCUUGGUGGCGUCCCACC
UGUCCAUGUCCUUGGUUAACCGCCACACCUCCAAGUCCCGGAACACCUUC
UCCCAAAGCUUCAUCCCGACGGCAGGCUUUCGGGCCUCCCAGGUGUCAGG
GAAGUUGCUGCAGUGUUCCACUCACUUCUACCCCCUAGCAGGGAGCCUAA
GGUCAACGAAGUCGACGACCGACCAAACCUCCUUCAUCCGGGCGUCGUAC
UACUUGCGGUGUUACUGGCCGUGUCACCGGUGCUUUUACAUUCCGACGUC
GUGGCGGUGGUGACGCUAACGAGGUUAGUGCUAGUCGUCGUCGACCUACU
UCAGUUUCUACCAUUCGCCGUCCUCUAGCAGGUCCUAUCGCUACAGGAAC
CUCUUAGACAAGUCUUACGGAGGCCGGAAGUCUCACAACUCCCACCUGUA
CCCCCGGACGUCGUGCGAUACGUUGUAGAACACCACUUCUUAGAACGACU
GCCACUAGUUCCACACCUGGUCGCCGUCAGGAGACUUCUUUGGGUAGCGC
UCGUCCCAUAGGCGGUGAGGCUGCAUCUACAUCUUGUGCAUUAUUCUCCU
CCACCUUCACUAUUAGUGCCGUAUCGACAACAAAGAGCUCACGCACCUCA
AAGGGAACAGAACGUCUCCGCACAAAGGGUUGUCGGUCUCGUGGUGGUCA
CUCCGGCGCUGGAGCCGGUCCUUUUAGUGGUCCGUGGUUUAGUCGUGCUU
CUAGUUACUGAACACGUGUCACUACAUGGCGUCUAUUCACAAGGUUCAGC
AGUGCCGCCCAUAGCUGAGGUAUAGCAGCUUCUUCGUGAGAAAGUCUAGG
AGGAGCAACUAAAGAAGCCUUUAAAGCUCGGGCCAAAGGACGCUGCAGA
GGCCCUCAUCUACAGCUCGAGCCAUUCUAAGCGAACUCCACGGUCCCUGU
GAAAGGCCCACCUACGCCAUCAGAACGCCACUUACAAAACCGGGACCAAG
UGCGACACCCAGUAGUCCAAGUCGUGCCUGACGGCGGCGGCCCGAACCUC
GCAGCCUGGUCACCUCUAGUGCCUUUAGGCUCCGUCCUACCGAAGAGGGA
CGAGCGACAGGCCGUGGUCCCUGUCCGCGGAGAGUUCCCCAAGCAGCCUC
AGGAGGAGUUACGGCAAGUAGACGUCACCGCAGAAAACGUGCUAACUCUU
GAACGCCUACCUCAAUUACCCCAAGUUCUACGACAAGAAGGAGAAAAGCG
GCUUAAGGGGCCAGACGAACUUCGAGACGAAGAAUCAGAGCCAGGUACUG
UGUCCCCGCAGCGGAAGGUUUCUCUUCGCCACGUUCCAAAGGCAGUCCUA
GCUCAAGGAAGAAAGCCGCCUCUUGACCAGCUUCGACAGCGUUGGGUAGU
CGAAGCUACUCUUCAGCCCGACGUUCAAGACGUUGAGGCUCUUCCACGGC
AUUUUCAUCCUCCUGGGGAGUACGUCUUAGUCUUUAGAACAGACGGAAGAA
GUCCACGAGGUAAAACCUCCAGUGCUCCUACGCUCAGAACAAUCGGUAGU
CGAACGUGUGCGUGCUAAGCUUCUAGAGGAAAAGCCAGUCCUGCAGGUCC
AUAGGCUUCCCCCUCAGGUCCUCUAUGUCCAGCCGCAGGAAUAUGUGCCG
AGACCGGUCGCUCUAAGAUCGGGCGACCGGGGGGCUGUUCCAUUAUGGGG
GAAGCGGGUCGUGCUACAAUAGAAAGAGGCGCUUGAAACUUUAUAGGAGA
AGGUCGACCGUCCGAAACUAGUGCCUGGCCAUCGCCAUAAGUAGCAUCCU
GUGCGGCUUCUACUACAAAAGGAAUUACCAAGGCCCGUACUAGGUCCUUU
UGACCGAUGUCUUCGACUACGCCGGCCUCACGAACUAGAAAGGGAGCGAU

CCAAGUUCGAGAGGGUACUAGUGGUAGUCGUCCCUUCAGAAAGGCCGAGG
CCAGCUAGGCCGGUGGCGGUCCUCGACAGGAGAAAGCUAGAACUUCAAUU
ACAGGAAGUCGUGCCCGCAGGGCUCGUCCGACUUCAAACUUUUCUUCUCC
CUCAGCAGUGGCAAGCUCCAGAACGCCAACAACAACAAGACGAACCGGAA
GAGCUUGUCAAGCGGUUUAGGGAGGAGGGUUUUCCGCCACUGCAAAGGU
AGUGCUGGAGCCAUCAUCAGUCCAACAUGAGCUCCCAGAACAUGAGGACG
AAAACUUCCUUCAGGACCUAGAACAAUUACCGAGGGUCCCUCAGCAUGGU
UCAGACGUGCCGGGUACCCUUGACGGCCCAGUGCCGGUACGCCUCGUGCU
AUGUCUUCCUUUACCACCACUUCUAGAAGGACUCCUACUAAGGGAAUUAG
UCCCGCAUCCCUCGUGCCUCUCUUUGUGGGUGCUUCUUGGGCCUCUUCUU
CUUUCGCCUGCUCAACUUUAUCGCGUGCAUUCGCCGGAACGCCCAGUCGA
AGUCGAGCCAAACGGCCUCCAAAAGUUAGUAGAAAAGGUACCGGAGAAGG
GUCGUCAUCCGGAAGUGACUGACCUACAAAAGCUAGUAAAGGCUUCACUA
GUGGUCGGCAAGCCUUUAGAAAGGCCGAGAGACCAGGGACAUGAAGUAGU
AGUAGGCGGGGUCAGGCCGGACCUUGUCACGGUCGUGCUAGUCCUUAGGU
UCGGGUGUCUUACGGCUCCGAACGUCGUCGAGGGUCUAGUCCGGGUAGUC
UUCGCGGUGAACGUCUCCCCGCUAGGUGUGCUUCACCCGGUCCCGCUCCG
GGAGCAGCUUGAACAAGUCUAACAACCUCUCGUCCCUGUGCUCGACCGGC
UACCUUUAGAACAGUUCGUGCGCCGAGCUCUCGAAGUCUCAAAAGAACAU
CUAGUCCCUUUUGUACCGUUAAGAGUAGACGUACGGUUACACUACGUCCG
GCUUUUAUCGUCCUACGUUGUUCUCCCAGGCCUGCUACUUUUCGUCCGUG
UCUGGCUACGGGUUCAUCUAUCGCUACGAAGAAAGAAGGAACAACAGCCC
CAGCAUCCUCCGUUAUUAGGCAGGGUCGUUGUCCCCGACGUGCCGGAACC
ACUGGAGAGGGUCCAUCUCCUUCUACGGCAUCUUGUACUUGGCGGUCUUU
UUCGUGGCGGAUUCGCGUAAUUAGUCGAAGCCCAAGAAGAAACUCCGCUC
AAGAGACAGGGUAAGAGAGAGCUCGAAGAGCCUGUCCAACAGGCGCCUCA
GGUGCCUUCCCUAAACUAUCUAUAGCCUGUCGAGGUUCGCGACAGACAUG
GGGAAAGAGUCCUACCCAGAUCAGGUGCUCUUCUUCUCGAACCUGUGGUG
GCUCCGGAAAAGUUCUCCUCUCGCAACGUAGCACAGUUCCUGCCACUCAG
UGAGAACCGUGCCCCUUAGGCGCAAGGUUACGUGGCAAGGGCCGGCGCCU
CCGACCUAGCCAGGGCCACAGAAGAUACCUCCAGUUUUGUCGCACCUACC
GCAGAGGUCCGCUAGACAGG-5'
(Bold base are OMeRNA)
```

Example 2. Exemplary Protein Production with MCNA

This example demonstrates the production of protein encoded by mRNA linked by their 3' ends to a bridging oligonucleotide.

Figure 7:
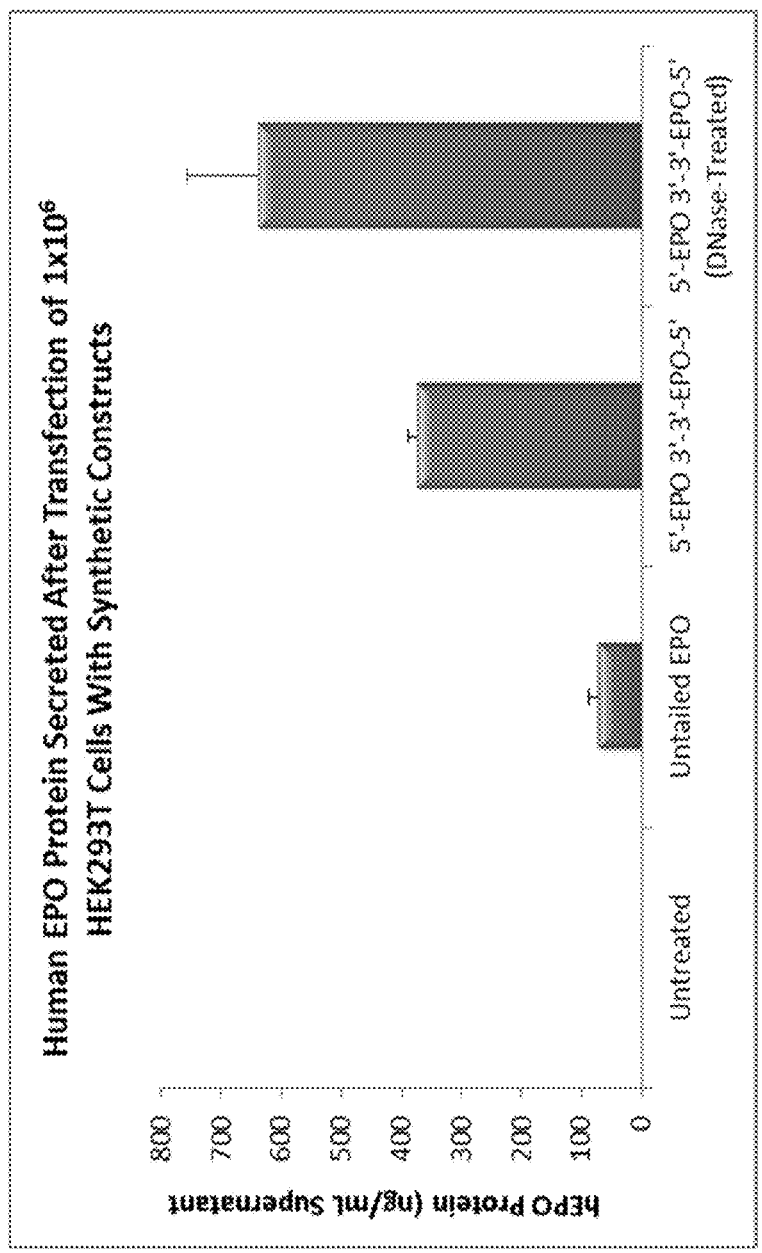
FIG. 7 shows an exemplary graph of the level of hEPO protein secreted after transfection of HEK293T cells with synthetic constructs comprising untailed EPO mRNA or MCNA comprising hEPO mRNA (1 microgram per construct).

MCNA comprising human erythropoietin (hEPO) mRNA were synthesized as described above and used to transfect HEK293T cells (1 microgram RNA transfection per sample). FIG. 7 shows the results of an experiment comparing the amount of secreted hEPO protein from HEK293T cells when the cells were transfected with either a) mRNA encoding hEPO that lacked a polyA tail, b) MCNA comprising hEPO mRNA, or c) MCNA comprising hEPO mRNA that had been treated with DNase. A clear increase in protein production was achieved when the cells were transfected with either the MCNA comprising hEPO mRNA or the DNase-treated MCNA comprising hEPO mRNA compared to the untailed hEPO mRNA.

Figure 9:
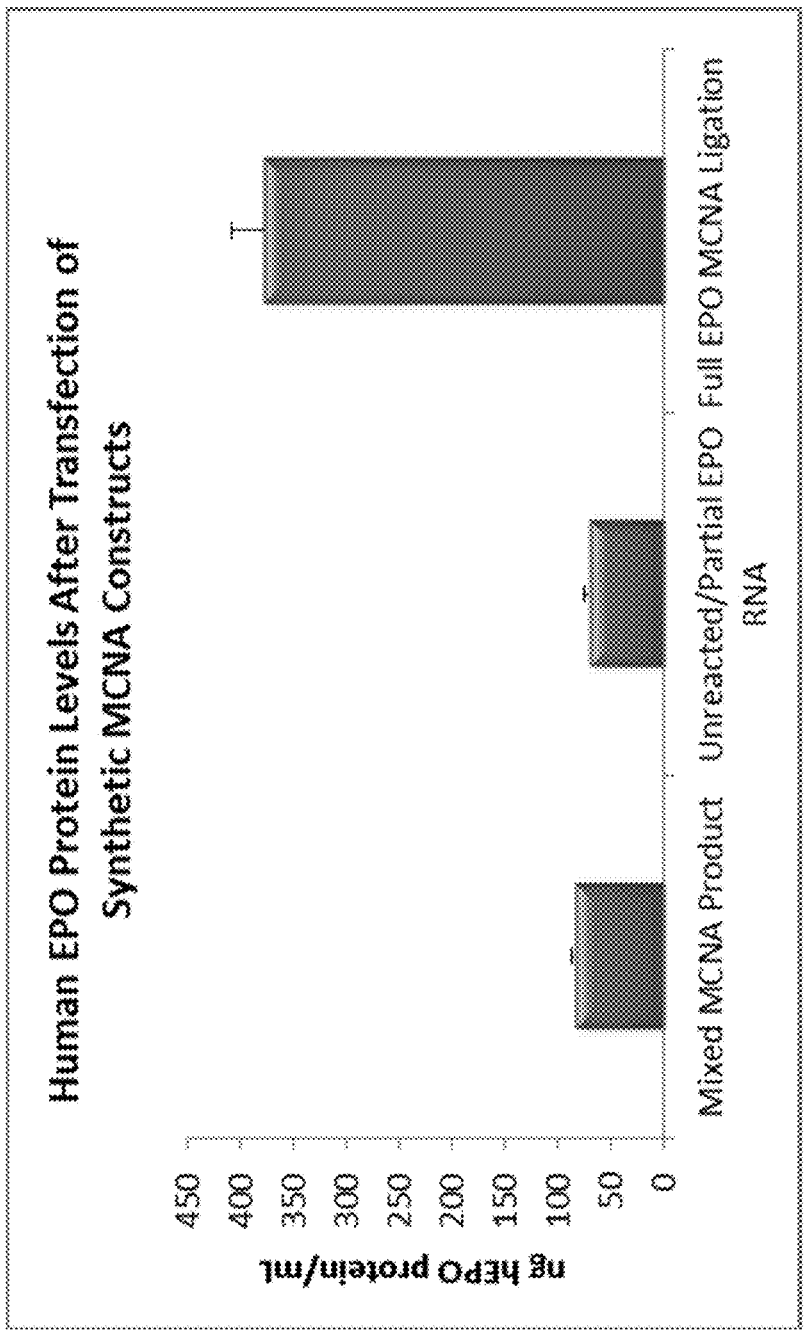
FIG. 9 shows an exemplary graph of the level of hEPO protein secreted after transfection of HEK293T cells with synthetic constructs comprising untailed EPO mRNA or purified MCNA comprising hEPO mRNA (250 nanogram per construct).

FIG. 9 shows the results of an experiment comparing the amount of secreted hEPO protein from HEK293T cells when the cells were transfected with either a) mRNA encoding hEPO that lacked a polyA tail, b) unpurified mixture of MCNA comprising hEPO mRNA with unreacted/partially reacted EPO RNA, c) purified unreacted/partially reacted EPO RNA, or d) purified EPO MCNA. All samples were transfected with a total of 250 nanograms RNA. A clear increase in protein production was achieved when the cells were transfected with purified EPO MCNA compared to the mixture or unreacted hEPO RNA. FIG. 10 shows the results of an experiment comparing the amount of human OTC protein activity (as measured by citrulline production) within HEK293T cells when the cells were transfected with either a) mRNA encoding hOTC that lacked a polyA tail (hOTC monomer), or b) MCNA comprising hOTC mRNA. Detectable protein production was achieved only when the cells were transfected with the MCNA comprising hOTC as compared to the hOTC monomer.

FIG. 11 shows the results of an experiment comparing the amount of human PAH protein produced within HEK293T cells when the cells were transfected with either a) mRNA encoding hPAH that lacked a polyA tail (hPAH monomer), or b) MCNA comprising hPAH mRNA. Significantly higher protein production was achieved when the cells were transfected with the MCNA comprising hPAH as compared to the hPAH monomer.

FIG. 12 shows the results of an experiment comparing the amount of human CFTR protein produced within HEK293T cells when the cells were transfected with either a) mRNA encoding hCFTR that lacked a polyA tail (hCFTR monomer), or b) MCNA comprising hCFTR mRNA. Detectable protein production was achieved only when the cells were transfected with the MCNA comprising hCFTR as compared to the hCFTR monomer.

Example 3. Exemplary In Vivo Protein Production with MCNA

This example demonstrates the in vivo production of protein encoded by mRNA linked by their 3' ends to a bridging oligonucleotide.

Figure 13:
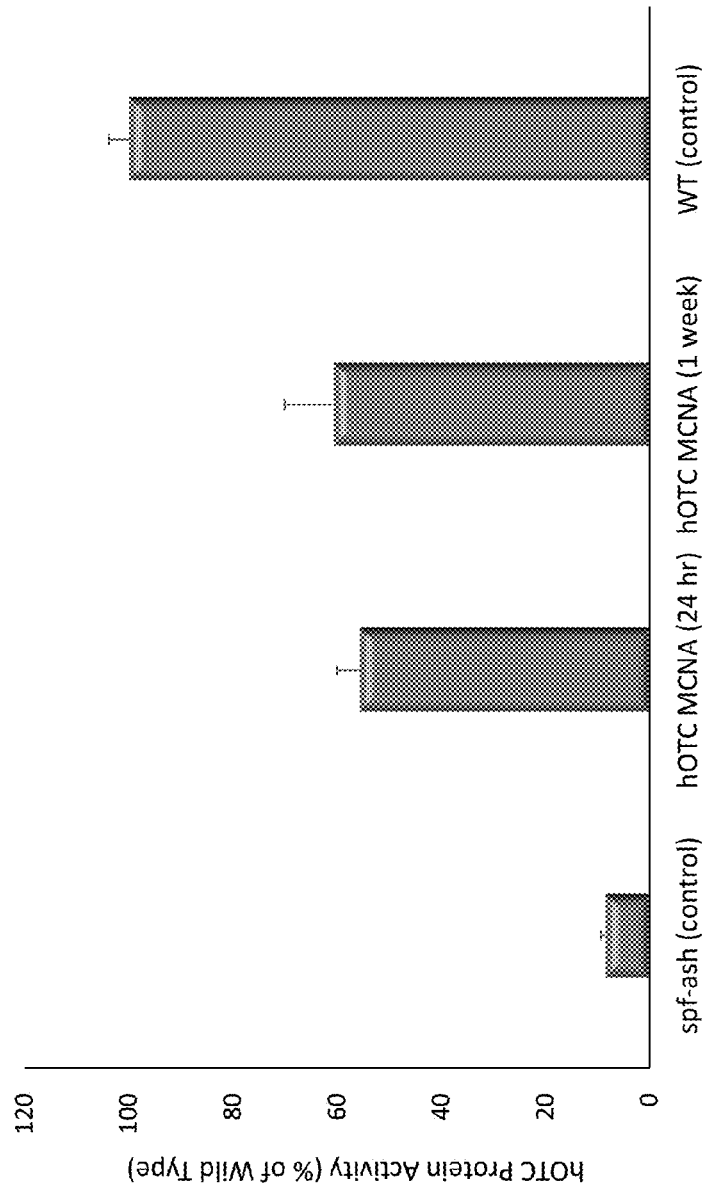
FIG. 13 shows an exemplary graph of citrulline production measured in livers of mice after treatment with hOTC MCNA encapsulated in lipid nanoparticles.
Figure 14:
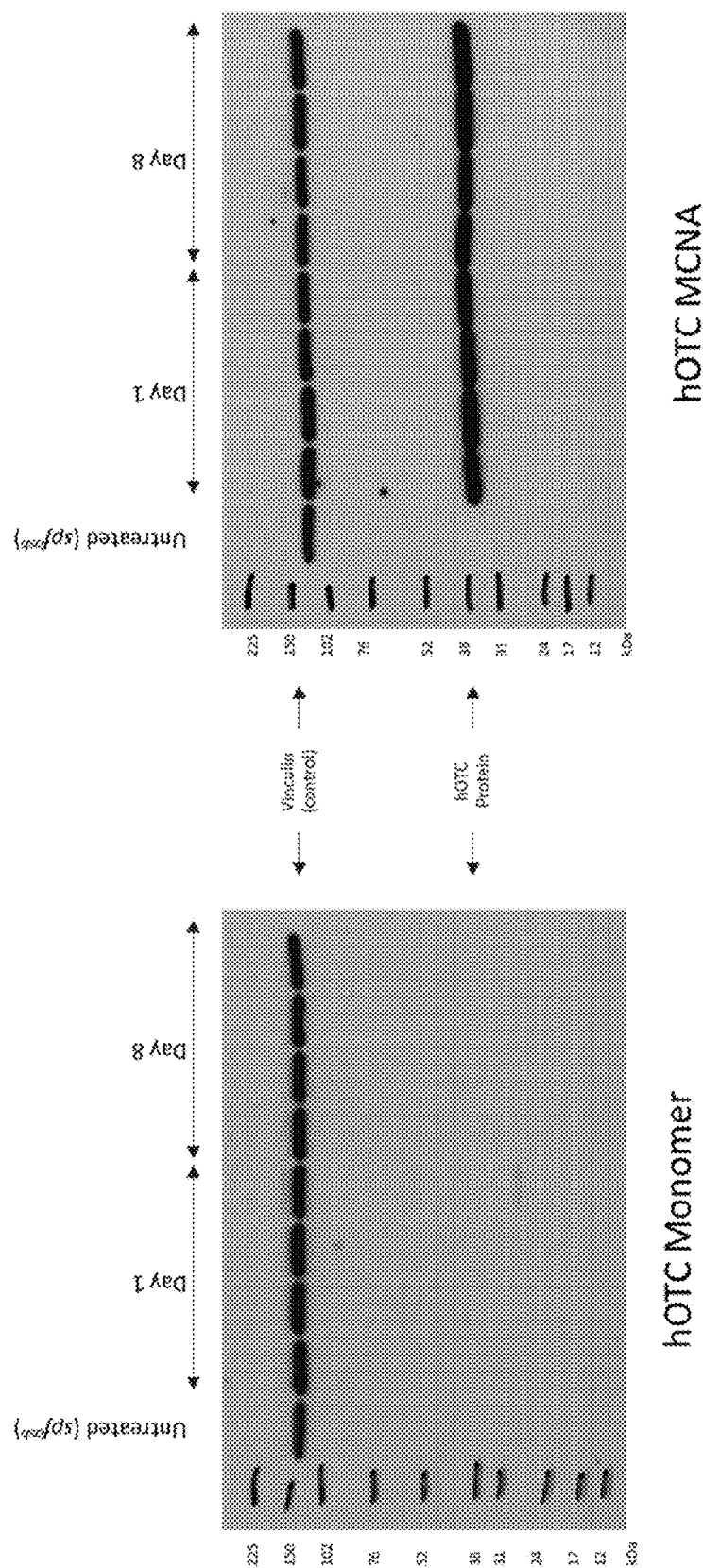
FIG. 14 shows an exemplary Western blot demonstrating hOTC production detected in livers of mice after treatment with hOTC MCNA or hOTC monomers encapsulated in lipid nanoparticles.
Figure 15:
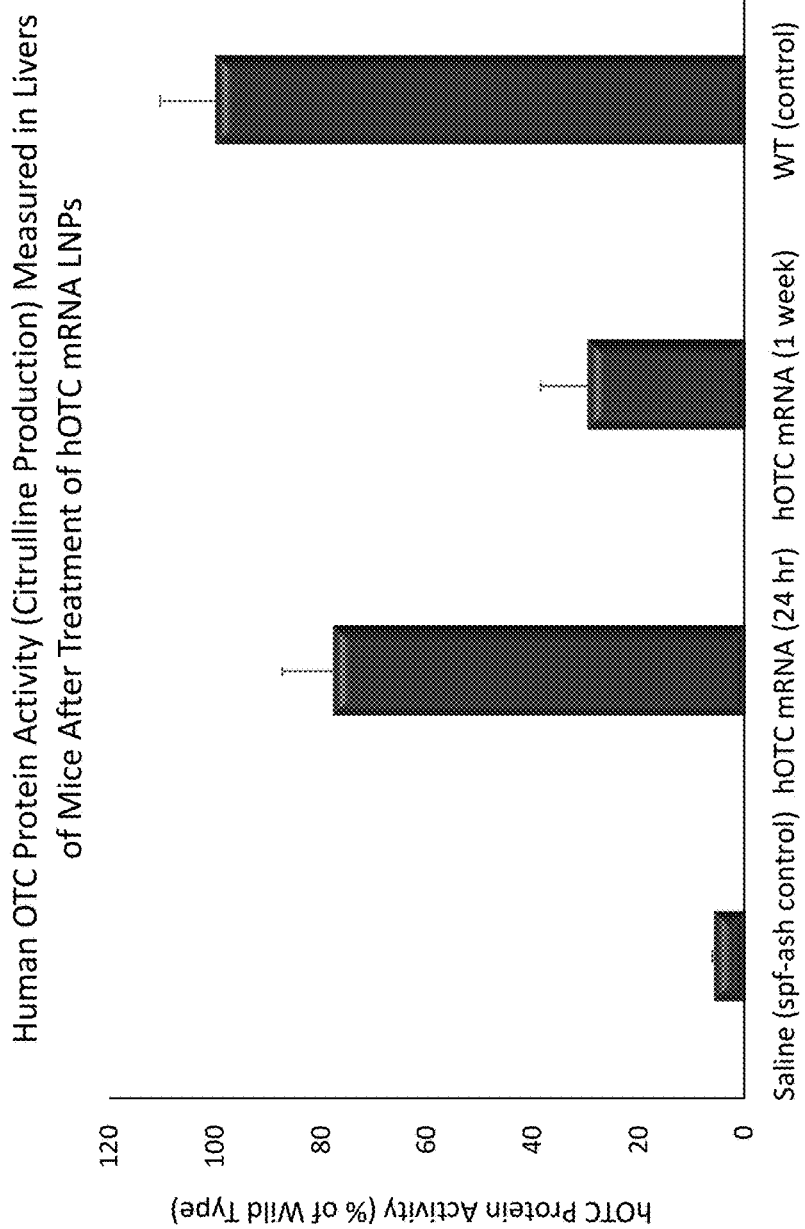
FIG. 15 shows an exemplary graph of citrulline production measured in livers of mice after treatment with hOTC mRNA encapsulated in lipid nanoparticles.
Figure 16:
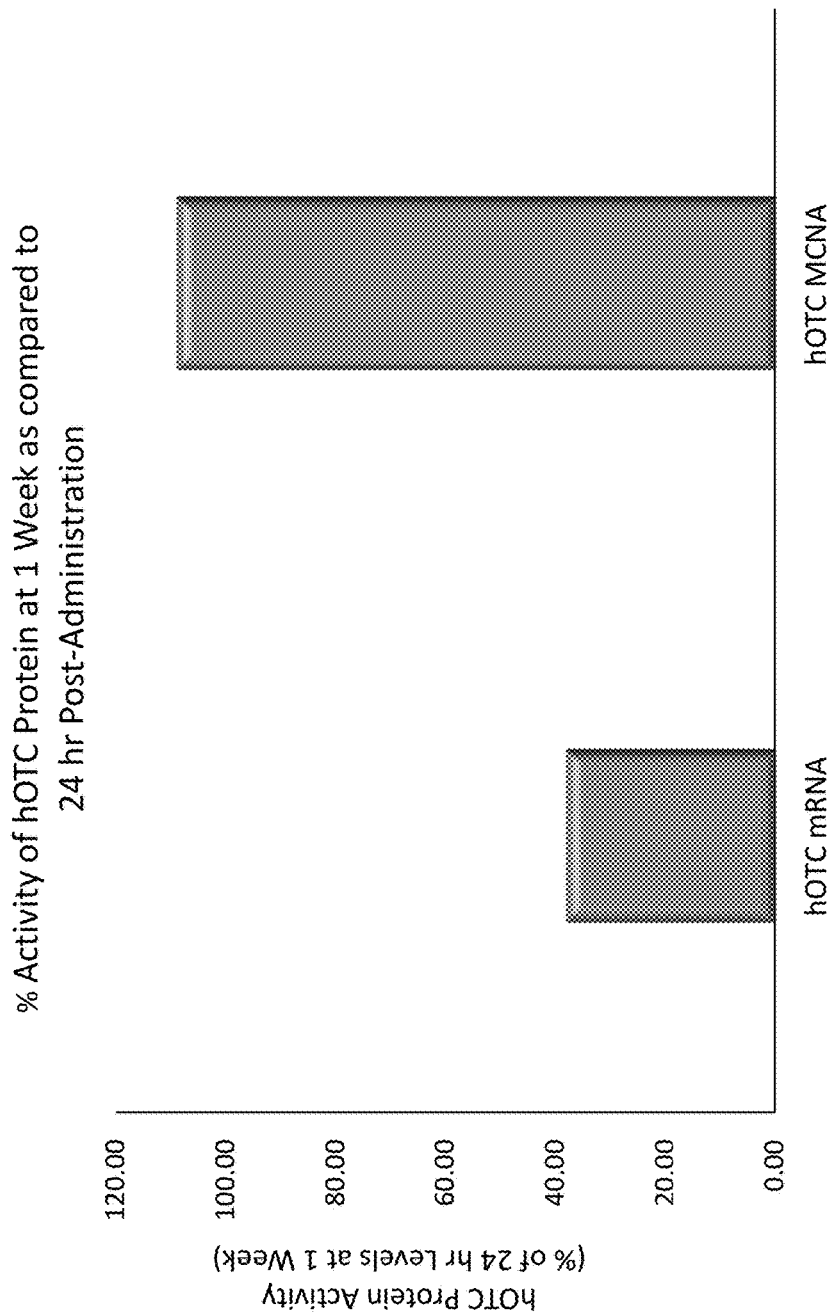
FIG. 16 shows an exemplary graph comparing citrulline production 1 week after administration as a percentage of citrulline production 24 hours after administration in mice treated with hOTC mRNA or hOTC MCNA encapsulated in lipid nanoparticles.

MCNA comprising human ornithine carbamoyltransferase (hOTC) mRNA were synthesized as described above. spf$^{ash}$ mice were treated intravenously with hOTC MCNA encapsulated in lipid nanoparticles. Animals were sacrificed and their livers were isolated either 24 hours or 7 days post-administration. Citrulline production was measured in the liver samples and it was found that the level of hOTC protein activity 7 days post-administration was comparable to the level of hOTC protein activity 24 hours post-administration (FIG. 13). At both time points, hOTC protein activity was significantly greater than in the livers of control spf$^{ash}$ mice. Further, substantial hOTC protein was detected via Western blot at both 1 day and 8 days post-administration, but for only the spf$^{ash}$ mice treated with hOTC MCNA LNPs, not the mice treated with the hOTC monomer LNPs (FIG. 14), consistent with the observed activity data. In comparison, when spf$^{ash}$ mice were treated intravenously with hOTC mRNA, levels of hOTC protein activity were higher 24 hours post-administration than they were 7 days post-administration (FIG. 15). As clearly shown in FIG. 16, when hOTC protein activity 7 day post-administration was calculated as a percentage of activity levels after 24 hours, more sustained in vivo activity is observed for hOTC MCNA (109% of 24 hour activity) than for hOTC mRNA (38% of 24 hour activity).

Figure 17:
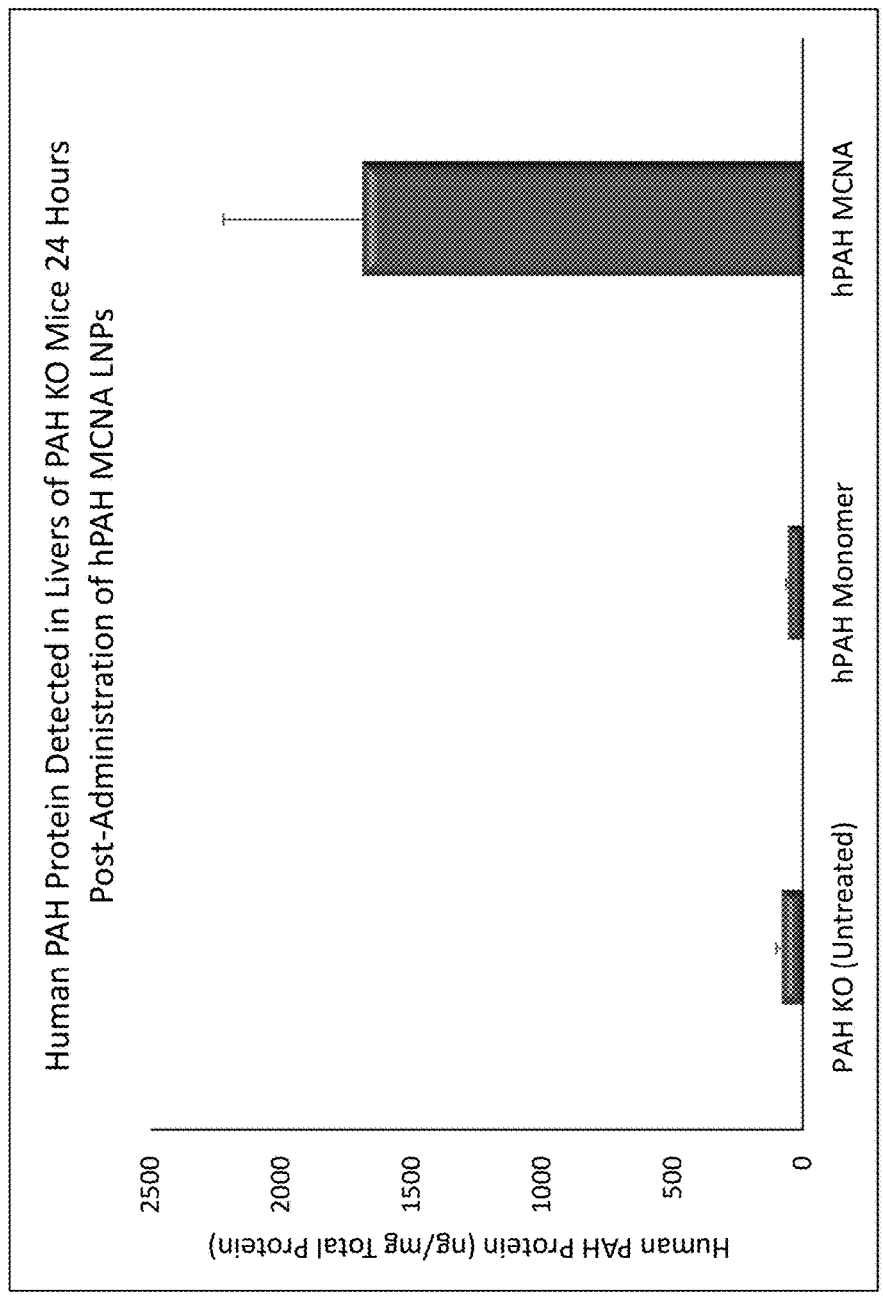
FIG. 17 shows an exemplary graph of hPAH protein detected in livers of PAH knock-out (KO) mice 24 hours after they were administered either hPAH MCNA or hPAH monomers encapsulated in lipid nanoparticles.

In another study, MCNA comprising human phenylalanine hydroxylase (hPAH) were synthesized as described above. PAH knock-out (KO) mice were treated intravenously with either hPAH MCNA or an hPAH monomer (hPAH mRNA with a 5' cap but without a polyA tail) encapsulated in lipid nanoparticles. Animals were sacrificed and their livers were isolated 24 hours post-administration. More than 27 times more hPAH protein was detected in the livers of mice treated with hPAH MCNA than was detected in the livers of mice treated with the hPAH monomer (FIG. 17).

Figure 18:
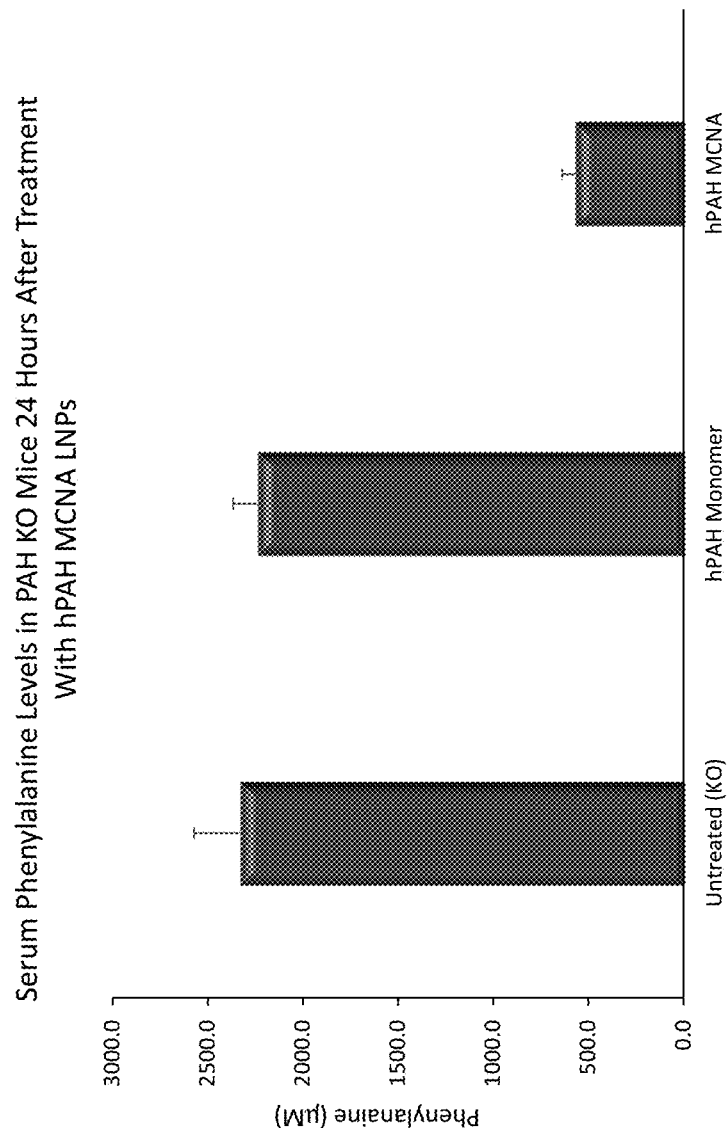
FIG. 18 shows an exemplary graph of serum phenylalanine levels in PAH knock-out (KO) mice 24 hours after they were administered either hPAH MCNA or hPAH monomers encapsulated in lipid nanoparticles.

Further, a demonstration of efficacy was achieved after treatment of PAH knock-out (KO) mice with hPAH MCNA LNPs. Specifically, serum phenylalanine levels were significantly reduced 24 hours after treatment with hPAH MCNA while no reduction in serum phenylalanine was seen 24 hours after treatment with hPAH monomer LNPs (FIG. 18).

Figure 19:
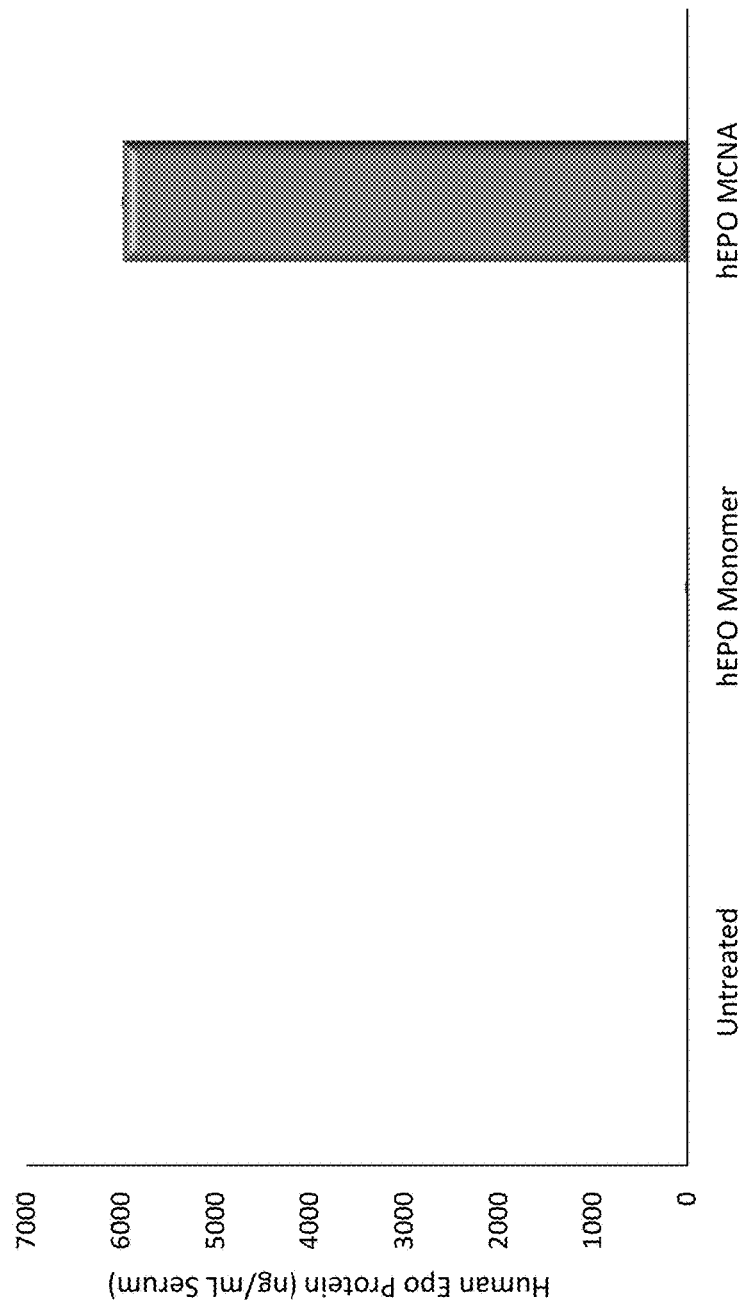
FIG. 19 shows an exemplary graph of hEPO protein detected in the serum of wild-type mice 24 hours after they were administered either hEPO MCNA or hEPO monomers encapsulated in lipid nanoparticles.

In another study, MCNA comprising human erythropoietin (hEPO) were synthesized as described above. Wild-type mice were treated intravenously with either hEPO MCNA or an hEPO monomer (hEPO mRNA with a 5' cap but without a polyA tail) encapsulated in lipid nanoparticles. Serum samples from the animals were obtained 24 hours post-administration. More than 480 times more hEPO protein was detected in the serum of mice treated with hEPO MCNA than was detected in the serum of mice treated with the hEPO monomer (FIG. 19).

Figure 20:
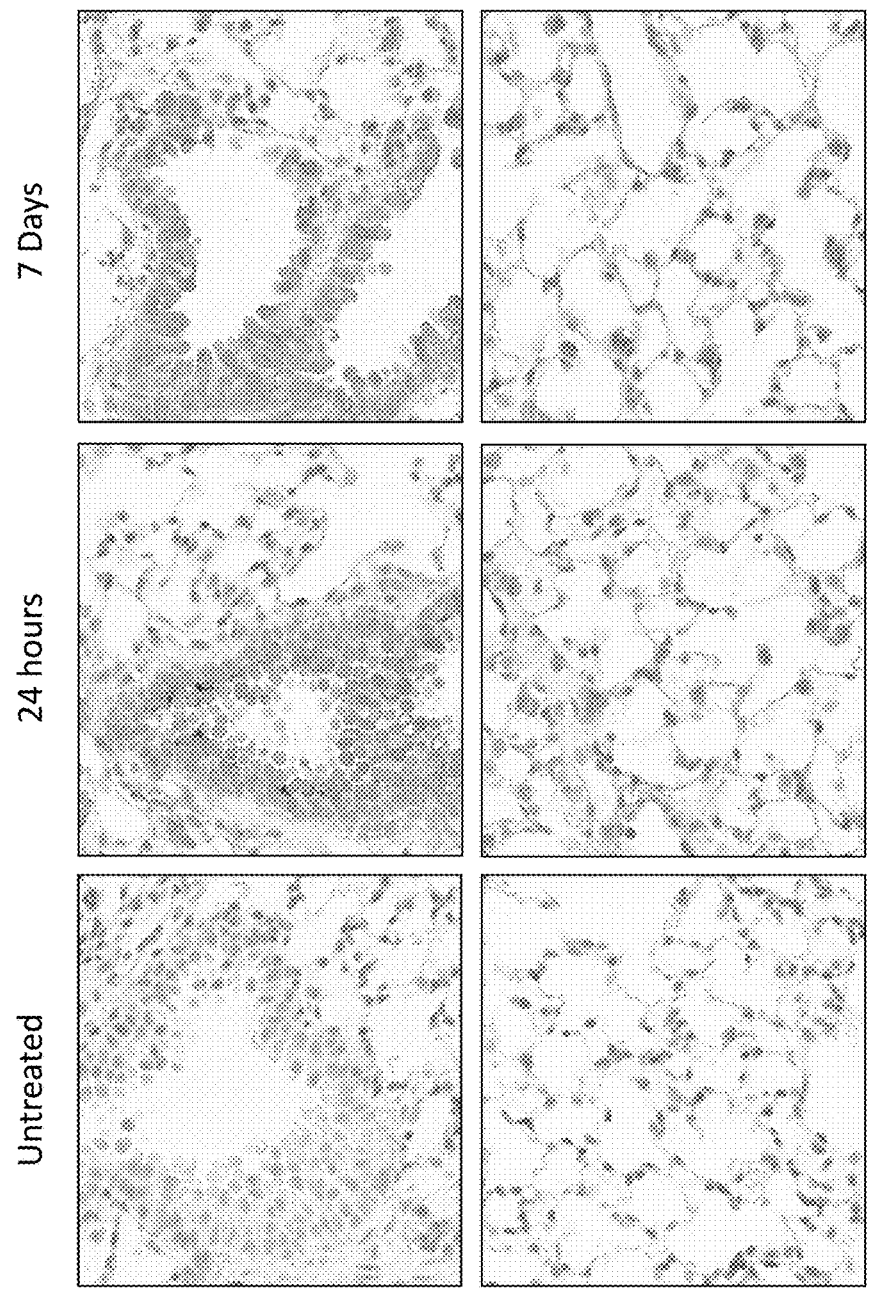
FIG. 20 shows exemplary immunohistochemical detection of human Cystic Fibrosis Transmembrane Conductance Regulator (hCFTR) protein in CFTR KO mouse lung 24 hours and 7 days after treatment with hCFTR MCNA encapsulated in lipid nanoparticles via aerosolization.

In another study, MCNA comprising human cystic fibrosis transmembrane conductance regulator (hCFTR) were synthesized as described above. CFTR KO mice were treated via aerosolization of hCFTR MCNA encapsulated in lipid nanoparticles. Animals were sacrificed and their lungs were isolated either 24 hours or 7 days post-administration. As shown in FIG. 20, MCNA-derived hCFTR protein was detected in both the bronchial epithelial airways (top row) as well as alveolar regions (bottom row) both 24 hours and 7 days post-administration (brown staining).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A multimeric coding nucleic acid (MCNA) comprising two messenger RNAs (mRNAs) linked at 3' ends, via a stable linkage, such that the multimeric coding nucleic acid has two 5' ends, and wherein the stable linkage is an oligonucleotide bridge comprising an internal 3'-to-3' inverted phosphodiester linkage.

2. The MCNA of claim 1, wherein each of the mRNAs encodes a protein of interest.

3. The MCNA of claim 2, wherein each of the mRNAs encodes a same protein.

4. The MCNA of claim 2, wherein each of the mRNAs encodes a distinct protein.

5. The MCNA of claim 1, wherein the mRNAs comprise a 3' UTR.

6. The MCNA of claim 5, wherein the 3' UTR comprises a plurality of multi-A segments with spacers in between.

7. The MCNA of claim 1, wherein the oligonucleotide bridge comprises nucleosides selected from the group consisting of 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine.

8. The MCNA of claim 1, wherein the mRNAs comprise one or more modified nucleosides.

9. The MCNA of claim 8, wherein the modified nucleosides are selected from the group consisting of 2'-OMe-A, 2'-OMe-G, 2'-OMe-C, 2'-OMe-U, 2'-F-A, 2'-F-G, 2'-F-C, 2'-F-U, LNA-A, LNA-G, LNA-C, LNA-U, N6-methyl-adenosine, 2-thiouridine (2sU), 5-methyl-cytidine (5mC), pseudouridine (ΨU), and 1-methyl-pseudouridine.

10. The MCNA of claim 1, wherein each of the mRNAs encodes an enzyme, a receptor, a ligand, a light chain or heavy chain of an antibody, a nuclease, and/or a DNA-binding protein.

11. A composition comprising the MCNA of claim 1 encapsulated or complexed with a delivery vehicle.

12. The composition of claim 11, wherein the delivery vehicle is selected from the group consisting of liposomes, lipid nanoparticles, solid-lipid nanoparticles, polymers, viruses, sol-gels, and nanogels.

13. The MCNA of claim 5, wherein the 3' UTR does not include a polyA tail.

14. The MCNA of claim 1, wherein each of the mRNAs is unmodified.

15. The MCNA of claim 1, wherein the oligonucleotide bridge is unmodified.

16. The MCNA of claim 1, wherein each of the mRNAs has a 5' cap.

* * * * *

SEQUENCE LISTING

<160> NUMBER OF SEQ ID NOS: 26

<210> SEQ ID NO 1
<211> LENGTH: 827
<212> TYPE: RNA
<213> ORGANISM: Artificial Sequence

```
<220> FEATURE:
<223> OTHER INFORMATION: Chemically synthesized nucleotide

<400> SEQUENCE: 1
ggacagaucg ccuggagacg ccauccacgc uguuuugacc uccauagaag acaccgggac      60
cgauccagcc uccgcggccg ggaacggugc auuggaacgc ggauucccccg ugccaagagu    120 gacucaccgu ccuugacacg auggggugc acgaaugucc ugccuggcug uggcuucucc     180 ugcccugcu gucgcucccu cugggccucc caguccuggg cgccccacca cgccucaucu    240
gugacagccg aguccuggag agguaccucu uggaggccaa ggaggccgag aauaucacga    300
cgggcugugc ugaacacugc agcuugaaug agaauaucac ugucccagac accaaaguua    360
auuucuaugc cuggaagagg auggaggucg ggcagcaggc cguagaaguc uggcagggcc    420
uggcccugcu gucggaagcu guccugcggg gccaggcccu guuggucaac ucuucccagc    480
cgugggagcc ccugcagcug caugugauga aagccgucag uggccuucgc agccucacca    540
cucugcuucg ggcucuggga gcccagaagg aagccaucuc cccuccagau gcggccucag    600
cugcuccacu ccgaacaauc acugcugaca cuuccgcaa acucuuccga gucuacucca    660
auuuccuccg gggaaagcug aagcuguaca caggggaggc cugcaggaca ggggacagau    720
gacggguggc aucccuguga ccccuccccca gugccucucc uggcccugga aguugccacu    780
ccagugccca ccagccuugu ccuaauaaaa uuaaguugca ucaagcu                   827

<210> SEQ ID NO 2
<211> LENGTH: 1027
<212> TYPE: RNA
<213> ORGANISM: Artificial Sequence
<220> FEATURE:
<223> OTHER INFORMATION: Chemically synthesized nucleotide

<400> SEQUENCE: 2
ggacagaucg ccuggagacg ccauccacgc uguuuugacc uccauagaag acaccgggac      60
cgauccagcc uccgcggccg ggaacggugc auuggaacgc ggauucccccg ugccaagagu    120 gacucaccgu ccuugacacg auggggugc acgaaugucc ugccuggcug uggcuucucc     180 ugcccugcu gucgcucccu cugggccucc caguccuggg cgccccacca cgccucaucu    240
gugacagccg aguccuggag agguaccucu uggaggccaa ggaggccgag aauaucacga    300
cgggcugugc ugaacacugc agcuugaaug agaauaucac ugucccagac accaaaguua    360
auuucuaugc cuggaagagg auggaggucg ggcagcaggc cguagaaguc uggcagggcc    420
uggcccugcu gucggaagcu guccugcggg gccaggcccu guuggucaac ucuucccagc    480
cgugggagcc ccugcagcug caugugauga aagccgucag uggccuucgc agccucacca    540
cucugcuucg ggcucuggga gcccagaagg aagccaucuc cccuccagau gcggccucag    600
cugcuccacu ccgaacaauc acugcugaca cuuccgcaa acucuuccga gucuacucca    660
auuuccuccg gggaaagcug aagcuguaca caggggaggc cugcaggaca ggggacagau    720
gacggguggc aucccuguga ccccuccccca gugccucucc uggcccugga aguugccacu    780
ccagugccca ccagccuugu ccuaauaaaa uuaaguugca ucaagcuaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaa                                                              1027
```

```
<210> SEQ ID NO 3
<211> LENGTH: 891
<212> TYPE: RNA
<213> ORGANISM: Artificial Sequence
<220> FEATURE:
<223> OTHER INFORMATION: Chemically synthesized nucleotide

<400> SEQUENCE: 3
ggacagaucg ccuggagacg ccauccacgc uguuuugacc uccauagaag acaccgggac      60
cgauccagcc uccgcggccg ggaacggugc auuggaacgc ggauucccg ugccaagagu     120 gacucaccgu ccuugacacg auggggugc acgaaugucc ugccuggcug uggcuucucc    180 ugcccugcu gucgcucccu cugggccucc caguccuggg cgccccacca cgccucaucu     240
gugacagccg aguccuggag agguaccucu uggaggccaa ggaggccgag aauaucacga    300
cgggcugucu ugaacacugc agcuugaaug agaauaucac ugucccagac accaaaguua    360
auuucuaugc cuggaagagg auggaggucg ggcagcaggc cguagaaguc uggcagggcc    420
uggcccugcu gucggaagcu guccugcggg gccaggcccu guuggucaac ucuucccagc    480
cgugggagcc ccugcagcug cauguggaua aagccgucag uggccuucgc agccucacca    540
cucugcuucg ggcucuggga gcccagaagg aagccaucuc cccuccagau gcggccucag    600
cugcuccacu ccgaacaauc acugcugaca cuuccgcaa acucuuccga gucuacucca    660
auuuccuccg gggaaagcug aagcuguaca caggggaggc cugcaggaca ggggacagau    720
gacggguggc aucccuguga ccccucccca gugccucucc uggcccugga aguugccacu    780
ccagugccca ccaaaaaaaa aaaaaaaaaa aaaaaaaaaa aaaaaaaaa aaaaaaaaa     840 aaaaaaaaaa aaaaaaagcc uuguccuaau aaaauuaagu ugcaucaagc u           891

<210> SEQ ID NO 4
<211> LENGTH: 883
<212> TYPE: RNA
<213> ORGANISM: Artificial Sequence
<220> FEATURE:
<223> OTHER INFORMATION: Chemically synthesized nucleotide

<400> SEQUENCE: 4
ggacagaucg ccuggagacg ccauccacgc uguuuugacc uccauagaag acaccgggac      60
cgauccagcc uccgcggccg ggaacggugc auuggaacgc ggauucccg ugccaagagu     120 gacucaccgu ccuugacacg auggggugc acgaaugucc ugccuggcug uggcuucucc    180 ugcccugcu gucgcucccu cugggccucc caguccuggg cgccccacca cgccucaucu     240
gugacagccg aguccuggag agguaccucu uggaggccaa ggaggccgag aauaucacga    300
cgggcugucu ugaacacugc agcuugaaug agaauaucac ugucccagac accaaaguua    360
auuucuaugc cuggaagagg auggaggucg ggcagcaggc cguagaaguc uggcagggcc    420
uggcccugcu gucggaagcu guccugcggg gccaggcccu guuggucaac ucuucccagc    480
cgugggagcc ccugcagcug cauguggaua aagccgucag uggccuucgc agccucacca    540
cucugcuucg ggcucuggga gcccagaagg aagccaucuc cccuccagau gcggccucag    600
cugcuccacu ccgaacaauc acugcugaca cuuccgcaa acucuuccga gucuacucca    660
auuuccuccg gggaaagcug aagcuguaca caggggaggc cugcaggaca ggggacagau    720
gacggguggc aaaaaaaaaa aaaaucccu gugaccccuc cccaaaaaaa aaaaaaaaag    780
ugccucuccu ggcccuggaa aaaaaaaaaa aaaguugcca cuccagugcc caccaaaaaa    840
aaaaaaaaag ccuuguccua auaaaauuaa guugcaucaa gcu                    883
```

```
<210> SEQ ID NO 5
<211> LENGTH: 20
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: MISC_FEATURE
<222> LOCATION: (10)..(11)
<223> OTHER INFORMATION: 3'-3' bridge between nucleotides at positions
      10 and 11 comprises PO4

<400> SEQUENCE: 5
cgacucucgg ggcucucagc                                                    20

<210> SEQ ID NO 6
<211> LENGTH: 20
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: MISC_FEATURE
<222> LOCATION: (10)..(11)
<223> OTHER INFORMATION: 3'-3' bridge between nucleotides at positions
      10 and 11 comprises PO4

<400> SEQUENCE: 6
aaaaaaaaaa aaaaaaaaaa                                                    20

<210> SEQ ID NO 7
<211> LENGTH: 6
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: MISC_FEATURE
<222> LOCATION: (3)..(4)
<223> OTHER INFORMATION: 3'-3' bridge between nucleotides at positions 3
      and 4 comprises PO4

<400> SEQUENCE: 7 aaaaaa                                                                    6

<210> SEQ ID NO 8
<211> LENGTH: 2
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: MISC_FEATURE
<222> LOCATION: (1)..(2)
<223> OTHER INFORMATION: 3'-3' bridge between nucleotides at positions 1
      and 2 comprises PO4

<400> SEQUENCE: 8 aa                                                                        2

<210> SEQ ID NO 9
<211> LENGTH: 37
<212> TYPE: DNA
<213> ORGANISM: Artificial Sequence
<220> FEATURE:
<223> OTHER INFORMATION: Chemically synthesized nucleotide

<400> SEQUENCE: 9
ccgagagtcg agcttgatgc aacttaattt tattagg                                 37
```

```
<210> SEQ ID NO 10
<211> LENGTH: 30
<212> TYPE: DNA
<213> ORGANISM: Artificial Sequence
<220> FEATURE:
<223> OTHER INFORMATION: Chemically synthesized nucleotide

<400> SEQUENCE: 10
ccgagagtga tgcaacttaa ttttattagg                                  30

<210> SEQ ID NO 11
<211> LENGTH: 37
<212> TYPE: DNA
<213> ORGANISM: Artificial Sequence
<220> FEATURE:
<223> OTHER INFORMATION: Chemically synthesized nucleotide

<400> SEQUENCE: 11
tttttttttt agcttgatgc aacttaattt tattagg                          37

<210> SEQ ID NO 12
<211> LENGTH: 30
<212> TYPE: DNA
<213> ORGANISM: Artificial Sequence
<220> FEATURE:
<223> OTHER INFORMATION: Chemically synthesized nucleotide

<400> SEQUENCE: 12
ccgagagtcg tttttttttt tttttttttt                                  30

<210> SEQ ID NO 13
<211> LENGTH: 74
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (37)..(38)
<223> OTHER INFORMATION: 5'-5' bridge between nucleotides at positions
      37 and 38 comprises PO4

<400> SEQUENCE: 13
ggattatttt aattcaacgt agttcgagct gagagccccg agagtcgagc ttgatgcaac  60
ttaattttat tagg                                                   74

<210> SEQ ID NO 14
<211> LENGTH: 60
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (30)..(31)
<223> OTHER INFORMATION: 5'-5' bridge between nucleotides at positions
      30 and 31 comprises PO4

<400> SEQUENCE: 14
ggattatttt aattcaacgt agtgagagcc ccgagagtga tgcaacttaa ttttattagg  60

<210> SEQ ID NO 15
<211> LENGTH: 74
<212> TYPE: DNA
<213> ORGANISM: Artificial Sequence
<220> FEATURE:
<223> OTHER INFORMATION: Chemically synthesized nucleotide
```

```
<220> FEATURE:
<221> NAME/KEY: misc_feature
<222> LOCATION: (37)..(38)
<223> OTHER INFORMATION: 5'-5' bridge between nucleotides at positions
      37 and 38 comprises PO4

<400> SEQUENCE: 15
ggattatttt aattcaacgt agttcgattt tttttttttt tttttttagc ttgatgcaac      60
ttaattttat tagg                                                       74

<210> SEQ ID NO 16
<211> LENGTH: 60
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (30)..(31)
<223> OTHER INFORMATION: 5'-5' bridge between nucleotides at positions
      30 and 31 comprises PO4

<400> SEQUENCE: 16
tttttttttt tttttttttt gctgagagcc ccgagagtcg tttttttttt tttttttttt      60

<210> SEQ ID NO 17
<211> LENGTH: 1674
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (837)..(838)
<223> OTHER INFORMATION: 3'-3' bridge between nucleotides at positions
      837 and 838 comprises PO4

<400> SEQUENCE: 17
ggacagaucg ccuggagacg ccauccacgc uguuuugacc uccauagaag acaccgggac      60
cgauccagcc uccgcggccg ggaacgguge auuggaacgc ggauccccg ugccaagagu      120 gacucaccgu ccuugacacg auggggguge acgaauguce ugccggcug uggcuucucc      180 uguccugcu gucgcucccu cugggccucc agaccuggg cgccccacca cgccucaucu       240
gugacagccg aguccuggag agguaccucu uggaggccaa ggaggccgag aauaucacga     300
cgggcugugc ugaacacugc agcuugaaug agaauaucac uguccagac accaaaguua     360 auuucuaugc cuggaagagg auggaggucg ggcagcaggc cguagaaguc uggcagggcc     420
uggcccugcu gucggaagcu guccugcggg gccaggcccu guuggucaac ucuucccagc     480
cgugggagcc ccugcagcug caugggaua aagccgucag uggccuucgc agccucacca     540
cucugcuucg ggcucuggga gcccagaagg aagccaucuc cccuccagau gcggccucag     600
cugcuccacu ccgaacaauc acugcugaca cuuccgcaa acucuuccga gucuaccuca     660
auuuccuccg gggaaagcug aagcuguaca caggggaggc cugcaggaca ggggacagau     720
gacggguggc aucccuguga ccccucccca guccucuce uggcccugga aguugccacu     780
ccagugccca ccagccuugu ccuaauaaaa uuaaguugca ucaagcucga cucucggggc     840
ucucagcucg aacuacguug aauuaaaaua auccuguucc gaccacccgu gaccucaccg     900
uugaaggucc cgguccucuc cgugacccce cccagugue ccuacgguge gcaguagaca     960 ggggacagga cguccggagg ggacacaugu cgaagucgaa aggggccucc uuuaaccuca    1020
ucugagccuu cucaaacgcc uuucacaguc gucacuaaca agccucaccu cgucgacucc    1080
```

-continued

| | |
|---|---|
| ggcguagacc uccccucuac cgaaggaaga cccgagggguc ucgggcuucg ucucaccacu | 1140 |
| ccgacgcuuc cggugacugc cgaaauaggu guacgucgac guccccgagg gugccgaccc | 1200 |
| uucucaacug guugucccgg accggggcgu ccugucgaag gcugucgucc ggguccggga | 1260 |
| cggucugaag augccggacg acgggcugga gguaggagaa gguccguauc uuuaauugaa | 1320 |
| accacagacc cugucacuau aagaguaagu ucgacgucac aagucgeguc gggcagcacu | 1380 |
| auaagagccg gaggaaccgg agguucucca uggagagguc cugagccgac agugucuacu | 1440 |
| ccgcaccacc ccgcgggucc ugacccuccg ggucucccuc gcugucgucc cuguccucuu | 1500 |
| cggugucggu ccguccugua agcacgugg gguagcacag uuccugccac ucagugagaa | 1560 |
| ccgugccccu uaggcgcaag guuacguggc aagggccggc gccuccgacc uagccagggc | 1620 |
| cacagaagau accuccaguu uugucgcacc uaccgcagag guccgcuaga cagg | 1674 |

<210> SEQ ID NO 18
<211> LENGTH: 1674
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (837)..(838)
<223> OTHER INFORMATION: 3'-3' bridge between nucleotides at positions 837 and 838 comprises PO4

<400> SEQUENCE: 18

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augggggugc acgaauguce ugccuggcug uggcuucucc | 180 |
| ugucccugcu gucgcucccu cugggccucc cagucccuggg cgccccacca cgccucaucu | 240 |
| gugacagccg aguccuggag agguaccucu uggaggccaa ggaggccgag aauaucacga | 300 |
| cgggcugugc ugaacacugc agcuugaaug agaauaucac cgucccagac accaaaguua | 360 |
| auuucuaugc cuggaagagg auggaggucg gcagcaggc cguagaaguc uggcagggcc | 420 |
| uggcccugcu gucggaagcu guccugcggg gccaggcccu guuggucaac ucuucccagc | 480 |
| cgugggagcc ccugcagcug cauguggaua aagccgucag uggccuucgc agccucacca | 540 |
| cucugcuucg ggcucuggga gcccagaagg aagccaucuc ccucccagau gcggccucag | 600 |
| cugcuccacu ccgaacaauc acugcugaca cuuuccgcaa acucuuccga gucuaccca | 660 |
| auuuccuccg gggaaagcug aagcuguaca caggggaggc cugcaggaca gggacagau | 720 |
| gacggguggc auccugguga ccccuccca gugccucucc uggccuuggga aguugccacu | 780 |
| ccagugccca ccagccuugu ccuaauaaaa uuaaguugca ucaagcuaaa aaaaaaaaa | 840 |
| aaaaaaaucg aacuacguug aauuaaaaua auccuguucc gaccaccgu gaccucaccg | 900 |
| uugaaggucc cgguccucuc cgugaccccu ccccagugu ccuacggugg gcaguagaca | 960 |
| ggggacagga cguccggagg ggacacaugu cgaagucgaa aggggccucc uuuaaccuca | 1020 |
| ucugagccuu ucaaacgcc uuucacaguc gucacuaaca agcccaccu cgucgacucc | 1080 |
| ggcguagacc uccccucuac cgaaggaaga cccgagggguc ucgggcuucg ucucaccacu | 1140 |
| ccgacgcuuc cggugacugc cgaaauaggu guacgucgac guccccgagg gugccgaccc | 1200 |
| uucucaacug guugucccgg accggggcgu ccugucgaag gcugucgucc ggguccggga | 1260 |
| cggucugaag augccggacg acgggcugga gguaggagaa gguccguauc uuuaauugaa | 1320 |

```
accacagacc cugucacuau aagaguaagu ucgacgucac aagucguguc gggcagcacu    1380
auaagagccg gaggaaccgg agguucucca uggagagguc cugagccgac agugucuacu    1440
ccgcaccacc ccgcgggucc ugacccuccg ggucucccuc gcugucgucc cuguccucuu    1500
cggugucggu ccguccugua agcacguggg gguagcacag uuccugccac ucagugagaa    1560
ccgugcsccu uaggcgcaag guuacguggc aagggccggc gccuccgacc uagccagggc    1620
cacagaagau accuccaguu uugucgcacc uaccgcagag guccgcuaga cagg           1674
```

```
<210> SEQ ID NO 19
<211> LENGTH: 2074
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (1037)..(1038)
<223> OTHER INFORMATION: 3'-3' bridge between nucleotides at positions
      1037 and 1038 comprises PO4

<400> SEQUENCE: 19
```

```
ggacagaucg ccuggagacg ccauccacgc uguuugacc uccauagaag acaccgggac     60
cgauccagcc uccgcggccg ggaacggugc auuggaacgc ggauucccg ugccaagagu    120 gacucaccgu ccuugacacg auggggguc acgaaugucc ugccggcug uggcuucucc    180 ugucccugcu gucgcucccu cugggccucc cagucceugg cgccccacca cgccucaucu   240
gugacagccg aguccuggag agguaccucu uggaggccaa ggaggccgag aauaucacga   300
cgggcugugc ugaacacugc agcuugaaug agaauaucac ugucccagac accaaaguua   360
auuucuaugc cuggaagagg augggaggucg ggcagcaggc cguagaaguc uggcagggcc   420
uggcccugcu gucggaagcu guccugcggg gccaggcccu guuggucaac ucuucccagc   480 cguggggagcc ccugcagcug caugggguau aagccgucag uggccuucgc agccucacca   540
cucugcuucg ggcucuggga gcccagaagg aagccaucuc cccuccagau gcggccucag   600
cugcuccacu ccgaacaauc acugcugaca cuuccgcaa acucuuccga gucuacucca   660
auuuccuccg gggaaagcug aagcuguaca caggggaggc cugcaggaca ggggacagau   720
gacggguggc aucccuguga ccccucccca gugccucucc uggcccugga aguugccacu   780
ccagugccca ccagccuugu ccuaauaaaa uuaaguugca ucaagcuaaa aaaaaaaaa    840 aaaaaaaaaaa aaaaaaaaa aaaaaaaaa aaaaaaaaa aaaaaaaaa aaaaaaaaa        900 aaaaaaaaaa aaaaaaaaa aaaaaaaaaa aaaaaaaaa aaaaaaaaa aaaaaaaaa        960 aaaaaaaaaa aaaaaaaaa aaaaaaaaaa aaaaaaaaa aaaaaaaaaa aaaaaaaaa      1020 aaaaaaacga cucucggggc ucucagcaaa aaaaaaaaa aaaaaaaaaa aaaaaaaaa      1080 aaaaaaaaaa aaaaaaaaa aaaaaaaaaa aaaaaaaaa aaaaaaaaaa aaaaaaaaa      1140 aaaaaaaaaa aaaaaaaaa aaaaaaaaaa aaaaaaaaa aaaaaaaaaa aaaaaaaaa      1200 aaaaaaaaaa aaaaaaaaa aaaaaaaaaa aaaaaaaaa aaaaaaaucg aacuacguug    1260
aauuaaaaua auccuguucc gaccacccgu gaccucaccg uugaaggucc cgguccucuc   1320 cgugacccu ccccagugu ccuacgguggg gcaguagaca ggggacagga cguccggagg   1380
ggacacaugu cgaagucgaa aggggccucc uuuaaccuca ucugagccuu cucaaacgcc   1440
uuucacaguc gucacuaaca agccucaccu cgucgacucc ggcguagacc uccccucuac   1500
cgaaggaaga cccgagggguc ucgggcuucg ucucaccacu ccgacgcuuc cggugacugc   1560
```

```
cgaaauaggu guacgucgac gucccgagg gugccgaccc uucucaacug guugucccgg    1620
accggggcgu ccugucgaag gcugucgucc cggucggga cggucugaag augccggacg    1680
acgggcugga gguaggagaa gguccguauc uuuaauugaa accacagacc cugucacuau    1740
aagaguaagu ucgacgucac aagucguguc gggcagcacu auaagagccg gaggaaccgg    1800
agguucucca uggagagguc cugagccgac agugucuacu ccgcaccacc ccgcgggucc    1860
ugacccuccg ggucucccuc gcugucgucc cuguccucuu cggugucggu ccguccugua    1920
agcacguggg gguagcacag uuccugccac ucagugagaa ccgugcccu uaggcgcaag    1980 guuacguggc aagggccggc gccuccgacc uagccagggc cacagaagau accuccaguu    2040
uugucgcacc uaccgcagag guccgcuaga cagg                               2074
```

<210> SEQ ID NO 20
<211> LENGTH: 2060
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (1030)..(1031)
<223> OTHER INFORMATION: 3'-3' bridge between nucleotides at positions
      1030 and 1031 comprises PO4

<400> SEQUENCE: 20

```
ggacagaucg ccuggagacg ccauccacgc uguuugacc uccauagaag acaccgggac     60
cgauccagcc uccgcggccg ggaacggugc auuggaacgc ggauucccg ugccaagagu    120 gacucaccgu ccuugacacg auggggguge acgaaugucc ugccuggcug uggcuucucc    180
ugucccugcu gucgucccu cugggccucc caguccuggg cgcccacca cgccucaucu    240 gugacagccg aguccuggag agguaccucu uggaggccaa ggaggccgag aauaucacga    300
cgggcugugc ugaacacugc agcuugaaug agaauaucac uguccagac accaaaguua    360 auuucuaugc cuggaagagg auggaggucg ggcagcaggc cguagaaguc uggcagggcc    420
uggcccugcu gucggaagcu guccugcggg gccaggcccu guuggucaac ucuucccagc    480
cgugggagcc ccugcagcug caugugggaua aagccgucac uggccuucgc agccucacca    540
cucugcuucg ggcucuggga gcccagaagg aagccaucuc cccuccagau gcggccucag    600
cugcuccacu ccgaacaauc acugcugaca cuuuccgcaa acucuuccga gucuaccuca    660
auuuccuccg gggaaagcug aagcuguaca caggggaggc cugcaggaca ggggacagau    720
gacggguggc aucccugugu ccccucccca gugccucucc uggcccugga aguugccacu    780
ccagugccca ccagccuugu ccuaauaaaa uuaaguugca uaagcuaaa aaaaaaaaaa    840 aaaaaaaaaa aaaaaaaaaa aaaaaaaaaa aaaaaaaaaa aaaaaaaaa aaaaaaaaaa    900 aaaaaaaaaa aaaaaaaaaa aaaaaaaaaa aaaaaaaaaa aaaaaaaaa aaaaaaaaaa    960 aaaaaaaaaa aaaaaaaaaa aaaaaaaaaa aaaaaaaaaa aaaaaaaaa aaaaaaaaaa   1020 aaaaaaaaaa aaaaaaaaaa aaaaaaaaaa aaaaaaaaaa aaaaaaaaa aaaaaaaaaa   1080 aaaaaaaaaa aaaaaaaaaa aaaaaaaaaa aaaaaaaaaa aaaaaaaaa aaaaaaaaaa   1140 aaaaaaaaaa aaaaaaaaaa aaaaaaaaaa aaaaaaaaaa aaaaaaaaa aaaaaaaaaa   1200 aaaaaaaaaa aaaaaaaaaa aaaaaaaaaa aaaucgaacu acguugaauu aaaauaauc   1260 uguuccgacc acccgugacc ucaccguuga aggucccggu ccucuccgug acccucccc    1320 aguguccccua cggugggcag uagacagggg acaggacguc cggaggggac acaugucgaa   1380
```

| | |
|---|---|
| gucgaaaggg gccuccuuua accucaucug agccuucuca aacgccuuuc acagucguca | 1440 |
| cuaacaagcc ucaccucguc gacuccggcg uagaccuccc cucuaccgaa ggaagacccg | 1500 |
| agggucucgg gcuucgucuc accacuccga cgcuuccggu gacugccgaa auagguguac | 1560 |
| gucgacgucc ccgagggugc cgacccuucu caacugguug ucccggaccg gggcguccug | 1620 |
| ucgaaggcug ucgucccggu ccgggacggu cugaagaugc cggacgacgg gcuggaggua | 1680 |
| ggagaagguc cguaucuuua auugaaacca cagacccugu cacuauaaga guaaguucga | 1740 |
| cgucacaagu cgugucgggc agcacuauaa gagccggagg aaccggaggu ucccaugga | 1800 |
| gagguccuga gccgacagug ucuacuccgc accaccccgc gggnccugac ccuccgggnc | 1860 |
| ucccucgcug ucgucccugu ccucuuccggu gucggnccgu ccuguaagca cguggggua | 1920 |
| gcacaguucc ugccacucag ugagaaccgu gccccuuagg cgcaagguua cguggcaagg | 1980 |
| gccggcgccu ccgaccuagc cagggccaca gaagauaccu ccaguuuugu cgcaccacc | 2040 |
| gcagaggucc gcuagacagg | 2060 |

```
<210> SEQ ID NO 21
<211> LENGTH: 2056
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (1028)..(1029)
<223> OTHER INFORMATION: 3'-3' bridge between nucleotides at positions
      1028 and 1029 comprises PO4

<400> SEQUENCE: 21
```

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg auggggguc acgaaugucc ugccuggcug uggcuucucc | 180 |
| ugucccugcu gucgcuccu cugggccucc cagaccuggg cgccccacca cgccucaucu | 240 |
| gugacagccg aguccuggag agguaccucu uggaggccaa ggaggccgag aauaucacga | 300 |
| cgggcugugc ugaacacugc agcuugaaug agaauaucac ugcccagac accaaaguua | 360 |
| auuucuaugc cuggaagagg auggaggucg ggcagcaggc cguagaaguc uggcagggcc | 420 |
| uggcccugcu gucggaagcu guccugcggg gccaggcccu guuggucaac ucuucccagc | 480 |
| cgugggagcc ccugcagcug caugugggaua aagccgucag uggccuucgc agcccuacca | 540 |
| cucugcuucg ggcucuggga gcccagaagg aagccaucuc cccuccagau gcggccucag | 600 |
| cugcuccacu ccgaacaauc acugcugaca cuuuccgcaa acucuuccga gucuaccca | 660 |
| auuuccuccg gggaaagcug aagcuguaca caggggaggc cugcaggaca ggggacagau | 720 |
| gacgggnggc aucccugnga cccucccca gugccuucucc uggccccugga aguugccacu | 780 |
| ccagugccca ccagccuugu ccuaauaaaa uuaaguugca ucaagcuaaa aaaaaaaaa | 840 |
| aaaaaaaaaa aaaaaaaaaa aaaaaaaaaa aaaaaaaaaa aaaaaaaaaa aaaaaaaaa | 900 |
| aaaaaaaaaa aaaaaaaaaa aaaaaaaaaa aaaaaaaaaa aaaaaaaaaa aaaaaaaaa | 960 |
| aaaaaaaaaa aaaaaaaaaa aaaaaaaaaa aaaaaaaaaa aaaaaaaaaa aaaaaaaaa | 1020 |
| aaaaaaaaaa aaaaaaaaaa aaaaaaaaaa aaaaaaaaaa aaaaaaaaaa aaaaaaaaa | 1080 |
| aaaaaaaaaa aaaaaaaaaa aaaaaaaaaa aaaaaaaaaa aaaaaaaaaa aaaaaaaaa | 1140 |
| aaaaaaaaaa aaaaaaaaaa aaaaaaaaaa aaaaaaaaaa aaaaaaaaaa aaaaaaaaa | 1200 |

```
aaaaaaaaaa aaaaaaaaa  aaaaaaaaau cgaacuacgu ugaauuaaaa uaauccuguu   1260
ccgaccaccc gugaccucac cguugaaggu cccgguccuc uccgugaccc cuccccagug   1320
ucccuacggu gggcaguaga caggggacag gacguccgga ggggacacau gucgaagucg   1380
aaaggggccu ccuuuaaccu caucugagcc uucucaaacg ccuuucacag ucgucacuaa   1440
caagccucac cucgucgacu ccggcguaga ccuccccucu accgaaggaa gacccgaggg   1500
ucucgggcuu cgucucacca cuccgacgcu uccggugacu gccgaaauag guguacgucg   1560
acguccccga gggugccgac ccuucucaac ugguugucccc ggaccggggc guccugucga   1620
aggcugucgu cccggguccgg gacgucuga agaugccgga cgacgggcug gagguaggag   1680
aagguccgua ucuuuaauug aaaccacaga cccugucacu auaagaguaa guucgacguc   1740
acaagucgug ucgggcagca cuauaagagc cggaggaacc ggagguucuc cauggagagg   1800
uccugagccg acagugucua cuccgcacca ccccgcgggu ccugacccuc cgggucuccc   1860
ucgcugucgu cccuguccuc uucggugucg guccgccug uaagcacgug ggguagcac   1920 aguuccugcc acucagugag aaccgugccc cuuaggcgca agguuacgug gcaagggccg   1980
gcgccuccga ccuagccagg gccacagaag auaccuccag uuuugucgca ccuaccgcag   2040
agguccgcua gacagg                                                  2056

<210> SEQ ID NO 22
<211> LENGTH: 1802
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (901)..(902)
<223> OTHER INFORMATION: 3'-3' bridge between nucleotides at positions
      901 and 902 comprises PO4

<400> SEQUENCE: 22
ggacagaucg ccuggagacg ccauccacgc uguuuugacc uccauagaag acaccgggac     60
cgauccagcc uccgcggccg ggaacggugc auuggaacgc ggauucccg ugccaagagu    120 gacucaccgu ccuugacacg augggggugc acgaaugucc ugccggcug uggcuucucc    180 ugucccugcu gucgcucccu cugggccucc caguccuggg cgccccacca cgccucaucu    240
gugacagccg aguccuggag agguaccucu uggaggccaa ggaggccgag aauaucacga    300
cgggcugugc ugaacacugc agcuugaaug agaauaucac ugucccagac accaaaguua    360
auuucuaugc cuggaagagg auggaggucg ggcagcaggc cguagaaguc uggcagggcc    420
uggcccugcu gucggaagcu guccgcgggg gccaggcccu guuggucaac ucuucccagc    480
cgugggagcc ccugcagcug caugugguaa aagccgucag uggccuucgc agccucacca    540
cucugcuucg ggcucuggga gcccagaagg aagccauccuc cccuccagau gcggccucag    600
cugcuccacu ccgaacaauc acugcugaca cuuuccgcaa acucuuccga gucuaccuca    660
auuuccuccg gggaaagcug aagcuguaca cagggggaggc cugcaggaca ggggacagau    720
gacggguggc auccccuguga ccccucccca gugcccucucc uggccuggga aguugccacu    780
ccagugccca ccaaaaaaaa aaaaaaaaaa aaaaaaaaaa aaaaaaaaaa aaaaaaaaaa     840
aaaaaaaaaa aaaaaaaagcc uuguccaauu aaaauuaagu ugcaucaagc ucgacucucg    900
gggcucucag cucgaacuac guugaauuaa aauaauccug uucgaaaaaa aaaaaaaaaa    960
aaaaaaaaaa aaaaaaaaaa aaaaaaaaaa aaaaaaaaaa aaaaaaaaaa ccacccguga   1020
```

-continued

| | |
|---|---|
| ccucaccguu gaaggucccg guccucuccg ugaccccucc ccagugcccc uacgguggc | 1080 |
| aguagacagg ggacaggacg uccggagggg acacaugucg aagucgaaag gggccuccuu | 1140 |
| uaaccucauc ugagccuucu caaacgccuu ucacagucgu cacuaacaag ccucaccucg | 1200 |
| ucgacuccgg cguagaccuc cccucuaccg aaggaagacc cgaggucuc gggcuucguc | 1260 |
| ucaccacucc gacgcuuccg ugacugccg aaauaggugu acgucgacgu ccccgagggu | 1320 |
| gccgacccuu cucaacuggu uguccccggac cggggcgucc ugucgaaggc ugucgucccg | 1380 |
| guccgggacg gucugaagau gccggacgac gggcuggagg uaggagaagg uccguaucuu | 1440 |
| uaauugaaac cacagacccu gucacuauaa gaguaaguuc gacgucacaa gucgugucgg | 1500 |
| gcagcacuau aagagccgga ggaaccggag guucuccaug gagagguccu gagccgacag | 1560 |
| ugucuacucc gcaccacccc gcggguccug acccuccggg ucccccucgc ugucgucccu | 1620 |
| guccucuucg gugucgguccc guccuguaag cacggggggu uagcacaguu ccugccacuc | 1680 |
| agugagaacc gugcccuua ggcgcaaggu uacgguggcaa gggccggcgc uccgaccua | 1740 |
| gccagggcca cagaagauac cuccaguuuu gucgcaccua ccgcagaggu ccgcuagaca | 1800 |
| gg | 1802 |

<210> SEQ ID NO 23
<211> LENGTH: 1786
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (893)..(894)
<223> OTHER INFORMATION: 3'-3' bridge between nucleotides at positions
      893 and 894 comprises PO4

<400> SEQUENCE: 23

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg auggggugc acgaaugucc ugccuggcug uggcuucucc | 180 |
| ugucccugcu gucgcucccu cugggccucc caguccuggg cgcccaccca cgccucaucu | 240 |
| gugacagccg aguccuggag agguaccucu uggaggccaa ggaggccgag aauaucacga | 300 |
| cgggcugugc ugaacacugc agcuugaaug agaauaucac ugucccagac accaaaguua | 360 |
| auuucuaugc cuggaagagg auggaggucg ggcagcaggc cguagaaguc uggcagggcc | 420 |
| uggcccugcu gucggaagcu guccugcggg gccaggcccu guuggucaac ucuucccagc | 480 |
| cgugggagcc ccugcagcug caugggauaa agccgucag uggccuucgc agccucacca | 540 |
| cucugcuucg ggcucuggga gcccagaagg aagccaucuc cccuccagau gcggccucag | 600 |
| cugcuccacu ccgaacaauc acugcugaca cuuuccgcaa acucuuccga gucuacccca | 660 |
| auuccuccg gggaaagcug aagcuguaca caggggaggc cugcaggaca ggggacagau | 720 |
| gacggguggc aaaaaaaaaa aaaaaucccu gugaccccuc cccaaaaaaa aaaaaaaag | 780 |
| ugccucuccu ggcccuggaa aaaaaaaaa aaaguugcca cuccagugcc caccaaaaaaa | 840 |
| aaaaaaaag ccuuguccua auaaauuaa guugcaucaa gcucgacucu cggggcucuc | 900 |
| agcucgaacu acguugaauu aaaauaaucc uguccgaaa aaaaaaaaaa aaccaccgu | 960 |
| gaccucaccu uugaaaaaaa aaaaaaaagg ucccgguccu cuccgugaaa aaaaaaaaaa | 1020 |
| aaaccccucc ccagugucccu uaaaaaaaaa aaaaacggu gggcaguaga caggggacag | 1080 |

-continued

```
gacguccgga ggggacacau gucgaagucg aaaggggccu ccuuuaaccu caucugagcc    1140
uucucaaacg ccuuucacag ucgucacuaa caagccucac cucgucgacu ccggcguaga    1200 ccucccucu accgaaggaa gacccgaggg ucucgggcuu cgucucacca cuccgacgcu     1260
uccggugacu gccgaaauag guguacgucg acgucccga gggugccgac ccuucucaac     1320 ugguugucc ggaccggggc guccugucga aggcugucgu cccgguccgg gacggucuga     1380
agaugccgga cgacgggcug gagguaggag aagguccgua ucuuuaauug aaaccacaga    1440
cccugucacu auaagaguaa guucgacguc acaagucgug ucgggcagca cuauaagagc    1500
cggaggaacc ggagguucuc cauggagagg uccugagccg acagugucua cuccgcacca    1560
ccccgcgggu ccugacccuc cgggucuccc ucgcugucgu cccuguccuc uucggugucg    1620
guccguccug uaagcacgug gggguagcac aguccugcc acucagugag aaccgugccc     1680
cuuaggcgca agguuacgug gcaagggccg gcgccuccga ccuagccagg gccacagaag    1740
auaccuccag uuuugucgca ccuaccgcag aggucggcua gacagg                  1786
```

```
<210> SEQ ID NO 24
<211> LENGTH: 2640
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (1320)..(1321)
<223> OTHER INFORMATION: 3'-3' bridge between nucleotides at positions
      1320 and 1321 comprises PO4

<400> SEQUENCE: 24
```

```
ggacagaucg ccuggagacg ccauccacgc uguuugacc uccauagaag acaccgggac      60
cgauccagcc uccgcggccg ggaacggugc auuggaacgc ggauuccccg ugccaagagu    120
gacucaccgu ccuugacacg augcuguuca accuucggau cuugcugaac aacgcugcgu    180
uccggaaugg ucacaacuuc augguccgga acuucagaug cggccagccg cuccagaaca    240
aggugcagcu caaggggagg gaccuccuca cccugaaaaa cuucaccgga gaagagauca    300
aguacaugcu guggcuguca gccgaccuca aauuccggau caagcagaag ggcgaauacc    360
uuccuuugcu gcagggaaag ucccugggga ugaucuucga gaagcgcagc acucgcacua    420
gacugucaac ugaaaccggc uucgcgcugc ugggaggaca ccccugcuuc cugaccaccc    480
aagauaucca ucuggugugu aacgaauccc ucaccgacac agcgcgggug cugucgucca    540
uggcagacgc gguccucgcc cgcguguaca agcagucuga ucuggacacu cuggccaagg    600
aagccuccau uccuaucauu aauggauugu ccgaccucua ccaucccauc cagauucugg    660
ccgauuaucu gacucugcaa gaacauuaca gcucccugaa ggggcuuacc cuuucgugga    720
ucggcgacgg caacaacauu cugcacagca uuaugaugag cgcugccaag uuuggaaugc    780
accuccaagc agcgaccccg aagggauacg agccagacgc cuccgugacg aagcuggcug    840
agcaguacgc caaggagaac ggcacuaagc ugcugcucac caacgacccu cucgaagccg    900 cccacgguggg caacgugcug aucaccgaua ccuggaucuc cauggacag gaggaggaaa   960 agaagaagcg ccugcaagca uuucaggggu accaggugac uaugaaaacc gccaaggucg   1020
ccgccucgga cuggaccuuc uugcacuguc ugcccagaaa gcccgaagag guggacgacg   1080 agguuucua cagcccgcgg ucgcuggucu uccggaggcc cgaaacagg aaguggacua     1140 ucauggccgu gauggugucc cugcugaccg auuacucccc gcagcugcag aaaccaaagu   1200
```

```
ucugacgggu ggcaucccug ugaccccucc ccagugccuc uccuggcccu ggaaguugcc    1260
acuccagugc ccaccagccu uguccuaaua aaauuaaguu gcaucaagcu cgacucucgg    1320
ggcucucagc ucgaacuacg uugaauuaaa auaauccugu uccgaccacc cgugaccuca    1380
ccguugaagg ucccgguccu cuccgugacc ccuccccagu gucccuacgg ugggcagucu    1440
ugaaaccaaa gacgucgacg ccccucauua gccagucguc ccuggguag ugccgguacu     1500 aucaggugaa ggacaaaagc cggaggccuu ucuggucgcu ggcgcccgac aucuugguga    1560
gcagcaggug gagaagcccg aaagacccgu cugucacguu cuuccagguc aggcuccgcc    1620
gcuggaaccg ccaaaaguau caguggacca uggggacuuu acgaacgucc gcgaagaaga    1680
aaaggaggag gacagggguac cucuaggucc auagccacua gucgugcaac gguggcaccc    1740
gccgaagcuc ucccagcaac cacucgucgu cgaaucacgg caagaggaac cgcaugacga    1800
gucggucgaa gcagugccuc cgcagaccga gcauagggaa gccccagcga cgaaccucca    1860
cguaagguuu gaaccgucgc gaguaguauu acgacacguc uuacaacaac ggcagcggcu    1920
aggugcuuuc ccauucgggg aaguccccucg acauuacaag aacgucucag ucuauuagcc    1980
ggucuuagac cuacccuacc aucuccagcc uguuagguaa uuacuauccu uaccuccgaa    2040
ggaaccgguc ucaggucu agucugacga acaugugcgc ccgcuccugg cgcagacggu     2100
accugcuguc gugggcgcga cacagccacu cccuaagcaa gugugggucu accuauagaa    2160
cccaccagcu cuucgucccc acaggaggu cgucgcgcuu cggccaaagu caacugucag     2220
aucacgcuca cgacgcgaag agcuucuagu agggguccecu gaaagggacg ucguuuccuu    2280
ccauaagcgg gaagacgaac uaggccuuaa acuccagccg acugucggug ucguacauga    2340
acuagagaag aggccacuuc aaaaaguccc acuccuccag ggaggggaac ucgacgugga    2400
acaagaccuc gccgaccggc guagacuuca aggccuggua cuucaacacu gguaaggccu    2460
ugcgucgcaa caagucguuc uaggcuucca acuugucgua gcacaguucc ugccacucag    2520
ugagaaccgu gccccuuagg cgcaagguua cguggcaagg gccggcgccu ccgaccuagc    2580
cagggccaca gaagauaccu ccaguuuugu cgcaccuacc gcagaggucc gcuagacagg    2640
```

<210> SEQ ID NO 25
<211> LENGTH: 3228
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (1614)..(1615)
<223> OTHER INFORMATION: 3'-3' bridge between nucleotides at positions
      1614 and 1615 comprises PO4

<400> SEQUENCE: 25

```
ggacagaucg ccuggagacg ccauccacgc uguuugacc uccauagaag acaccgggac       60
cgauccagcc uccgcggccg ggaacggugc auuggaacgc ggauucccg ugccaagagu      120 gacucaccgu ccuugacacg augagcaccg ccgugcugga aaccccggc cugggccgca      180 agcugagcga cuucgccag gagaccagcu acaucgagga caacugcaac cagaacggcg      240
ccaucagccu gaucuucagc cugaaggagg aggugggcgc ccuggccaag gugcugcgcc      300
uguucgagga gaacgacgug aaccugaccc acaucgagag ccgccccagc cgccugaaga      360
aggacgagua cgaguucuuc acccaccugg acaagcgcag ccugcccgcc cugaccaaca      420
ucaucaagau ccugcgccac gacaucggcg ccaccgugca cgagcugagc cgcgacaaga      480
```

| | |
|---|---|
| agaaggacac cgugcccugg uuccccgca ccauccagga gcuggaccgc uucgccaacc | 540 |
| agauccugag cuacggcgcc gagcuggacg ccgaccaccc cggcuucaag gaccccgugu | 600 |
| accgcgcccg ccgcaagcag uucgccgaca ucgccuacaa cuaccgccac ggccagccca | 660 |
| ucccccgcgu ggaguacaug gaggaggaga agaagaccug gggcaccgug uucaagaccc | 720 |
| ugaagagccu guacaagacc cacgccugcu acgaguacaa ccacaucuuc ccccugcugg | 780 |
| agaaguacug cggcuuccac gaggacaaca uccccagcu ggaggacgug agccaguucc | 840 |
| ugcagaccug caccggcuuc cgccugcgcc ccguggccgg ccugcugagc agccgcgacu | 900 |
| uccugggcgg ccuggccuuc cgcguguucc acugcaccca guacauccgc cacggcagca | 960 |
| agcccaugua cacccccgag cccgacaucu gccacgagcu gcugggccac gugcccugu | 1020 |
| ucagcgaccg cagcuucgcc caguucagcc aggagaucgg ccuggccagc cugggcgccc | 1080 |
| ccgacgagua caucgagaag cuggccacca ucuacugguu caccguggag uucggccugu | 1140 |
| gcaagcaggg cgacagcauc aaggccuacg gcgccggccu gcugagcagc uucggcgagc | 1200 |
| ugcaguacug ccugagcgag aagcccaagc ugcugcccu ggagcuggag aagaccgcca | 1260 |
| uccagaacua caccgugacc gaguccagc cccuguacua cguggccgag agcuucaacg | 1320 |
| acgccaagga gaaggugcgc aacuucgccg ccaccauccc ccgccccuuc agcgugcgcu | 1380 |
| acgaccccua cacccagcgc aucgaggugc uggacaacac ccagcagcug aagauccugg | 1440 |
| ccgacagcau caacagcgag aucggcaucc ugugcagcgc ccugcagaag aucaaguaac | 1500 |
| gggguggcauc ccugugaccc cucccagug ccucccugg cccggaagu ugccacucca | 1560 |
| gugcccacca gccuuguccu aauaaaauua aguugcauca agcucgacuc ucggggcucu | 1620 |
| cagcucgaac uacguugaau uaaaauaauc cguuccgac cacccgugac cucaccguug | 1680 |
| aaggucccgg uccucccgu gaccccuccc cagugcccu acggugggca augaacuaga | 1740 |
| agacgucccg cgacgugucc uacggcuaga gcgacaacua cgacagccgg uccuagaagu | 1800 |
| cgacgaccca caacaggucg uggagcuacg cgacccacau ccccagcauc gcgugcgacu | 1860 |
| ucccccgcccc cuaccaccgc cgcuucaacg cguggaagag gaaccgcagc aacuucgaga | 1920 |
| gccggugcau caugucccg accuugagcc aguccacau caagaccuac cgccagaaga | 1980 |
| ggucgaagggu cccgucgucg aaccccgaaga gcgagugccgu caugacgucg agcggcuucg | 2040 |
| acgagucguc cggccgcggc auccggaacu acgacagcgg gacgaacgug uccggccuuga | 2100 |
| ggugccacuu ggucaucuac caccggucga agagcuacau gagcagcccc cgcggguccg | 2160 |
| accgguccgg cuagaggacc gacuugaccc gcuucgacgc cagcgacuug uccccgugca | 2220 |
| ccgggucguc gagcaccguc uacagcccga gccccacau guacccgaac gacggcaccg | 2280 |
| ccuacaugac ccacgucacc uugugcgccu ccggccgg cgggccuuc agcgccgacg | 2340 |
| agucguccgg ccggugcccc cgguccgccu ucggccacgu ccagacgucc uugaccgagu | 2400 |
| gcaggagguc gaccccuac aacaggagca ccuucggcgu caugaagagg ucgucccccu | 2460 |
| ucuacaccaa caugagcauc guccgcaccc agaacaugau cgagaaguccc agaacuugu | 2520 |
| gccacggggu ccagaagaag aggaggaggu acaugaggug cgcccccuac ccgaccggca | 2580 |
| ccgccaucaa cauccgcuac agccgcuuga cgaacgccgc ccgcgccaug ugccccagga | 2640 |
| acuucggccc caccagccgc aggucgagcc gcggcaucga guccuagacc aaccgcuucg | 2700 |
| ccaggucgag gaccaccac gccccuugg ucccgugcca caggaagaag aacagcgccg | 2760 |
| agucgagcac gugccaccgc ggcuacagca ccgcguccua gaacuacuac aaccaguccc | 2820 |
| gcccgucccga cgcgaacagg uccacccacu ucuugagcau gagcaggaag aaguccgccg | 2880 |

-continued

| | |
|---|---|
| acccegccga gagcuacacc caguccaagu gcagcaagag gagcuugucc gcgucguga | 2940 |
| accgguccg cgggugggg aggaaguccg acuucuaguc cgacuaccgc ggcaagacca | 3000 |
| acgucaacag gagcuacauc gaccagagga ccggcuucag cgagucgaac gccggguccg | 3060 |
| gccccaagag gucgugccgc cacgaguagc acaguccug ccacucagug agaaccgugc | 3120 |
| cccuuaggcg caagguuacg uggcaagggc cggcgccucc gaccuagcca gggccacaga | 3180 |
| agauaccucc aguuuugucg caccuaccgc agaggccgc uagacagg | 3228 |

<210> SEQ ID NO 26
<211> LENGTH: 9396
<212> TYPE: RNA
<213> ORGANISM: Artificial Sequence
<220> FEATURE:
<223> OTHER INFORMATION: Chemically synthesized nucleotide
<220> FEATURE:
<221> NAME/KEY: misc_feature
<222> LOCATION: (4698)..(4699)
<223> OTHER INFORMATION: 3'-3' bridge between nucleotides at positions 4698 and 14699 comprises PO4

<400> SEQUENCE: 26

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg augcaacgcu cuccucuuga aaaggccucg gugguguccha | 180 |
| agcucuucuu cucguggacu agaccauccc ugagaaaggg guacagacag cgcuuggagc | 240 |
| uguccgauau cuaucaaauc ccuuccgugg acuccgcgga caaccuguccc gagaagcucg | 300 |
| agagagaaug ggacagagaa cucgccucaa agaagaaccc gaagcugauu aaugcgcuua | 360 |
| ggcggugcuu uuucuggcgg uucauguucu acggcaucuu ccucuaccug ggagagguca | 420 |
| ccaaggccgu gcagccccug uugcugggac ggauuauugc cuccuacgac cccgacaaca | 480 |
| aggaagaaag aagcaucgcu aucuacuugg gcaucggucu gugccugcuu ucaucgucc | 540 |
| ggacccucuu guugcauccu gcuauuuucg gccugcauca cauuggcaug cagaugagaa | 600 |
| uugccauguu ucccugauc uacaagaaaa cucugaagcu cucgagccgc gugcuugaca | 660 |
| agauuuccau cggccagcuc cugucccgc ucuccaacaa ucgaacaag uucgacgagg | 720 |
| gccucgcccu ggcccacuuc gugguggaucg ccccucugca aguggcgcuu cugaugggcc | 780 |
| ugaucuggga gcugcugcaa gccucggcau ucguggggcu uggauuccug aucgugcugg | 840 |
| cacguuccca ggccggacug gggcggauga ugaugaagua cagggaccag agagccggaa | 900 |
| agauuuccga acggcuggug aucacuucgg aaaugaucga aaacauccag ucagugaagg | 960 |
| ccuacugcug ggaagaggcc augaaaaga ugauugaaaa ccuccggcaa accgagcuga | 1020 |
| agcugaccg caaggccgcu acgugcgcu auuucaacuc guccgcuuuc uucuucuccg | 1080 |
| gguucuucgu gguguuucuc uccgugcucc ccuacgcccu gauuaaggga aucauccuca | 1140 |
| ggaagaucuu caccaccauu uccuucugua ucgugcuccg cauggccgug acccggcagu | 1200 |
| ucccauggc cgucagacu gguacgacu cccugggagc cauuaacaag auccaggacu | 1260 |
| uccuucaaaa gcaggaguac aagaccccucg aguacaaccu gacuacuacc gaggucguga | 1320 |
| uggaaaacgu caccgccuuu ugggaggagg gauuggcga acguucgag aaggccaagc | 1380 |
| agaacaacaa caaccgcaag accucgaacg gugacgacuc ccucuucuuu ucaaacuuca | 1440 |
| gccugcucgg gacgccgug cugaaggaca uuaacuucaa gaucgaaaga ggacagcucc | 1500 |
| uggcggugc cggaucgacc ggagccggaa agacuucccu gcugauggu aucauggag | 1560 |

```
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu caaaguucg    1740 cggagaaaga uaacaucgug cugggcgaag ggguauuac cuugucgggg ggccagcggg    1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggnccu ccuacuuuua cggcaccuuc ucggaguugc   2040
agaacuugca gcccgacuuc ucaucgaagc ugaugggunug cgacagcuuc gaccaguucu   2100
ccgccgaaag aaggaacucg auccugacg aaaccuugca ccgcuucucu uuggaaggcg    2160 acgcccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg acagcgagc agggagaagc cauccugccu cggauuuccg    2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520 uguccuggc accucaagcg aaucuuaccg agcucgacau cuacucccgg agacugucgc    2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuggugccu ggugauuuuc cuggccgagg    2760
ucgcggccuc acuggugguu cucuggcugu ugggaaacac gccucugcaa gacaagggaa   2820
acuccacgca cucgagaaac aacagcuaug ccgugauuau cacuuccacc uccucuuauu   2880 acguuucua caucuacguc ggaguggcgg auacccugcu cgcgaugggu uucuucagag   2940
gacugccgcu gguccacacc uugaucaccg ucagcaagau ucuucaccac aagauguuge   3000 auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauuggag caaucgcagu gguggcggug cugcagccuu   3180
acauuuucgu ggccacugug ccggucauug uggcguucau caugcugcgg gccuacuucc   3240
uccaaaccag ccagcagcug aagcaacugg aauccgaggg acgauccccc aucuucacuc   3300
accuugugac gucguugaag ggacuguuga cccucccggc uuucggacgg cagcccuacu   3360
ucgaaacccu cuuccacaag gcccugaacc uccacaccgc caauugguuc cuguaccguu   3420
ccacccugcg guguuccag augcgcaucg agaugauuuu cgucaucuuc ucaucgcgg    3480 ucacauucau cagcauccug acuaccgag agggagaggg acgggucgga auaauccuga   3540
cccucgccau gaacauuaug agcaccggc agugggcagu gaacagcucg aucgacgugg   3600
acagccugau gcgaagcguc agccgcgugu caaguucau cgacaugccu acugagggaa    3660
aacccacuaa guccacuaag cccuacaaaa auggccagcu gagcaagguc augaucaucg   3720 aaaacucccca cgugaagaag gacgauauuu ggcccuccgg aggucaaaug accgugaagg   3780
accugaccgc aaaguacacc gagggaggaa acgccauucu cgaaaacauc agcuuccca    3840 uuucgccgga acagcggguc ggccuucucg ggcgaccgg uucgggaag ucaacucugc    3900 ugucggcuuu ccuccggcug cugaauaccg aggggggaaau ccaaauugac ggcgugucuu   3960
```

```
gggauuccau uacucugcag caguggcgga aggccuucgg cgugaucccc cagaaggugu    4020
ucaucuucuc ggguaccuuc cggaagaacc uggauccuua cgagcagugg agcgaccaag    4080
aaaucuggaa ggucgccgac gaggucggcc ugcgcuccgu gauugaacaa uuuccuggaa    4140
agcuggacuu cgugcucguc gacggggau guguccuguc gcacggacau aagcagcuca     4200
ugugccucgc acgguccgug cucuccaagg ccaagauucu gcugcuggac gaaccuucgg    4260
cccaccugga uccggucacc uaccagauca ucaggaggac ccugaagcag gccuuugccg    4320
auugcaccgu gauucucugc gagcaccgca ucgaggccau gcuggagugc cagcaguucc    4380
uggucaucga ggagaacaag guccgccaau acgacuccau ucaaaagcuc cucaacgagc    4440
ggucgcuguu cagacaagcu auuucaccgu ccgauagagu gaagcucuuc ccgcaucgga    4500
acagcucaaa gugcaaaucg aagccgcaga ucgcagccuu gaaggaagag acugaggaag    4560
aggugcagga cacccggcuu uaacgggugg cauccccugug accccucccc agugccucuc    4620
cuggcccugg aaguugccac uccagugccc accagccuug uccuaauaaa auuaaguugc    4680
aucaagcucg acucucgggg cucucagcuc gaacuacguu gaauuaaaau aauccuguuc    4740
cgaccacccg ugaccucacc guugaagguc ccgguccucu ccgugacccc uccccagugu    4800
cccuacggug ggcaauuucg gcccacagga cguggagaag gagucagaga aggaaguucc    4860
gacgcuagac gccgaagcua aacgugaaac ucgacaaggc uacgcccuuc ucgaagugag    4920
auagccugcc acuuuaucga acagacuugu cgcuggcgag caacucccg aaaacuuacc     4980 ucagcauaac cgccuggaac aagaggagcu acuguccuu gacgaccgug aggucguacc     5040
ggagcucacg cacgagcguc ucuuagugcc acguuagccg uuccggacg aagucccagg     5100 aggacuacua gaccauccac uggccuaggu ccacccggcu uccaagcagg ucgucgucuu    5160
agaaccggaa ccucucgugc cuggcacgcu ccguguacuc gacgaauaca ggcacgcugu    5220
ccuguguagg gggcagcugc ucgugcuuca ggucgaaagg uccuuuaaca aguuagugcc    5280
ucgcguccgg cuggagcagc cgcuggaagg ucuaaagaac cagcgaggug acgagcauuc    5340
cuagguccaa gaaggccuuc caugggcucu ucuacuugug gaagacccc uagugcggcu      5400 uccggaaggc ggugacgacg ucucauuacc uuaggguucu gugcggcagu uaaaccuaaa    5460
gggggagcca uaagucgucg gccuccuuuc ggcugucguc ucaacugaag ggccuuggcc    5520
aggcgggcuc uuccggcugg gcgacagggc cgcuuuaccu cuucgacuac aaaagcucuu    5580
accgcaaagg agggagccac augaaacgcc aguccaggaa gugccaguaa acuggaggcc    5640
ucccgguuua uagcaggaag aagugcaccc ucaaaagcua cuaguacugg aacgagucga    5700
ccgguaaaaa caucccgaau caccugaauc acccaaaagg gagucauccg uacagcuacu    5760
ugaacuugug cgccgacugc gaagcguagu ccgacaggug cagcuagcuc gacaagugac    5820
gggugacguc ccacgaguau uacaaguacc gcucccaguc uaauaaggc ugggcaggga     5880 gagggagagg ccaucagucc uacgacuacu uacacuggcg cuacuucuuc uacugcuuuu    5940
aguagagcua cgcguagacc uugguggcgu cccaccuguc caugccuug guuaaccgcc     6000 acaccuccaa gucccggaac accuucuccc aaagcuucau cccgacggca ggcuuucggg    6060
ccucccaggu gucagggaag uugcugcagu guuccacuca cuucuacccc cuagcaggga    6120 gccuaaagguc aacgaagucg acgaccgacc aaaccuccuu cauccgggcg ucguacuacu   6180
ugcgguguua cuggccgugu caccggugcu uuuacauucc gacgucgugg cgguggugac    6240
gcuaacgagg uuagucuag cgucgucga ccuacuucag uuucuaccau ucgccgccu       6300 cuagcaagguc cuaucgcuac aggaaccucu uagacaaguc uuacggaggc cggaagucuc    6360
```

```
acaacuccca ccuguacccc cggacgucgu gcgauacguu guagaacacc acuucuuaga    6420
acgacugcca cuaguccac accggucgc cgucaggaga cuucuuuggg uagcgcucgu      6480
cccauaggcg gugaggcugc aucuacaucu ugugcauuau ucuccuccac cuucacuauu    6540
agugccguau cgacaacaaa gagcucacgc accucaaagg gaacagaacg ucuccgcaca    6600
aagguuguc ggucucgugg uggucacucc ggcgcuggag ccgguccuuu uagugguccg     6660
ugguuuaguc gugcuucuag uuacugaaca cgucacacua cauggcgucu auucacaagg    6720
uucagcagug ccgcccauag cugagguaua gcagcuucuu cgugagaaag ucaggagga    6780
gcaacuaaag aagccuuuaa agcucgggcc aaaggacgcu gucagaggcc cucaucuaca    6840
gcucgagcca uucuaagcga acuccacggu cccugugaaa ggcccaccua cgccaucaga    6900
acgccacuua caaaaccggg accaagugcg acacccagua guccaagucg ugccugacgg    6960
cggcggcccg aaccucgcag ccuggucacc ucuagugccu uuaggcuccg uccuaccgaa    7020
gagggacgag cgacaggccg uggcccugu ccgcggagag uucccaagc agccucagga     7080
ggaguuacgg caaguagacg ucaccgcaga aaacgugcua acucuugaac gccuaccuca    7140
auuaccccaa guucuacgac aagaaggaga aaagcggcuu aaggggccag acgaacuucg    7200
agacgaagaa ucagagccag guacuguguc cccgcagcgg aagguuucuc uucgccacgu    7260
uccaaaggca guccuagcuc aaggaagaaa gccgccucuu gaccagcuuc gacagcguug    7320
gguagucgaa gcuacucuuc agcccgacgu ucaagacguu gaggcucuuc cacggcauuu    7380
ucauccuccu ggggaguacg ucuuagucuu agaacagacg gaagaaguccc acgagguaaa   7440
accuccagug cuccuacgcu cagaacaauc gguagucgaa cgugcgcug cuaagcuucu     7500
agaggaaaag ccaguccugc agguccauag gcuuccccu cagguccucu auguccagcc     7560
gcaggaauau gugccgagac cggucgcucu aagaucgggc gaccgggggg cuguuccauu    7620
auggggaag cgggucgugc uacaauagaa agaggcgcuu gaaacuuuau aggagaaggu     7680
cgaccguccg aaacuagugc cuggccaucg ccauaaguag cauccugugc ggcuucuacu    7740
acaaaaggaa uuaccaaggc ccguacuagg uccuuuugac cgaugucuuc gacuacgccg    7800
gccucacgaa cuagaaaggg agcgauccaa guucgagagg guacuagugg uagucguccc    7860
uucagaaagg ccgaggccag cuaggccggu ggcgguccuc gacaggagaa agcuagaacu    7920
ucaauuacag gaagucgugc ccgcagggcu cguccgacuu caaacuuuuc uucccccuca    7980
gcaguggcaa gcuccagaac gccaacaaca acaagacgaa ccggaagagc uugucaagcg    8040
guuuagggag gagggguuuuc cgccacugca aaggguagug cuggagccau caucagucca    8100
acaugagcuc ccagaacaug aggacgaaaa cuuccuucag gaccuagaac aauuaccgag    8160
ggucccucag cauggúucag acgugccggg uacccuugac ggcccagugc cgguacgccu    8220
cgugcuaugu cuuccuuuac caccacuucu agaaggacuc cuacuaaggg aauuagcccc    8280
gcaucccuc gugccucucu uugguggcu ucuggggccu cuucuucuuu cgccugcuca      8340
acuuuaucgc gugcauucgc cggaacgccc agucgaaguc gagccaaacg gccuccaaaa    8400
guuaguagaa aagguaccgg agaagggucg ucauccggaa gugacugacc uacaaaagcu    8460
aguaaaggcu ucacuagugg ucggcaagcc uuuagaaagg ccgagagacc agggacauga    8520
aguaguagua ggcggggguca ggccggaccu ugucacgguc gugcuagucc uuagguucgg    8580
gugucuuacg gcuccgaacg ucgucgaggg cuaguccgg guagucuucg cggugaacgu    8640
cuccccgcua ggugugcuuc acccggucccc gcuccgggag cagcuugaac aagucuaaca    8700
accucucguc ccugugcucg accggcuacc uuuagaacag uucgugcgcc gagcucucga    8760
```

```
agucucaaaa gaacaucuag ucccuuuugu accguuaaga guagacguac gguuacacua    8820
cguccggcuu uuaucguccu acguuguucu cccaggccug cuacuuuucg uccgugucug    8880
gcuacggguu caucuaucgc uacgaagaaa gaaggaacaa cagccccagc auccuccguu    8940
auuaggcagg gucguugucc ccgacgugcc ggaaccacug gagagggucc aucuccuucu    9000
acggcaucuu guacuuggcg gucuuuuucg uggcggauuc gcguaauuag ucgaagccca    9060
agaagaaacu ccgcucaaga gacaggguaa gagagagcuc gaagagccug uccaacaggc    9120
gccucaggug ccuucccuaa acuaucuaua gccugucgag guucgcgaca gacaugggga    9180
aagaguccua cccagaucag gugcucuucu ucucgaaccu gugguggcuc cggaaaaguu    9240
cuccucucgc aacguagcac aguuccugcc acucagugag aaccgugccc cuuaggcgca    9300
agguuacgug gcaagggccg gcgccuccga ccuagccagg gccacagaag auaccuccag    9360
uuuugucgca ccuaccgcag agguccgcua gacagg                              9396
```